(12) United States Patent
Hamprecht et al.

(10) Patent No.: US 6,639,070 B1
(45) Date of Patent: Oct. 28, 2003

(54) N-SUBSTITUTED PERHYDRODIAZINE

(75) Inventors: Gerhard Hamprecht, Weinheim (DE); Michael Puhl, Lampertheim (DE); Olaf Menke, Altleiningen (DE); Robert Reinhard, Ludwigshafen (DE); Ingo Sagasser, Dannstadt (DE); Cyrill Zagar, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/009,836

(22) PCT Filed: Jun. 23, 2000

(86) PCT No.: PCT/EP00/05792

§ 371 (c)(1),
(2), (4) Date: Dec. 17, 2001

(87) PCT Pub. No.: WO01/00600

PCT Pub. Date: Jan. 4, 2001

(30) Foreign Application Priority Data

Jun. 24, 1999 (DE) .......................... 199 28 963

(51) Int. Cl.[7] ............................. C07D 273/04
(52) U.S. Cl. ..................... 544/66; 544/68; 540/598
(58) Field of Search ............... 544/66, 68; 540/598

(56) References Cited

U.S. PATENT DOCUMENTS 3,428,631 A    2/1969  Trapainer et al. ........... 260/243

FOREIGN PATENT DOCUMENTS

WO    WO 94/10173    5/1994
WO    WO 95/06643    3/1995

OTHER PUBLICATIONS

Samitov et al. "Synthesis, $^1$H and $^{13}$C NMR Spectra, and Dynamic Stereochemistry of 2–Monosubstituted and 2,2–Disubstituted 4–Aryl(Alkyl)–Carbamoyl–3,4,56–Tetrahydro–1,2,4–oxadiazines" Zhurnal Organoicheskoi Khimii, vol. 18, No. 7 (1982) pp. 1520–1528.

Primary Examiner—John M. Ford
(74) Attorney, Agent, or Firm—Keil & Weinkauf

(57) ABSTRACT

N-substituted perhydro-2,3-diazines of the formula I

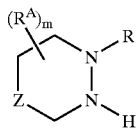

(I)

in which the variables Z, R, m and $R^A$ are as defined in claim 1, a process for their preparation and the use of the compounds of the formula I as starting materials for preparing herbicides of the formula V

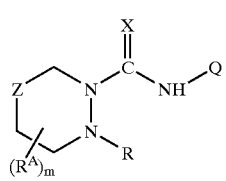

(V)

in which R, $R^A$, Z and m are as defined above, X is O or S and Q is a $C_6$–$C_{14}$-aromatic radical are described.

6 Claims, No Drawings

N-SUBSTITUTED PERHYDRODIAZINE

The present invention relates to 1-oxa- and 1-thia-3,4-diazines which are substituted in the 4-position, to a process for their preparation and to their use in a process for preparing novel herbicidally active compounds.

WO 94/10173 discloses perhydrogenated 1-oxa-3,4-diazines of the formula A in which Z is S, O, S=O or $SO_2$ and Q is a $C_6$–$C_{14}$-aromatic radical. The compounds A are used as starting materials for preparing herbicides with triazoline-2,5-dione structure (Compounds B).

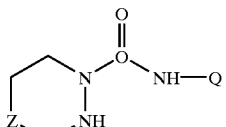

(A)

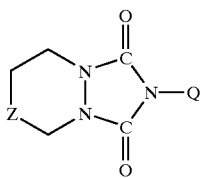

(B)

The compounds of the formula A for their part are prepared by cyclization of substituted N-(N'-arylcarbamoyl)hydrazinoethanols or -thiols with formaldehyde under acidic reaction conditions. The yields of such cyclization reactions are not satisfactory.

In another invention, which is the subject of a parallel application, it has surprisingly been found that compounds of the formula A'

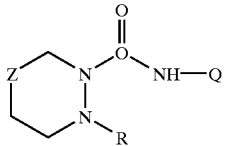

(A')

in which Z, X and Q are as defined above and R is a radical which is different from hydrogen have herbicidal activity. Such compounds should be preparable from perhydro-1-oxa- or perhydro-1-thia-3,4-diazines which are substituted in the 4-position at the nitrogen. It was an object of the present invention to provide oxa- and thiadiazines which are substituted in the 4-position at the nitrogen.

We have found that this object is achieved by a process which allows the preparation of 1-oxa- and 1-thia-3,4-diazines which are substituted in the 4-position at the nitrogen in good yields if the substituent located in the 4-position has the meanings given below for R.

Thus, the present invention relates to N-substituted perhydro-3,4-diazines of the formula I

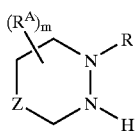

(I)

in which the variables Z, R, m and $R^A$ are as defined below:

Z is O, S, S=O or $SO_2$;

$R^A$ is hydroxyl, $CO_2R^1$, halogen, cyano, $C(O)NR^1{}_2$, $OR^2$, $C_1$–$C_6$-alkyl, $C_1$–$C_6$-haloalkyl, $C_3$–$C_6$-alkenyl, $C_3$–$C_6$-alkynyl, $COR^1$, $S(O)_nR^1$ where n=0, 1 or 2, or $C(O)SR^1$;

R is $CO_2H$, CHO, CN, $C(O)OR^3$, $C(S)OR^3$, $C(O)SR^3$, $C(S)SR^3$, $C(O)NR^4R^5$, $C(S)NR^4R^5$, $C(O)NHCO_2R^6$, $C(O)NHSO_2R^6$, $C(O)NHSO_3R^6$, $C(O)R^2$, $P(O)R^1OR^1$, $P(O)(OR^1)_2$, $S(O)_nR^2$ where n=0, 1, or 2 or $SO_2NHR^1$;

m has the value 0, 1, 2 or 3 and in which the variables $R^1$ to $R^7$ are as defined below:

$R^1$ is hydrogen, $C_1$–$C_6$-alkyl, $C_1$–$C_6$-haloalkyl, $C_1$–$C_3$-alkoxy-$C_1$–$C_3$-alkyl, $C_3$–$C_6$-alkenyl or $C_3$–$C_6$-alkynyl;

$R^2$ is $C_1$–$C_6$-alkyl, $C_3$–$C_6$-cycloalkyl, $C_3$–$C_6$-alkenyl, $C_3$–$C_6$-alkynyl, $C_1$–$C_6$-haloalkyl, $C_1$–$C_6$-alkoxy-$C_1$–$C_6$-alkyl, hydroxycarbonyl-$C_1$–$C_6$-alkyl, $C_1$–$C_6$-alkoxycarbonyl-$C_1$–$C_6$-alkyl, $C_1$–$C_6$-alkylthio-$C_1$–$C_6$-alkyl, $C_1$–$C_6$-alkylsulfinyl-$C_1$–$C_6$-alkyl, $C_1$–$C_6$-alkylsulfonyl-$C_1$–$C_6$-alkyl, $C_3$–$C_6$-cycloalkyl-$C_1$–$C_6$-alkyl, $C_3$–$C_6$-alkenyloxycarbonyl-$C_1$–$C_6$-alkyl, $C_3$–$C_6$-alkynyloxycarbonyl-$C_1$–$C_6$-alkyl, $C_3$–$C_6$-cycloalkoxy-$C_1$–$C_6$-alkyl, $C_3$–$C_6$-alkenyloxy-$C_1$–$C_6$-alkyl, $C_3$–$C_6$-alkynyloxy-$C_1$–$C_6$-alkyl, $C_1$–$C_6$-haloalkoxy-$C_1$–$C_6$-alkyl, $C_3$–$C_6$-haloalkenyloxy-$C_1$–$C_6$-alkyl, $C_3$–$C_6$-haloalkynyloxy-$C_1$–$C_6$-alkyl, $C_3$–$C_6$-cycloalkyl-$C_1$–$C_6$-thioalkyl, $C_3$–$C_6$-alkenylthio-$C_1$–$C_6$-alkyl, $C_3$–$C_6$-alkynylthio-$C_1$–$C_6$-alkyl, cyano-$C_1$–$C_6$-alkyl, $C_3$–$C_6$-halocycloalkyl-$C_1$–$C_6$-alkyl, halo-$C_2$–$C_6$-alkenyl, $C_1$–$C_6$-alkoxy-$C_3$–$C_6$-alkenyl, $C_1$–$C_6$-haloalkoxy-$C_3$–$C_6$-alkenyl, $C_1$–$C_6$-alkylthio-$C_3$–$C_6$-alkenyl, $C_3$–$C_6$-haloalkynyl, $C_1$–$C_6$-alkoxy-$C_3$–$C_6$-alkynyl, $C_1$–$C_6$-haloalkoxy-$C_3$–$C_6$-alkynyl, $C_1$–$C_6$-alkylcarbonyl, $CHR^1COR^7$, $CHR^1P(O)(OR^7)_2$, $P(O)(OR^7)_2$, $CHR^1P(S)(OR^7)_2$, $CHR^1C(O)NR^4R^5$, $CHR^1C(O)NH_2$, is phenyl, pyridyl, benzyl, phenoxy-$C_1$–$C_6$-alkyl, benzyloxy-$C_1$–$C_6$-alkyl, where the phenyl or pyridyl groups of the five last-mentioned substituents may be substituted by halogen, $C_1$–$C_4$-alkyl, $C_1$–$C_4$-alkoxy or $C_1$–$C_4$-haloalkyl, $R^3$ is $C_1$–$C_{15}$-alkyl, $C_3$–$C_8$-cycloalkyl, $C_2$–$C_{10}$-alkenyl, $C_3$–$C_{10}$-alkynyl, $C_1$–$C_6$-haloalkyl, $C_1$–$C_6$-alkoxy-$C_1$–$C_6$-alkyl, $C_1$–$C_6$-alkylthio-$C_1$–$C_6$-alkyl, $C_1$–$C_6$-alkylsulfinyl-$C_1$–$C_6$-alkyl, $C_1$–$C_6$-alkylsulfonyl-$C_1$–$C_6$-alkyl, $C_1$–$C_3$-alkoxy-$C_1$–$C_3$-alkoxy-$C_1$–$C_3$-alkyl, $C_3$–$C_6$-cycloalkyl-$C_1$–$C_6$-alkyl, carboxyl-$C_1$–$C_6$-alkyl, $C_1$–$C_6$-alkoxycarbonyl-$C_1$–$C_6$-alkyl, $C_1$–$C_6$-alkoxycarbonyl-$C_2$–$C_6$-alkenyl, $C_3$–$C_6$-alkenyloxycarbonyl-$C_1$–$C_6$-alkyl, $C_3$–$C_6$-alkynyloxycarbonyl-$C_1$–$C_6$-alkyl, $C_3$–$C_8$-cycloalkoxy-$C_1$–$C_6$-alkyl, $C_3$–$C_6$-alkenyloxy-$C_1$–$C_6$-alkyl, $C_3$–$C_6$-alkynyloxy-$C_1$–$C_6$-alkyl, $C_1$–$C_6$-haloalkoxy-$C_1$–$C_6$-alkyl, $C_3$–$C_6$-haloalkenyloxy-$C_1$–$C_6$-alkyl, $C_3$–$C_6$-haloalkynyloxy-$C_1$–$C_6$-alkyl, $C_3$–$C_6$-cycloalkyl-$C_1$–$C_6$-thioalkyl, $C_3$–$C_6$-alkenylthio-$C_1$–$C_6$-alkyl, $C_3$–$C_6$-alkynylthio-$C_1$–$C_6$-alkyl, cyano-$C_1$–$C_6$-alkyl, $C_3$–$C_6$-halocycloalkyl-$C_1$–$C_6$-alkyl, halo-$C_3$–$C_6$-alkenyl, $C_1$–$C_6$-alkoxy-$C_3$–$C_6$-alkenyl, $C_1$–$C_6$-haloalkoxy-$C_3$–$C_6$-alkenyl, $C_1$–$C_6$-alkylthio-$C_3$–$C_6$-alkenyl, $C_3$–$C_6$-haloalkynyl, $C_1$–$C_6$-alkoxy-$C_3$–$C_6$-alkynyl, $C_1$–$C_6$-haloalkoxy-$C_3$–$C_6$-alkynyl, $C_1$–$C_6$-alkylthio-$C_3$–$C_6$-alkynyl, is $CHR^1COR^7$, $CHR^1P(O)(OR^7)_2$, $P(O)(OR^7)_2$, $CHR^1P(S)(OR^7)_2$, $CHR^1C(O)NR^4R^5$, $CHR^1C(O)NH_2$, phenoxy-$C_1$–$C_6$-alkyl, benzyloxy-$C_1$–$C_6$-alkyl, where the phenyl groups of the two last-mentioned substituents may be substituted by halogen, $C_1$–$C_4$-alkyl, $C_1$–$C_4$-alkoxy or $C_1$–$C_4$-haloalkyl; is phenyl, pyridyl, naphthyl, quinolyl, quinazolyl, quinoxalyl, 1-methylindolyl, 1-methylbenzimidazolyl, 2-methylindazolyl, benzofuranyl, benzothienyl, benzoxazolyl, benzthiazolyl, benzyl, where the 14 last-mentioned substituents may carry, in adjacent positions, a divalent substituent, such as methylenedioxy, difluoromethylenedioxy, chlorofluoromethylenedioxy, dichloromethylenedioxy, or may in each case be mono- to pentasubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, $C_1$–$C_4$-monoalkylamino, $C_1$–$C_4$-dialkylamino, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano;

$R^4$ is hydrogen, $C_1$–$C_6$-alkyl or $C_1$–$C_6$-alkoxy;

$R^5$, $R^6$ independently of one another are hydrogen, $C_1$–$C_6$-alkyl, $C_2$–$C_6$-alkenyl, $C_2$–$C_6$-alkynyl, $C_3$–$C_6$-cycloalkyl, $C_1$–$C_6$-haloalkyl, $C_1$–$C_6$-alkoxy-$C_1$–$C_6$-alkyl, $C_1$–$C_6$-alkoxycarbonyl-$C_1$–$C_6$-alkyl, are $C_1$–$C_6$-alkoxycarbonyl-$C_2$–$C_6$-alkenyl, where the alkenyl chain may additionally carry one to three halogen and/or cyano radicals, are benzyl which, in adjacent positions of the phenyl ring, may carry a divalent substituent, such as methylenedioxy, difluoromethylenedioxy, chlorofluoromethylenedioxy, dichloromethylenedioxy, or which may be mono- to pentasubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano, or $R^4$ and $R^5$ together with the nitrogen atom to which they are attached are a saturated or unsaturated 4- to 7-membered azaheterocycle which, in addition to carbon ring members, may, if desired, contain one of the following members: —O—, —S—, —N=, —NH— or N—($C_1$–$C_6$-alkyl)—;

$R^7$ is hydrogen, $C_1$–$C_6$-alkyl, $C_1$–$C_6$-haloalkyl, $C_1$–$C_3$-alkoxy-$C_1$–$C_3$-alkyl, $C_2$–$C_6$-cyanoalkyl, $C_3$–$C_6$-alkenyl or $C_3$–$C_6$-alkynyl.

The organic molecule moieties mentioned in the definition of R, $R^A$, $R^1$ to $R^7$ and at phenyl, cycloalkyl and heterocyclyl rings are collective terms for individual enumerations of the individual group members. All carbon chains, i.e. all (unsubstituted or substituted) alkyl, alkenyl or alkynyl moieties can be straight-chain or branched.

Halogenated substituents preferably carry one, two, three, four or five identical or different halogen atoms or are perhalogenated.

The term halogen denotes in each case fluorine, bromine, chlorine or iodine, in particular fluorine or chlorine.

Examples of other meanings are:

$C_1$–$C_4$-alkyl: $CH_3$, $C_2H_5$, n-propyl, $CH(CH_3)_2$, n-butyl, $CH(CH_3)$—$C_2H_5$, 2-methylpropyl or $C(CH_3)_3$, in particular $CH_3$, $C_2H_5$ or $CH(CH_3)_2$;

$C_1$–$C_6$-alkyl: $C_1$–$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular $CH_3$, $C_2H_5$, n-propyl, $CH(CH_3)_2$, n-butyl, $C(CH_3)_3$, n-pentyl or n-hexyl;

$C_1$–$C_{15}$-alkyl: $C_1$–$C_6$-alkyl as mentioned above, and also, for example, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 4-ethylpentyl, 1,1-dimethylpentyl, 1,2-dimethylpentyl, 1,3-dimethylpentyl, 1,4-dimethylpentyl, n-octyl, 1-methylheptyl, 2-methylheptyl, 3-methylheptyl, 4-methylheptyl, 5-methylheptyl, 6-methylheptyl, 1-ethylhexyl, 2-ethylhexyl, 3-ethylhexyl, 4-ethylhexyl, 1,1-dimethylhexyl, 1,2-dimethylhexyl, 1,3-dimethylhexyl, 1,4-dimethylhexyl, 1,5-dimethylhexyl, n-nonyl, 1-methyloctyl, 2-methyloctyl, 3-methyloctyl, 4-methyloctyl, 5-methyloctyl, 6-methyloctyl, 7-methyloctyl, 1-ethylheptyl, 2-ethylheptyl, 3-ethylheptyl, 4-ethylheptyl, 5-ethylheptyl, 6-ethylheptyl, 1,1-dimethylheptyl, 1,2-dimethylheptyl, 1,3-dimethylheptyl, 1,4-dimethylheptyl, 1,5-dimethylheptyl, 1,6-dimethylheptyl, n-decyl, 1-methylnonyl, 2-methylnonyl, 3-methylnonyl, 7-methylnonyl, 8-methylnonyl, 1-ethyloctyl, 2-ethyloctyl, 3-ethyloctyl, 4-ethyloctyl, 5-ethyloctyl, 6-ethyloctyl, 7-ethyloctyl, 8-ethyloctyl, 1,1-dimethyloctyl, 1,2-dimethyloctyl, 1,3-dimethyloctyl, 1,4-dimethyloctyl, 1,5-dimethyloctyl, 1,6-dimethyloctyl, 1,7-dimethyloctyl, n-undecyl, 1-methyldecyl, 1-ethylnonyl, 1,1-dimethylnonyl, 1-propyloctyl, 1-butylheptyl, 6-undecyl, n-dodecyl, 1-methylundecyl, 1-ethyldecyl, 1,1-dimethyldecyl, 1-propylnonyl, 1-butyloctyl, 7-dodecyl, n-tridecyl, 1-methyldodecyl, 1-ethylundecyl, 1,1-dimethylundecyl, n-tetradecyl, 1-methyltridecyl, 1-ethyldodecyl, 1,1-dimethyldodecyl, n-pentadecyl, 1-methyltetradecyl, 1-ethyltridecyl, 1,1-dimethyltridecyl in particular $CH_3$, $C_2H_5$, n-propyl, $CH(CH_3)_2$, n-butyl, $C(CH_3)_3$, n-pentyl, n-hexyl, n-heptyl, n-octyl, n-nonyl, n-decyl, n-undecyl, n-dodecyl, n-tridecyl, n-tetradecyl, n-pentadecyl;

$C_1$–$C_4$-haloalkyl: a $C_1$–$C_4$-alkyl radical as mentioned above which is partially or fully substituted by fluorine, chlorine, bromine and/or iodine, i.e., for example, $CH_2F$, $CHF_2$, $CF_3$, $CH_2Cl$, dichloromethyl, trichloromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, $C_2F_5$, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl, in particular $CH_2F$, $CHF_2$, $CF_3$, $CH_2Cl$, 2-fluoroethyl, 2-chloroethyl or 2,2,2-trifluoroethyl;

$C_1$–$C_6$-haloalkyl: $C_1$–$C_6$-alkyl as mentioned above which is partially or fully substituted by fluorine, chlorine, bromine and/or iodine, i.e., for example, one of the radicals mentioned under $C_1$–$C_4$-haloalkyl, or 5-fluoro-1-pentyl, 5-chloro-1-pentyl, 5-bromo-1-pentyl, 5-iodo-1-pentyl, 5,5,5-trichloro-1-pentyl, undecafluoropentyl, 6-fluoro-1-hexyl, 6-chloro-1-hexyl, 6-bromo-1-hexyl, 6-iodo-1-hexyl, 6,6,6-trichloro-1-hexyl or dodecafluorohexyl, in particular chloromethyl, fluoromethyl, difluoromethyl, trifluoromethyl, 2-fluoroethyl, 2-chloroethyl or 2,2,2-trifluoroethyl;

hydroxy-$C_1$–$C_6$-alkyl: for example hydroxymethyl, 2-hydroxyeth-1-yl, 2-hydroxyprop-1-yl, 3-hydroxyprop-1-yl, 1-hydroxyprop-2-yl, 2-hydroxybut-1-yl, 3-hydroxybut-1-yl, 4-hydroxybut-1-yl, 1-hydroxybut-2-yl, 1-hydroxybut-3-yl, 2-hydroxybut-3-yl, 1-hydroxy-2-methylprop-3-yl, 2-hydroxy-2-methylprop-3-yl or 2-hydroxymethylprop-2-yl, in particular 2-hydroxyethyl;

cyano-$C_1$–$C_6$-alkyl: for example cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl or 2-cyanomethylprop-2-yl, in particular cyanomethyl or 2-cyanoethyl;

phenyl-$C_1$–$C_6$-alkyl: for example benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-(phenylmethyl) eth-1-yl, 1-(phenylmethyl)-1-(methyl)eth-1-yl or 1-(phenylmethyl)prop-1-yl, in particular benzyl or 2-phenylethyl;

phenyl-($C_1$–$C_6$-alkyl)carbonyloxy: for example benzylcarbonyloxy, 1-phenylethylcarbonyloxy, 2-phenylethylcarbonyloxy, 1-phenylprop-1-ylcarbonyloxy, 2-phenylprop-1-ylcarbonyloxy, 3-phenylprop-1-ylcarbonyloxy, 1-phenylbut-1-ylcarbonyloxy, 2-phenylbut-1-ylcarbonyloxy, 3-phenylbut-1-ylcarbonyloxy, 4-phenylbut-1-ylcarbonyloxy, 1-phenylbut-2-ylcarbonyloxy, 2-phenylbut-2-ylcarbonyloxy, 3-phenylbut-2-ylcarbonyloxy, 4-phenylbut-2-ylcarbonyloxy, 1-(phenylmethyl)eth-1-ylcarbonyloxy, 1-(phenylmethyl)-1-(methyl)eth-1-ylcarbonyloxy or 1-(phenylmethyl)prop-1-ylcarbonyloxy, in particular benzylcarbonyloxy or 2-phenylethylcarbonyloxy;

phenyl-$C_1$–$C_6$-alkylsulfonyloxy: for example benzylsulfonyloxy, 1-phenylethylsulfonyloxy, 2-phenylethysulfonyloxy, 1-phenylprop-1-ylsulfonyloxy, 2-phenylprop-1-ylsulfonyloxy, 3-phenylprop-1-ylsulfonyloxy, 1-phenylbut-1-ylsulfonyloxy, 2-phenylbut-1-ylsulfonyloxy, 3-phenylbut-1-ylsulfonyloxy, 4-phenylbut-1-ylsulfonyloxy, 1-phenylbut-2-ylsulfonyloxy, 2-phenylbut-2-ylsulfonyloxy, 3-phenylbut-2-ylsulfonyloxy, 4-phenylbut-2-ylsulfonyloxy, 1-(phenylmethyl)eth-1-ylsulfonyloxy, 1-(phenylmethyl)-1-(methyl)eth-1-ylsulfonyloxy or 1-(phenylmethyl)prop-1-ylsulfonyloxy, in particular benzylsulfonyloxy or 2-phenylethylsulfonyloxy;

($C_1$–$C_6$-alkyl)carbonyl: CO—$CH_3$, CO—$C_2H_5$, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, n-hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl, in particular CO—$CH_3$, CO—$C_2H_5$ or CO—$CH(CH_3)_2$;

($C_1$–$C_6$-alkyl)carbonyl-$C_1$–$C_6$-alkyl: ($C_1$–$C_6$-alkyl) which is substituted by ($C_1$–$C_6$-alkyl)carbonyl as mentioned above, i.e., for example, methylcarbonylmethyl;

($C_1$–$C_6$-haloalkyl)carbonyl: a ($C_1$–$C_6$-alkyl)carbonyl radical as mentioned above which is partially or fully substituted by fluorine, chlorine, bromine and/or iodine, i.e., for example, chloroacetyl, dichloroacetyl, trichloroacetyl, fluoroacetyl, difluoroacetyl, trifluoroacetyl, chlorofluoroacetyl, dichlorofluoroacetyl, chlorodifluoroacetyl, 2-fluoroethylcarbonyl, 2-chloroethylcarbonyl, 2-bromoethylcarbonyl, 2-iodoethylcarbonyl, 2,2-difluoroethylcarbonyl, 2,2,2-trifluoroethylcarbonyl, 2-chloro-2-fluoroethylcarbonyl, 2-chloro-2,2-difluoroethylcarbonyl, 2,2-dichloro-2-fluoroethylcarbonyl, 2,2,2-trichloroethylcarbonyl, pentafluoroethylcarbonyl, 2-fluoropropylcarbonyl, 3-fluoropropylcarbonyl, 2,2-difluoropropylcarbonyl, 2,3-difluoropropylcarbonyl, 2-chloropropylcarbonyl, 3-chloropropylcarbonyl, 2,3-dichloropropylcarbonyl, 2-bromopropylcarbonyl, 3-bromopropylcarbonyl, 3,3,3-trifluoropropylcarbonyl, 3,3,3-trichloropropylcarbonyl, 2,2,3,3,3-pentafluoropropylcarbonyl, heptafluoropropylcarbonyl, 1-(fluoromethyl)-2-fluoroethylcarbonyl, 1-(chloromethyl)-2-chloroethylcarbonyl, 1-(bromomethyl)-2-bromoethylcarbonyl, 4-fluorobutylcarbonyl, 4-chlorobutylcarbonyl, 4-bromobutylcarbonyl, nonafluorobutylcarbonyl, (5-fluoro-1-pentyl)carbonyl, (5-chloro-1-pentyl)carbonyl, (5-bromo-1-pentyl) carbonyl, (5-iodo-1-pentyl)carbonyl, (5,5,5-trichloro-1-pentyl)carbonyl, undecafluoropentylcarbonyl, (6-fluoro-1-hexyl)carbonyl, (6-chloro-1-hexyl) carbonyl, (6-bromo-1-hexyl)carbonyl, (6-iodo-1-hexyl)carbonyl, (6,6,6-trichloro-1-hexyl)carbonyl or dodecafluorohexylcarbonyl, in particular trifluoroacetyl;

($C_1$–$C_6$-alkyl)carbonyloxy: acetyloxy, ethylcarbonyloxy, n-propylcarbonyloxy, 1-methylethylcarbonyloxy, n-butylcarbonyloxy, 1-methylpropylcarbonyloxy, 2-methylpropylcarbonyloxy, 1,1-dimethylethylcarbonyloxy, n-pentylcarbonyloxy, 1-methylbutylcarbonyloxy, 2-methylbutylcarbonyloxy, 3-methylbutylcarbonyloxy, 1,1-dimethylpropylcarbonyloxy, 1,2-dimethylpropylcarbonyloxy, 2,2-dimethylpropylcarbonyloxy, 1-ethylpropylcarbonyloxy, n-hexylcarbonyloxy, 1-methylpentylcarbonyloxy, 2-methylpentylcarbonyloxy, 3-methylpentyl-carbonyloxy, 4-methylpentylcarbonyloxy, 1,1-dimethylbutylcarbonyloxy, 1,2-dimethylbutylcarbonyloxy, 1,3-dimethylbutyl-carbonyloxy, 2,2-dimethylbutylcarbonyloxy, 2,3-dimethylbutylcarbonyloxy, 3,3-dimethylbutyl-carbonyloxy, 1-ethylbutylcarbonyloxy, 2-ethylbutylcarbonyloxy, 1,1,2-trimethyl-propylcarbonyloxy, 1,2,2-trimethylpropylcarbonyloxy, 1-ethyl-1-methylpropylcarbonyloxy or 1-ethyl-2-methylpropylcarbonyloxy, in particular acetyloxy;

($C_1$–$C_6$-haloalkyl)carbonyloxy: a ($C_1$–$C_6$-alkyl) carbonyloxy radical as mentioned above which is partially or fully substituted by fluorine, chlorine, bromine and/or iodine, i.e., for example, chloroacetyloxy, dichloroacetyloxy, trichloroacetyloxy, fluoroacetyloxy, difluoroacetyloxy, trifluoroacetyloxy, chlorofluoroacetyloxy, dichlorofluoroacetyloxy, chlorodifluoroacetyloxy, 2-fluoroethylcarbonyloxy, 2-chloroethylcarbonyloxy, 2-bromoethylcarbonyloxy, 2-iodoethylcarbonyloxy, 2,2-difbluoro-ethylcarbonyloxy, 2,2,2-trifluoroethylcarbonyloxy, 2-chloro-2-fluoroethylcarbonyloxy, 2-chloro-2,2-difluoroethylcarbonyloxy, 2,2-dichloro-2-fluoroethylcarbonyloxy, 2,2,2-trichloro-ethylcarbonyloxy, pentafluoroethylcarbonyloxy, 2-fluoropropylcarbonyloxy, 3-fluoropropyl-carbonyloxy, 2,2-difluoropropylcarbonyloxy, 2,3-difluoropropylcarbonyloxy, 2-chloropropyl-carbonyloxy, 3-chloropropylcarbonyloxy, 2,3-dichloropropylcarbonyloxy, 2-bromopropyl-carbonyloxy, 3-bromopropylcarbonyloxy, 3,3,3-trifluoropropylcarbonyloxy, 3,3,3-trichloro-propylcarbonyloxy, 2,2,3,3,3-pentafluoro-propylcarbonyloxy, heptafluoropropylcarbonyloxy, 1-(fluoromethyl)-2-fluoroethylcarbonyloxy, 1-(chloromethyl)-2-chloroethylcarbonyloxy, 1-(bromomethyl)-2-bromoethylcarbonyloxy, 4-fluorobutylcarbonyloxy, 4-chlorobutylcarbonyloxy, 4-bromobutyl or nonafluorobutyl, in particular trifluoroacetoxy;

($C_1$–$C_6$-alkyl)carbonyloxy-$C_1$–$C_6$-alkyl: ($C_1$–$C_6$-alkyl) which is substituted by ($C_1$–$C_6$-alkyl)carbonyloxy as mentioned above, i.e., for example, methylcarbonyloxymethyl, ethylcarbonyloxymethyl, 1-(methylcarbonyloxy)ethyl, 2-(methylcarbonyloxy) ethyl, 2-(ethylcarbonyloxy)ethyl, 3-(methyl-carbonyloxy) propyl, 4-(methoxycarbonyloxy) butyl, 5-(methoxycarbonyloxy)pentyl or 6-(methoxy-carbonyloxy)hexyl;

($C_1$–$C_6$-alkyl)carbonylthio: acetylthio, ethylcarbonylthio, n-propylcarbonylthio, 1-methylethylcarbonylthio, n-butylcarbonylthio, 1-methylpropylcarbonylthio, 2-methylpropylcarbonylthio, 1,1-dimethyl-ethylcarbonylthio, n-pentylcarbonylthio, 1-methylbutylcarbonylthio, 2-methylbutyl-carbonylthio, 3-methylbutylcarbonylthio, 1,1-dimethylpropylcarbonylthio, 1,2-dimethyl-propylcarbonylthio, 2,2-dimethylpropylcarbonylthio, 1-ethylpropylcarbonylthio, n-hexylcarbonylthio, 1-methylpentylcarbonylthio, 2-methylpentyl-carbonylthio, 3-methylpentylcarbonylthio, 4-methylpentylcarbonylthio, 1,1-dimethyl-butylcarbonylthio, 1,2-dimethylbutylcarbonylthio, 1,3-dimethylbutylcarbonylthio, 2,2-dimethyl-butylcarbonylthio, 2,3-dimethylbutylcarbonylthio, 3,3-dimethylbutylcarbonylthio, 1-ethylbutyicarbonylthio, 2-ethylbutylcarbonylthio, 1,1,2-trimethyl-propylcarbonylthio, 1,2,2-trimethylpropyl-carbonylthio, 1-ethyl-1-methylpropylcarbonylthio or 1-ethyl-2-methylpropylcarbonylthio, in particular acetylthio;

($C_1$–$C_6$-haloalkyl)carbonylthio: a ($C_1$–$C_6$-alkyl) carbonylthio radical as mentioned above which is partially or fully substituted by fluorine, chlorine, bromine and/or iodine, i.e., for example, chloroacetylthio, dichloroacetylthio, trichloroacetylthio, fluoroacetylthio, difluoroacetylthio, trifluoroacetylthio, chlorofluoroacetylthio, dichlorofluoroacetylthio, chlorodifluoroacetylthio, 2-fluoroethylcarbonylthio, 2-chloroethylcarbonylthio, 2-bromoethylcarbonylthio, 2-iodoethylcarbonylthio, 2,2-difluoroethyl-carbonylthio, 2,2,2-trifluoroethylcarbonylthio, 2-chloro-2-fluoroethylcarbonylthio, 2-chloro-2,2-difluoroethylcarbonylthio, 2,2-dichloro-2-fluoroethylcarbonylthio, 2,2,2-trichloro-ethylcarbonylthio, pentafluoroethylcarbonylthio, 2-fluoropropylcarbonylthio, 3-fluoropropyl-carbonylthio, 2,2-difluoropropylcarbonylthio, 2,3-difluoropropylcarbonylthio, 2-chloropropyl-carbonylthio, 3-chloropropylcarbonylthio, 2,3-dichloropropylcarbonylthio, 2-bromopropyl-carbonylthio, 3-bromopropylcarbonylthio, 3,3,3-trifluoropropylcarbonylthio, 3,3,3-trichloro-propylcarbonylthio, 2,2,3,3,3-pentafluoro-propylcarbonylthio, heptafluoropropylcarbonylthio, 1-(fluoromethyl)-2-fluoroethylcarbonylthio, 1-(chloromethyl)-2-chloroethylcarbonylthio, 1-(bromomethyl)-2-bromoethylcarbonylthio, 4-fluorobutylcarbonylthio, 4-chlorobutylcarbonylthio, 4-bromobutylthio or nonafluorobutylthio, in particular trifluoroacetylthio;

($C_1$–$C_6$-alkyl)carbamoyloxy: methylcarbamoyloxy, ethylcarbamoyloxy, n-propylcarbamoyloxy, 1-methylethylcarbamoyloxy, n-butylcarbamoyloxy, 1-methylpropylcarbamoyloxy, 2-methylpropyl-carbamoyloxy, 1,1-dimethylethylcarbamoyloxy, n-pentylcarbamoyloxy, 1-methylbutylcarbamoyloxy, 2-methylbutylcarbamoyloxy, 3-methylbutyl-carbamoyloxy, 1,1-dimethylpropylcarbamoyloxy, 1,2-dimethylpropylcarbamoyloxy, 2,2-dimethyl-propylcarbamoyloxy, 1-ethylpropylcarbamoyloxy, n-hexylcarbamoyloxy, 1-methylpentylcarbamoyloxy, 2-methylpentylcarbamoyloxy, 3-methylpentylcarbamoyloxy, 4-methylpentylcarbamoyloxy, 1,1-dimethylbutylcarbamoyloxy, 1,2-dimethylbutylcarbamoyloxy, 1,3-dimethylbutylcarbamoyloxy, 2,2-dimethylbutylcarbamoyloxy, 2,3-dimethylbutylcarbamoyloxy, 3,3-dimethylbutylcarbamoyloxy, 1-ethylbutylcarbamoyloxy, 2-ethylbutylcarbamoyloxy, 1,1,2-trimethylpropylcarbamoyloxy, 1,2,2-trimethylpropylcarbamoyloxy, 1-ethyl-1-methylpropyl-carbamoyloxy or 1-ethyl-2-methylpropylcarbamoyloxy, in particular methylcarbamoyloxy;

($C_1$–$C_6$-haloalkyl)carbamoyloxy: a ($C_1$–$C_6$-alkyl)carbamoyloxy radical as mentioned above which is partially or fully substituted by fluorine, chlorine, bromine and/or iodine, i.e., for example, chloromethylcarbamoyloxy, dichloromethylcarbamoyloxy, trichloromethylcarbamoyloxy, fluoromethylcarbamoyloxy, difluoromethylcarbamoyloxy, trifluoromethylcarbamoyloxy, chlorofluoromethylcarbamoyloxy, dichlorofluoromethylcarbamoyloxy, chlorodifluoromethylcarbamoyloxy, 2-fluoroethylcarbamoyloxy, 2-chloroethylcarbamoyloxy, 2-bromoethylcarbamoyloxy, 2-iodoethylcarbamoyloxy, 2,2-difluoroethylcarbamoyloxy, 2,2,2-trifluoroethylcarbamoyloxy, 2-chloro-2-fluoroethylcarbamoyloxy, 2-chloro-2,2-difluoroethylcarbamoyloxy, 2,2-dichloro-2-fluoroethylcarbamoyloxy, 2,2,2-trichloroethylcarbamoyloxy, pentafluoroethylcarbamoyloxy, 2-fluoropropylcarbamoyloxy, 3-fluoropropylcarbamoyloxy, 2,2-difluoropropylcarbamoyloxy,. 2,3-difluoropropylcarbamoyloxy, 2-chloropropylcarbamoyloxy, 3-chloropropylcarbamoyloxy, 2,3-dichloropropylcarbamoyloxy, 2-bromopropylcarbamoyloxy, 3-bromopropylcarbamoyloxy, 3,3,3-trifluoropropylcarbamoyloxy, 3,3,3-trichloropropylcarbamoyloxy, 2,2,3,3,3-pentafluoropropylcarbamoyloxy, heptafluoropropylcarbamoyloxy, 1-(fluoromethyl)-2-fluoroethylcarbamoyloxy, 1-(chloromethyl)-2-chloroethylcarbamoyloxy, 1-(bromomethyl)-2-bromoethylcarbamoyloxy, 4-fluorobutylcarbamoyloxy, 4-chlorobutylcarbamoyloxy, 4-bromobutylcarbamoyloxy or nonafluorobutylcarbamoyloxy, in particular trifluoromethylcarbamoyloxy;

$C_1$–$C_6$-alkoxy: for example $OCH_3$, $OC_2H_5$, $OCH_2$—$C_2H_5$, $OCH(CH_3)_2$, n-butoxy, $OCH(CH_3)$—$C_2H_5$, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 2-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy, in particular $OCH_3$, $OC_2H_5$ or $OCH(CH_3)_2$;

$C_1$–$C_4$-haloalkoxy: a $C_1$–$C_4$-alkoxy radical as mentioned above which is partially or fully substituted by fluorine, chlorine, bromine and/or iodine, i.e., for example, chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy, in particular 2-chloroethoxy or 2,2,2-trifluoroethoxy;

$C_1$–$C_6$-haloalkoxy: a $C_1$–$C_6$-alkoxy radical as mentioned above which is partially or fully substituted by fluorine, chlorine, bromine and/or iodine, i.e., for example, one of the radicals mentioned under $C_1$–$C_4$-haloalkoxy, or 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy or dodecafluorohexoxy, in particular chloromethoxy, fluoromethoxy, difluoromethoxy, trifluoromethoxy, 2-fluoroethoxy, 2-chloroethoxy or 2,2,2-trifluoroethoxy;

hydroxy-$C_1$–$C_6$-alkoxy: for example $OCH_2$—OH, $OCH(CH_3)$—OH, $OCH_2$—$CH_2$—OH, $OCH(C_2H_5)$—OH, $OCH_2$—$CH(CH_3)$—OH, 3-hydroxyprop-1-yloxy, 1-hydroxybut-1-yloxy, 2-hydroxybut-1-yloxy, 3-hydroxybut-1-yloxy, 4-hydroxybut-1-yloxy, 1-hydroxybut-2-yloxy, 2-hydroxybut-2-yloxy, 3-hydroxybut-2-yloxy, 4-hydroxybut-2-yloxy, 1-($CH_2$—OH)-eth-1-yloxy, 1-($CH_2$—OH)-1-($CH_3$)-eth-1-yloxy or 1-($CH_2$—OH)-prop-1-yloxy, in particular $OCH_2$—OH or $OCH_2$—$CH_2$—OH;

cyano-$C_1$–$C_6$-alkoxy: for example $OCH_2$—CN, $OCH(CH_3)$—CN, $OCH_2$—$CH_2$—CN, $OCH(C_2H_5)$—OH, $OCH_2$—$CH(CH_3)$—CN, 3-cyanoprop-1-yloxy, 1-cyanobut-1-yloxy, 2-cyanobut-1-yloxy, 3-cyanobut-1-yloxy, 4-cyanobut-1-yloxy, 1-cyanobut-2-yloxy, 2-cyanobut-2-yloxy, 3-cyanobut-2-yloxy, 4-cyanobut-2-yloxy, 1-($CH_2$—CN)-eth-1-yloxy, 1-($CH_2$—CN)-1-($CH_3$)-eth-1-yloxy or 1-($CH_2$—CN)-prop-1-yloxy, in particular $OCH_2$—CN or $OCH_2$—$CH_2$—CN;

phenyl-$C_1$–$C_6$-alkoxy: for example benzyloxy, 1-phenylethoxy, 2-phenylethoxy, 1-phenylprop-1-yloxy, 2-phenylprop-1-yloxy, 3-phenylprop-1-yloxy, 1-phenylbut-1-yloxy, 2-phenylbut-1-yloxy, 3-phenylbut-1-yloxy, 4-phenylbut-1-yloxy, 1-phenylbut-2-yloxy, 2-phenylbut-2-yloxy, 3-phenylbut-2-yloxy, 4-phenylbut-2-yloxy, 1-(benzyl)eth-1-yloxy, 1-(benzyl)-1-(methyl)eth-1-yloxy or 1-(benzyl)prop-1-yloxy, in particular benzyloxy or 2-phenylethoxy;

phenyl-$C_1$–$C_6$-alkylthio: for example benzylthio, 1-phenylethylthio, 2-phenylethylthio, 1-phenylprop-1-ylthio, 2-phenylprop-1-ylthio, 3-phenylprop-1-ylthio, 1-phenylbut-1-ylthio, 2-phenylbut-1-ylthio, 3-phenylbut-1-ylthio, 4-phenylbut-1-ylthio, 1-phenylbut-2-ylthio, 2-phenylbut-2-ylthio, 3-phenylbut-2-ylthio, 4-phenylbut-2-ylthio, 1-(phenylmethyl)eth-1-ylthio, 1-(phenylmethyl)-1-(methyl)eth-1-ylthio or 1-(phenylmethyl)prop-1-ylthio, in particular benzylthio or 2-phenylethylthio;

($C_1$–$C_6$-alkoxy)carbonyl: for example CO—$OCH_3$, CO—$OC_2H_5$, CO—$CH_2$—$C_2H_5$, CO—$OCH(CH_3)_2$, n-butoxycarbonyl, CO—$OCH(CH_3)$—$C_2H_5$, CO—$OCH_2$—$CH(CH_3)_2$, CO—$OC(CH_3)_3$, n-pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl, in particular CO—$OCH_3$, CO—$OC_2H_5$, CO—$OCH(CH_3)_2$ or CO—$CH_2$—CH$(CH_3)_2$;

($C_1$–$C_6$-alkoxy)carbonyloxy: methoxycarbonyloxy, ethoxycarbonyloxy, n-propoxycarbonyloxy, 1-methylethoxycarbonyloxy, n-butoxycarbonyloxy, 1-methylpropoxycarbonyloxy, 2-methylpropoxycarbonyloxy, 1,1-dimethylethoxycarbonyloxy, n-pentoxycarbonyloxy, 1-methylbutoxycarbonyloxy, 2-methylbutoxycarbonyloxy, 3-methylbutoxycarbonyloxy, 2,2-dimethylpropoxycarbonyloxy, 1-ethylpropoxycarbonyloxy, n-hexoxycarbonyloxy, 1,1-dimethylpropoxycarbonyloxy, 1,2-dimethylpropoxycarbonyloxy, 1-methylpentoxycarbonyloxy, 2-methylpentoxycarbonyloxy, 3-methylpentoxycarbonyloxy, 4-methylpentoxycarbonyloxy, 1,1-dimethylbutoxycarbonyloxy, 1,2-dimethylbutoxycarbonyloxy, 1,3-dimethylbutoxycarbonyloxy, 2,2-dimethylbutoxycarbonyloxy, 2,3-dimethylbutoxycarbonyloxy, 3,3-dimethylbutoxycarbonyloxy, 1-ethylbutoxycarbonyloxy, 2-ethylbutoxycarbonyloxy, 1,1,2-trimethylpropoxycarbonyloxy, 1,2,2-trimethylpropoxycarbonyloxy, 1-ethyl-1-methylpropoxycarbonyloxy or 1-ethyl-2-methylpropoxycarbonyloxy, in particular methoxycarbonyloxy, ethoxycarbonyloxy or 1-methylethoxycarbonyloxy;

($C_1$–$C_6$-alkoxy)carbonylthio: methoxycarbonylthio, ethoxycarbonylthio, n-propoxycarbonylthio, 1-methylethoxycarbonylthio, n-butoxycarbonylthio, 1-methylpropoxycarbonylthio, 2-methylpropoxycarbonylthio, 1,1-dimethylethoxycarbonylthio, n-pentoxycarbonylthio, 1-methylbutoxycarbonylthio, 2-methylbutoxycarbonylthio, 3-methylbutoxycarbonylthio, 2,2-dimethylpropoxycarbonylthio, 1-ethylpropoxycarbonylthio, n-hexoxycarbonylthio, 1,1-dimethylpropoxycarbonylthio, 1,2-dimethylpropoxycarbonylthio, 1-methylpentoxycarbonylthio, 2-methylpentoxycarbonylthio, 3-methylpentoxycarbonylthio, 4-methylpentoxycarbonylthio, 1,1-dimethylbutoxycarbonylthio, 1,2-dimethylbutoxycarbonylthio, 1,3-dimethylbutoxycarbonylthio, 2,2-dimethylbutoxycarbonylthio, 2,3-dimethylbutoxycarbonylthio, 3,3-dimethylbutoxycarbonylthio, 1-ethylbutoxycarbonylthio, 2-ethylbutoxycarbonylthio, 1,1,2-trimethylpropoxycarbonylthio, 1,2,2-trimethylpropoxycarbonylthio, 1-ethyl-1-methylpropoxycarbonylthio or 1-ethyl-2-methylpropoxycarbonylthio, in particular methoxycarbonylthio, ethoxycarbonylthio or 1-methylethoxycarbonylthio;

$C_1$–$C_6$-alkylthio: $SCH_3$, $SC_2H_5$, $SCH_2$—$C_2H_5$, SCH$(CH_3)_2$, n-butylthio, 1-methylpropylthio, 2-methylpropylthio, SC$(CH_3)_3$, n-pentylthio, 1-methylbutylthio, 2-methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio, in particular $SCH_3$ or $SC_2H_5$;

$C_1$–$C_6$-haloalkylthio: $C_1$–$C_6$-alkylthio as mentioned above, which is partially or fully substituted by fluorine, chlorine, bromine and/or iodine, i.e., for example, $SCHF_2$, $SCF_3$, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, $SC_2F_5$, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio, nonafluorobutylthio, 5-fluoropentylthio, 5-chloropentylthio, 5-bromopentylthio, 5-iodopentylthio, undecafluoropentylthio, 6-fluorohexylthio or 6-chlorohexylthio, in particular $SCH_2F$, $SCHF_2$, $SCF_3$, $SCH_2Cl$, 2-fluoroethylthio, 2-chloroethylthio or 2,2,2-trifluoroethylthio;

$C_1$–$C_6$-alkylsulfinyl: SO—$CH_3$, SO—$C_2H_5$, n-propylsulfinyl, 1-methylethylsulfinyl, n-butylsulfinyl, 1-methylpropylsulfinyl, 2-methylpropylsulfinyl, 1,1-dimethylethylsulfinyl, n-pentylsulfinyl, 1-methylbutylsulfinyl, 2-methylbutylsulfinyl, 3-methylbutylsulfinyl, 1,1- dimethylpropylsulfinyl, 1,2-dimethylpropylsulfinyl, 2,2-dimethylpropylsulfinyl, 1-ethylpropylsulfinyl, n-hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl, in particular SO—CH$_3$;

$C_1$–$C_6$-alkylsulfonyl: SO$_2$—CH$_3$, SO$_2$—C$_2$H$_5$, n-propylsulfonyl, SO$_2$—CH(CH$_3$)$_2$, n-butylsulfonyl, 1-methylpropylsulfonyl, 2-methylpropylsulfonyl, SO$_2$—C(CH$_3$)$_3$, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfbnyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl, in particular SO$_2$—CH$_3$;

$C_1$–$C_6$-alkylsulfonyloxy: O—SO$_2$—CH$_3$, O—SO$_2$—C$_2$H$_5$, n-propylsulfonyloxy, O—SO$_2$—CH(CH$_3$)$_2$, n-butylsulfonyloxy, 1-methylpropylsulfonyloxy, 2-methylpropylsulfonyloxy, O—SO$_2$—C(CH$_3$)$_3$, n-pentylsulfonyloxy, 1-methylbutylsulfonyloxy, 2-methylbutylsulfonyloxy, 3-methylbutylsulfonyloxy, 1,1-dimethylpropylsulfonyloxy, 1,2-dimethylpropylsulfonyloxy, 2,2-dimethylpropylsulfonyloxy, 1-ethylpropylsulfonyloxy,. n-hexylsulfonyloxy, 1-methylpentylsulfonyloxy, 2-methylpentylsulfonyloxy, 3-methylpentylsulfonyloxy, 4-methylpentylsulfonyloxy, 1,1-dimethylbutylsulfonyloxy, 1,2-dimethylbutylsulfonyloxy, 1,3-dimethylbutylsulfonyloxy, 2,2-dimethylbutylsulfonyloxy, 2,3-dimethylbutylsulfonyloxy, 3,3-dimethylbutylsulfonyloxy, 1-ethylbutylsulfonyloxy, 2-ethylbutylsulfonyloxy, 1,1,2-trimethylpropylsulfonyloxy, 1,2,2-trimethylpropylsulfonyloxy, 1-ethyl-1-methylpropylsulfonyloxy or 1-ethyl-2-methylpropylsulfonyloxy, in particular methylsulfonyloxy;

$C_1$–$C_6$-haloalkylsulfonyloxy: $C_1$–$C_6$-alkylsulfonyloxy as mentioned above which is partially or fully substituted by fluorine, chlorine, bromine and/or iodine, i.e., for example, ClCH$_2$—SO$_2$—O—, CH(Cl)$_2$—SO$_2$—O—, C(Cl)$_3$—SO$_2$—O—, FCH$_2$—SO$_2$—O—, CHF$_2$—SO$_2$—O—, CF$_3$—SO$_2$—O—, chlorofluoromethyl-SO$_2$—O—, dichlorofluoromethyl-SO$_2$—O—, chlorodifluoromethyl-SO$_2$—O—, 1-fluoroethyl-SO$_2$—O—, 2-fluoroethyl-SO$_2$—O—, 2-chloroethyl-SO$_2$—O—, 2-bromoethyl-SO$_2$—O—, 2-iodoethyl-SO$_2$—O—, 2,2-difluoroethyl-SO$_2$—O—, 2,2,2-trifluoroethyl-SO$_2$—O—, 2-chloro-2-fluoroethyl-SO$_2$—O—, 2-chloro-2,2-difluoroethyl-SO$_2$—O—, 2,2-dichloro-2-fluoroethyl-SO$_2$—O—, 2,2,2-trichloroethyl-SO$_2$—O—, C$_2$F$_5$—SO$_2$—O—, 2-fluoropropyl-SO$_2$—O—, 3-fluoropropyl-SO$_2$—O—, 2,2-difluoropropyl-SO$_2$—O—, 2,3-difluoropropyl-SO$_2$—O—, 2-chloropropyl-SO$_2$—O—, 3-chloropropyl-SO$_2$—O—, 2,3-dichloropropyl-SO$_2$—O—, 2-bromopropyl-SO$_2$—O—, 3-bromopropyl-SO$_2$—O—, 3,3,3-trifluoropropyl-SO$_2$—O—, 3,3,3-trichloropropyl-SO$_2$—O—, 2,2,3,3,3-pentafluoropropyl-SO$_2$—O—, C$_2$F$_5$—CF$_2$—SO$_2$—O—, 1-(fluoromethyl)-2-fluoroethyl-SO$_2$—O—, 1-(chloromethyl)-2-chloroethyl-SO$_2$—O—, 1-(bromomethyl)-2-bromoethyl-SO$_2$—O—, 4-fluorobutyl-SO$_2$—O—, 4-chlorobutyl-SO$_2$—O—, 4-bromobutyl-SO$_2$—O—, C$_2$F$_5$—CF$_2$—CF$_2$—SO$_2$—O—, 5-fluoropentyl-SO$_2$—O—, 5-chloropentyl-SO$_2$—O—, 5-bromopentyl-SO$_2$—O—, 5-iodopentyl-SO$_2$—O—, 5,5,5-trichloropentyl-SO$_2$—O—, C$_2$F$_5$—CF$_2$—CF$_2$—CF$_2$—SO$_2$—O—, 6-fluorohexyl-SO$_2$—O—, 6-chlorohexyl-SO$_2$—O—, 6-bromohexyl-SO$_2$—O—, 6-iodohexyl-SO$_2$—O—, 6,6,6-trichlorohexyl-SO$_2$—O—or dodecafluorohexyl-SO$_2$—O—, in particular CF$_3$—SO$_2$—O—;

($C_1$–$C_6$-alkyl)aminocarbonyl: ($C_1$–$C_4$-alkyl)aminocarbonyl as mentioned above and also for example, n-pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, n-hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl or 1-ethyl-2-methylpropylaminocarbonyl, in particular CO—NH-CH$_3$, CO—NH—C$_2$H$_5$ or CO—NH—CH(CH$_3$)$_2$;

di($C_1$–$C_6$-alkyl)aminocarbonyl: for example N,N-dimethylaminocarbonyl, N,N-diethylaminocarbonyl, N,N-dipropylaminocarbonyl, N,N-di(1-methylethyl)aminocarbonyl, N,N-dibutylaminocarbonyl, N,N-di(1-methylpropyl)aminocarbonyl, N,N-di(2-methylpropyl)aminocarbonyl, N,N-di(1,1-dimethylethyl)

aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl or N-(1,1-dimethylethyl)-N-(2-methylpropyl)aminocarbonyl, in particular N,N-dimethylaminocarbonyl or N,N-diethylaminocarbonyl;

($C_1$–$C_6$-alkyl)iminooxycarbonyl: methyliminooxycarbonyl, ethyliminooxycarbonyl, n-propyliminooxycarbonyl, 1-methylethyliminooxycarbonyl, n-butyliminooxycarbonyl, 1-methylpropyliminooxycarbonyl, 2-methylpropyliminooxycarbonyl, 1,1-dimethylethyliminooxycarbonyl, n-pentyliminooxycarbonyl, 1-methylbutyliminooxycarbonyl, 2-methylbutyliminooxycarbonyl, 3-methylbutyliminooxycarbonyl, 1,1-dimethylpropyliminooxycarbonyl, 1,2-dimethylpropyliminooxycarbonyl, 2,2-dimethylpropyliminooxycarbonyl, 1-ethylpropyliminooxycarbonyl, n-hexyliminooxycarbonyl, 1-methylpentyliminooxycarbonyl, 2-methylpentyliminooxycarbonyl, 3-methylpentyliminooxycarbonyl, 4-methylpentyliminooxycarbonyl, 1,1-dimethylbutyliminooxycarbonyl, 1,2-dimethylbutyliminooxycarbonyl, 1,3-dimethylbutyliminooxycarbonyl, 2,2-dimethylbutyliminooxycarbonyl, 2,3-dimethylbutyliminooxycarbonyl, 3,3-dimethylbutyliminooxycarbonyl, 1-ethylbutyliminooxycarbonyl, 2-ethylbutyliminooxycarbonyl, 1,1,2-trimethylpropyliminooxycarbonyl, 1,2,2-trimethylpropyliminooxycarbonyl, 1-ethyl-1-methylpropyliminooxycarbonyl or 1-ethyl-2-methylpropyliminooxycarbonyl, in particular methyliminooxycarbonyl, ethyliminooxycarbonyl or 1-methylethyliminooxycarbonyl;

$C_1$–$C_6$-alkylideneaminoxy: acetylideneaminoxy, 1-propylideneaminoxy, 2-propylideneaminoxy, 1-butylideneaminoxy, 2-butylideneaminoxy or 2-hexylideneaminoxy, in particular acetylideneaminoxy or 2-propylideneaminoxy;

$C_1$–$C_6$-alkyliminooxy: methyliminooxy, ethyliminooxy, n-propyliminooxy, 1-methylethyliminooxy, n-butyliminooxy, 1-methylpropyliminooxy, 2-methylpropyliminooxy, n-pentyliminooxy, n-hexyliminooxy, 1-methylpentyliminooxy, 2-methylpentyliminooxy, 3-methylpentyliminooxy or 4-methylpentyliminooxy, in particular methyliminooxy, ethyliminooxy or 1-methylethyliminooxy;

$C_1$–$C_6$-alkoxy-($C_1$–$C_6$-alkyl)aminocarbonyl: ($C_1$–$C_6$-alkyl)aminocarbonyl such as CO—NH—$CH_3$, CO—NH—$C_2H_5$, CO—NH—$CH_2$—$C_2H_5$, CO—NH—CH($CH_3$)$_2$, CO—NH—($CH_2$)$_3$—$CH_3$, CO—NH—CH($CH_3$)—$C_2H_5$, CO—NH—$CH_2$—CH($CH_3$)$_2$, CO—NH—C($CH_3$)$_3$, CO—NH—($CH_2$)$_4$—$CH_3$, 1-methylbutylaminocarbonyl, 2-methylbutylaminocarbonyl, 3-methylbutyl-aminocarbonyl, 2,2-dimethylpropylaminocarbonyl, 1-ethylpropylaminocarbonyl, n-hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl and 1-ethyl-2-methylpropylaminocarbonyl, preferably ($C_1$–$C_4$-alkyl)aminocarbonyl, which is substituted by $C_1$–$C_6$-alkoxy as mentioned above, i.e., for example, CO—NH—$CH_2$—$OCH_3$ or CO—NH—$CH_2$—$OC_2H_5$; $C_1$–$C_6$-alkoxyamino-$C_1$–$C_6$-alkyl: for example $CH_2$—NH—$OCH_3$, $CH_2$—NH—$OC_2H_5$, $CH_2$—NH—$OCH_2$—$C_2H_5$, $CH_2$—NH—OCH($CH_3$)$_2$, $CH_2$—NH—$OCH_2$—$CH_2$—$C_2H_5$, $CH_2$—NH—OCH($CH_3$)—$C_2H_5$, $CH_2$—NH—$OCH_2$—CH($CH_3$)$_2$, $CH_2$—NH—OC($CH_3$)$_3$, $CH_2$—NH—$OCH_2$—($CH_2$)$_3$—$CH_3$, (1-methylbutoxyamino)methyl, (2-methylbutoxyamino)methyl, (3-methylbutoxyamino)methyl, (2,2-dimethylpropoxyamino)methyl, (1-ethylpropoxyamino)methyl, n-hexoxyamino-methyl, (1,1-dimethylpropoxyamino)methyl, (1,2-dimethylpropoxyamino)methyl, (1-methylpentoxyamino)m ethyl, (2-methylpentoxyamino)methyl, (3-methylpentoxyamino)methyl, (4-methylpentoxyamino)methyl, (1,1-dimethylbutoxyamino)methyl, (1,2-dimethylbutoxyamino)methyl, (1,3-dimethylbutoxyamino)methyl, (2,2-dimethylbutoxyamino)methyl, (2,3-dimethylbutoxyamino)methyl, (3,3-dimethylbutoxyamino)methyl, (1-ethylbutoxyamino)methyl, (2-ethylbutoxyamino)methyl, (1,1,2-trimethylpropoxyamino)methyl, (1,2,2-trimethylpropoxyamino)methyl, (1-ethyl-1-methylpropoxyamino)methyl, (1-ethyl-2-methylpropoxyamino)methyl, methoxyaminoethyl, ethoxyaminoethyl, n-propoxyaminoethyl, (1-methylethoxyamino)ethyl, n-butoxyaminoethyl, (1-methylpropoxyamino)ethyl, (2-methylpropoxyamino)ethyl, (1,1-dimethylethoxyamino)ethyl, n-pentoxyaminoethyl, (1-methylbutoxyamino)ethyl, (2-methylbutoxyamino)ethyl, (3-methylbutoxyamino)ethyl, (2,2-dimethylpropoxyamino)ethyl, (1-ethylpropoxyamino)ethyl, n-hexoxyaminoethyl, (1,1-dimethylpropoxyamino)ethyl, (1,2-dimethylpropoxyamino)ethyl, (1-methylpentoxyamino)ethyl, (2-methylpentoxyamino)ethyl, (3-methylpentoxyamino)ethyl, (4-methylpentoxyamino)ethyl, (1,1-dimethylbutoxyamino)ethyl, (1,2-dimethylbutoxyamino)ethyl, (1,3-dimethylbutoxyamino)ethyl, (2,2-dimethylbutoxyamino)ethyl, (2,3-dimethylbutoxyamino)ethyl, (3,3-dimethylbutoxyamino)ethyl, (1-ethylbutoxyamino)ethyl, (2-ethylbutoxyamino)ethyl, (1,1,2-trimethylpropoxyamino)ethyl, (1,2,2-trimethylpropoxyamino)ethyl, (1-ethyl-1-methylpropoxyamino)ethyl, (1-ethyl-2-methylpropoxyamino)ethyl 2-(methoxyamino)propyl, 3-(methoxyamino)propyl or 2-(ethoxyamino)propyl, preferably $C_1$–$C_6$-alkoxyamino-$C_1$–$C_2$-alkyl;

$C_1$–$C_6$-alkoxy-$C_1$–$C_6$-alkylamino-$C_1$–$C_6$-alkyl: $C_1$–$C_6$-alkylamino-$C_1$–$C_6$-alkyl such as $CH_2$—NH—$CH_3$, $CH_2$—NH—$C_2H_5$, $CH_2$—NH—$CH_2$—$C_2H_5$, $CH2$—NH—$CH(CH_3)_2$, $CH_2$—NH—$(CH_2)_3$—$CH_3$, $CH_2$—NH—$CH(CH_3)$—$C_2H_5$, $CH_2$—NH—$CH_2$—CH$(CH_3)_2$, $CH_2$—NH—$C(CH_3)_3$, $CH_2$—NH—$(CH_2)_4$—$CH_3$, (1-methylbutylamino)methyl, (2-methylbutylamino)methyl, (3-methylbutylamino)methyl, (2,2-dimethylpropylamino)methyl, (1-ethylpropylamino)methyl, n-hexylamino-methyl, (1,1-dimethylpropylamino)methyl, (1,2-dimethylpropylamino)methyl, (1-methylpentylamino)methyl, (2-methylpentylamino)methyl, (3-methylpentylamino)methyl, (4-methylpentylamino)methyl, (1,1-dimethylbutylamino)methyl, (1,2-dimethylbutylamino)methyl, (1,3-dimethylbutylamino)methyl, (2,2-dimethylbutylamino)methyl, (2,3-dimethylbutylamino)methyl, (3,3-dimethylbutylamino)methyl, (1-ethylbutylamino)methyl, (2-ethylbutylamino)methyl, (1,1,2-trimethylpropylamino)methyl, (1,2,2-trimethylpropylamino)methyl, (1-ethyl-1-methylpropylamino)methyl, (1-ethyl-2-methylpropylamino)methyl, methylaminoethyl, ethylaminoethyl, n-propylaminoethyl, (1-methylethylamino)ethyl, n-butylaminoethyl, (1-methylpropylamino)ethyl, (2-methylpropylamino)ethyl, (1,1-dimethylethylamino)ethyl, n-pentylaminoethyl, (1-methylbutylamino)ethyl, (2-methylbutylamino)ethyl, (3-methylbutylamino)ethyl, (2,2-dimethylpropylamino)ethyl, (1-ethylpropylamino)ethyl, n-hexylaminoethyl, (1,1-dimethylpropylamino)ethyl, (1,2-dimethylpropylamino)ethyl, (1-methylpentylamino)ethyl, (2-methylpentylamino)ethyl, (3-methylpentylamino)ethyl, (4-methylpentylamino)ethyl, (1,1-dimethylbutylamino)ethyl, (1,2-dimethylbutylamino)ethyl, (1,3-dimethylbutylamino)ethyl, (2,2-dimethylbutylamino)ethyl, (2,3-dimethylbutylamino)ethyl, (3,3-dimethylbutylamino)ethyl, (1-ethylbutylamino)ethyl, (2-ethylbutylamino)ethyl, (1,1,2-trimethylpropylamino)ethyl, (1,2,2-trimethylpropylamino)ethyl, (1-ethyl-1-methylpropylamino)ethyl, (1-ethyl-2-methylpropylamino)ethyl, 2-(methylamino)propyl, 3-(methylamino)propyl and 2-(ethylamino)propyl, preferably $C_1$–$C_6$-alkylamino-$C_1$–$C_2$-alkyl, which is substituted by $C_1$–$C_6$-alkoxy as mentioned above, i.e., for example, $CH_2$—NH—$CH_2$—$OCH_3$ or $CH_2$—NH—$CH_2$—$OC_2H_5$;

$C_1$–$C_6$-alkyloximino-$C_1$–$C_6$-alkyl: $C_1$–$C_6$-alkyl which is substituted by $C_1$–$C_6$-alkyloximino such as methoxyimino, ethoxyimino, 1-propoxyimino, 2-propoxyimino, 1-methylethoxyimino, n-butoxyimino, sec-butoxyimino, tert-butoxyimino, 1-methyl-1-propoxyimino, 2-methyl-1-propoxyimino, 1-methyl-2-propoxyimino, 2-methyl-2-propoxyimino, n-pentoxyimino, 2-pentoxyimino, 3-pentoxyimino, 4-pentoxyimino, 1-methyl-1-butoxyimino, 2-methyl-1-butoxyimino, 3-methyl-1-butoxyimino, 1-methyl-2-butoxyimino, 2-methyl-2-butoxyimino, 3-methyl-2-butoxyimino, 1-methyl-3-butoxyimino, 2-methyl-3-butoxyimino, 3-methyl-3-butoxyimino, 1,1-dimethyl-2-propoxyimino, 1,2-dimethyl-1-propoxyimino, 1,2-dimethyl-2-propoxyimino, 1-ethyl-1-propoxyimino, 1-ethyl-2-propoxyimino, n-hexoxyimino, 2-hexoxyimino, 3-hexoxyimino, 4-hexoxyimino, 5-hexoxyimino, 1-methyl-1-pentoxyimino, 2-methyl-1-pentoxyimino, 3-methyl-1-pentoxyimino, 4-methyl-1-pentoxyimino, 1-methyl-2-pentoxyimino, 2-methyl-2-pentoxyimino, 3-methyl-2-pentoxyimino, 4-methyl-2-pentoxyimino, 1-methyl-3-pentoxyimino, 2-methyl-3-pentoxyimino, 3-methyl-3-pentoxyimino, 4-methyl-3-pentoxyimino, 1-methyl-4-pentoxyimino, 2-methyl-4-pentoxyimino, 3-methyl-4-pentoxyimino, 4-methyl-4-pentoxyimino, 1,1-dimethyl-2-butoxyimino, 1,1-dimethyl-3-butoxyimino, 1,2-dimethyl-1-butoxyimino, 1,2-dimethyl-2-butoxyimino, 1,2-dimethyl-3-butoxyimino, 1,3-dimethyl-1-butoxyimino, 1,3-dimethyl-2-butoxyimino, 1,3-dimethyl-3-butoxyimino, 2,2-dimethyl-3-butoxyimino, 2,3-dimethyl-1-butoxyimino, 2,3-dimethyl-2-butoxyimino, 2,3-dimethyl-3-butoxyimino, 3,3-dimethyl-1-butoxyimino, 3,3-dimethyl-2-butoxyimino, 1-ethyl-1-butoxyimino, 1-ethyl-2-butoxyimino, 1-ethyl-3-butoxyimino, 2-ethyl-1-butoxyimino, 2-ethyl-2-butoxyimino, 2-ethyl-3-butoxyimino, 1,1,2-trimethyl-2-propoxyimino, 1-ethyl-1-methyl-2-propoxyimino, 1-ethyl-2-methyl-1-propoxyimino and 1-ethyl-2-methyl-2-propoxyimino, i.e., for example, methoxyiminomethyl;

$C_1$–$C_6$-alkoxy-$C_1$–$C_6$-alkyl: $C_1$–$C_6$-alkyl which is substituted by $C_1$–$C_6$-alkoxy as mentioned above, i.e., for example, $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, in particular $CH_2$—$OCH_3$ or 2-methoxyethyl;

di($C_1$–$C_6$-alkoxy)—$C_1$–$C_6$-alkyl: for example 2,2-dimethoxyethyl or 2,2-diethoxyethyl;

$C_1$–$C_6$-alkoxy-$C_1$–$C_6$-alkoxy: $C_1$–$C_6$-alkoxy which is substituted by $C_1$–$C_6$-alkoxy as mentioned above, i.e., for example, $OCH_2$—$OCH_3$, $OCH_2$—$OC_2H_5$, n-propoxymethoxy, $OCH_2$—$OCH(CH_3)_2$, n-butoxymethoxy, (1-methylpropoxy)methoxy, (2-methylpropoxy)methoxy, $OCH_2$—$OC(CH_3)_3$, 2-(methoxy)ethoxy, 2-(ethoxy)ethoxy, 2-(n-propoxy)ethoxy, 2-(1-methylethoxy)ethoxy, 2-(n-butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(n-propoxy)propoxy,. 2-(1-methylethoxy)propoxy, 2-(n-butoxy)propoxy, 2-(1-methylpropoxy)propoxy, 2-(2-methylpropoxy)propoxy, 2-(1,1-dimethylethoxy)propoxy, 3-(methoxy)propoxy, 3-(ethoxy)propoxy, 3-(n-propoxy)propoxy, 3-(1-methylethoxy)propoxy, 3-(n-butoxy)propoxy, 3-(1-methylpropoxy)propoxy, 3-(2-methylpropoxy)propoxy, 3-(1,1-dimethylethoxy)propoxy, 2-(methoxy)butoxy, 2-(ethoxy)butoxy, 2-(n-propoxy)butoxy, 2-(1-methylethoxy)butoxy, 2-(n-butoxy)butoxy, 2-(1-methylpropoxy)butoxy, 2-(2-methylpropoxy)butoxy, 2-(1,1-dimethylethoxy)butoxy, 3-(methoxy)butoxy, 3-(ethoxy)butoxy, 3-(n-propoxy)butoxy, 3-(1-methylethoxy)butoxy, 3-(n-butoxy)butoxy, 3-(1-methylpropoxy)butoxy, 3-(2-methylpropoxy)butoxy, 3-(1,1-dimethylethoxy)butoxy, 4-(methoxy)butoxy, 4-(ethoxy)butoxy, 4-(n-propoxy)butoxy, 4-(1-methylethoxy)butoxy, 4-(n-butoxy)butoxy, 4-(1-methylpropoxy)butoxy, 4-(2-methylpropoxy)butoxy, 4-(1,1-dimethylethoxy)butoxy, 5-(methoxy)pentoxy, 5-(ethoxy)pentoxy, 5-(n-propoxy)pentoxy, 5-(1-methylethoxy)pentoxy, 5-(n-butoxy)pentoxy, 5-(1-methylpropoxy)pentoxy, 5-(2-methylpropoxy)pentoxy, 5-(1,1-dimethylethoxy)pentoxy, 6-(methoxy)hexoxy, 6-(ethoxy)hexoxy, 6-(n-propoxy)hexoxy, 6-(1-methylethoxy)hexoxy, 6-(n-butoxy)hexoxy, 6-(1-methylpropoxy)hexoxy, 6-(2-methylpropoxy)hexoxy or 6-(1,1-dimethylethoxy)hexoxy, in particular $OCH_2$—$OCH_3$ or $OCH_2$—$OC_2H_5$;

($C_1$–$C_6$-alkyl)carbonyl-$C_1$–$C_6$-alkoxy: $C_1$–$C_6$-alkoxy which is substituted by ($C_1$–$C_6$-alkyl)carbonyl as mentioned above, i.e., for example, $OCH_2$—CO—$CH_3$, $OCH_2$—CO—$C_2H_5$, $OCH_2$—CO—$CH_2$—$C_2H_5$, $OCH_2$—CO—$CH(CH_3)_2$, n-butylcarbonyl-methoxy, 1-(CO—$CH_3$)ethoxy, 2-(CO—$CH_3$)ethoxy, 2-(CO—$C_2H_5$)ethoxy, 2-(CO—$CH_2$—$C_2H_5$)ethoxy, 2-(n-butylcarbonyl)ethoxy, 3-(CO—$CH_3$)propoxy, 3-(CO—$C_2H_5$)-propoxy, 3-(CO—$CH_2$—$C_2H_5$)propoxy, 3-(n-butylcarbonyl)propoxy, 4-(CO—$CH_3$)butoxy, 4-(CO—$C_2H_5$)butoxy, 4-(CO—$CH_2$—$C_2H_5$)butoxy, 4-(n-butylcarbonyl)butoxy, 5-(CO—$CH_3$)pentoxy, 5-(CO—$C_2H_5$)pentoxy, 5-(CO—$CH_2$—$C_2H_5$)pentoxy, 5-(n-butylcarbonyl)butoxy, 6-(CO—$CH_3$)hexoxy, 6-(CO—$C_2H_5$)hexoxy, 6-(CO—$CH_2$—$C_2H_5$)hexoxy or 6-(n-butylcarbonyl)hexoxy, in particular $OCH_2$—CO—$OCH_3$ or 1-(CO—$CH_3$)ethoxy;

($C_1$–$C_6$-alkoxy)carbonyl-$C_1$–$C_6$-alkoxy: $C_1$–$C_6$-alkoxy which is substituted by ($C_1$–$C_6$-alkoxy)carbonyl as mentioned above, i.e., for example, $OCH_2$—CO—$OCH_3$, $OCH_2$—CO—$OC_2H_5$, $OCH_2$—CO—$OCH_2$—$C_2H_5$, $OCH_2$—CO—$OCH(CH_3)_2$, n-butoxycarbonyl-methoxy, 1-(methoxycarbonyl)ethoxy, 2-(methoxycarbonyl)ethoxy, 2-(ethoxycarbonyl)ethoxy, 2-(n-propoxycarbonyl)ethoxy, 2-(n-butoxycarbonyl)ethoxy, 3-(methoxycarbonyl)propoxy, 3-(ethoxycarbonyl)propoxy, 3-(n-propoxycarbonyl)propoxy, 3-(n-butoxycarbonyl)propoxy, 4-(methoxycarbonyl)butoxy, 4-(ethoxycarbonyl)butoxy, 4-(n-propoxycarbonyl)butoxy, 4-(n-butoxycarbonyl)butoxy, 5-(methoxycarbonyl)pentoxy, 5-(ethoxycarbonyl)pentoxy, 5-(n-propoxycarbonyl)pentoxy, 5-(n-butoxycarbonyl)butoxy, 6-(methoxycarbonyl)hexoxy, 6-(ethoxycarbonyl)hexoxy, 6-(n-propoxycarbonyl)hexoxy or 6-(n-butoxycarbonyl)hexoxy, in particular $OCH_2$—CO—$OCH_3$ or 1-(methoxycarbonyl)ethoxy;

($C_1$–$C_6$-alkoxy)carbonyl-$C_1$–$C_6$-alkyl: $C_1$–$C_6$-alkyl which is substituted by ($C_1$–$C_6$-alkoxy)carbonyl as mentioned above, i.e., for example, methoxycarbonylmethyl, ethoxycarbonylmethyl, 1-(methoxycarbonyl)ethyl, 2-(methoxycarbonyl)ethyl, 2-(ethoxycarbonyl)ethyl, 3-(methoxycarbonyl)propyl, 4-(methoxycarbonyl)butyl, 5-(methoxycarbonyl)pentyl or 6-(methoxycarbonyl)hexyl;

($C_1$–$C_6$-alkoxy)carbonyl-$C_1$–$C_6$-alkylsulfonyl: $C_1$–$C_6$-alkylsulfonyl which is substituted by ($C_1$–$C_6$-alkoxy)carbonyl as mentioned above, i.e., for example, methoxycarbonylmethylsulfonyl, ethoxycarbonylmethylsulfonyl, 1-(methoxycarbonyl)ethylsulfonyl, 2-(methoxycarbonyl)ethylsulfonyl, 2-(ethoxycarbonyl)ethylsulfonyl, 3-(methoxycarbonyl)propylsulfonyl, 4-(methoxycarbonyl)butylsulfonyl, 5-(methoxycarbonyl)pentylsulfonyl or 6-(methoxycarbonyl)hexylsulfonyl;

$C_1$–$C_6$-alkylthio-$C_1$–$C_6$-alkyl: $C_1$–$C_6$-alkyl which is substituted by $C_1$–$C_6$-alkylthio as mentioned above, i.e., for example, $CH_2$—$SCH_3$, $CH_2$—$SC_2H_5$, $CH_2$—$SCH_2$—$C_2H_5$, $CH_2$—$SCH(CH_3)_2$, n-butylthiomethyl, $CH_2$—$SCH(CH_3)$—$C_2H_5$, $CH_2$—$SCH_2$—$CH(CH_3)_2$, $CH_2$—$SC(CH_3)_3$, 2-($SCH_3$)ethyl, 2-($SC_2H_5$)ethyl, 2-($SCH_2$—$C_2H_5$)ethyl, 2-[$SCH(CH_3)_2$]ethyl, 2-(n-butylthio)ethyl, 2-[$SCH(CH_3)$—$C_2H_5$]ethyl, 2-(2-methylpropylthio)ethyl, 2-[$SC(CH_3)_3$]ethyl, 2-($SCH_3$)propyl, 3-($SCH_3$)propyl, 2-($SC_2H_5$)propyl, 3-($SC_2H_5$)propyl, 3-($SCH_2$—$C_2H_5$)propyl, 3-(butylthio)propyl, 4-($SCH_3$)butyl, 4-($SC_2H_5$)butyl, 4-($SCH_2$—$C_2H_5$)butyl or 4-(n-butylthio)butyl, in particular 2-($SCH_3$)ethyl;

$C_1$–$C_6$-alkylthio-$C_1$–$C_6$-alkoxy: $C_1$–$C_6$-alkoxy-which is substituted by $C_1$–$C_6$-alkylthio as mentioned above, i.e., for example, OCH$_2$—SCH$_3$, OCH$_2$—SC$_2$H$_5$, OCH$_2$—SCH$_2$—C$_2$H$_5$, OCH$_2$—SCH(CH$_3$)$_2$, n-butylthiomethoxy, OCH$_2$—SCH(CH$_3$)—C$_2$H$_5$, OCH$_2$—SCH$_2$—CH(CH$_3$)$_2$, OCH$_2$—SC(CH$_3$)$_3$, 2-(SCH$_3$)ethoxy, 2-(SC$_2$H$_5$)ethoxy, 2-(SCH$_2$—C$_2$H$_5$) ethoxy, 2-[SCH(CH$_3$)$_2$]ethoxy, 2-(n-butylthio)ethoxy, 2-[SCH(CH$_3$)—C$_2$H$_5$]ethoxy, 2-(2-methylpropylthio) ethoxy, 2-[SC(CH$_3$)$_3$]ethoxy, 2-(SCH$_3$)propoxy, 3-(SCH$_3$)propoxy, 2-(SC$_2$H$_5$)propoxy, 3-(SC$_2$H$_5$) propoxy, 3-(SCH$_2$—C$_2$H$_5$)propoxy, 3-(butylthio) propoxy, 4-(SCH$_3$)butoxy, 4-(SC$_2$H$_5$)butoxy, 4-(CH$_2$—C$_2$H$_5$)butoxy or 4-(n-butylthio)butoxy, in particular 2-(SCH$_3$)ethoxy;

$C_1$–$C_6$-alkylthio-($C_1$–$C_6$-alkyl)carbonyl: ($C_1$–$C_6$-alkyl) carbonyl which is substituted by $C_1$–$C_6$-alkylthio as mentioned above, preferably by SCH$_3$ or SC$_2$H$_5$, i.e., for example, methylthiomethylcarbonyl, ethylthiomethylcarbonyl, 1-(methylthio)ethylcarbonyl, 2-(methylthio)ethylcarbonyl, 3-(methylthio) propylcarbonyl, 4-(methylthio)butylcarbonyl, 5-(methylthio)pentylcarbonyl or 6-(methylthio) hexylcarbonyl, in particular CO—CH$_2$—SCH$_3$ or CO—CH(CH$_3$)—SCH$_3$; di($C_1$–$C_6$-alkyl)amino-$C_1$–$C_6$-alkoxy: $C_1$–$C_6$-alkoxy which is substituted by di($C_1$–$C_6$-alkyl)amino such as N(CH$_3$)$_2$, N(C$_2$H$_5$)$_2$, N,N-dipropylamino, N,N-di(1-methylethyl)amino, N,N-dibutylamino, N,N-di(1-methylpropyl)amino, N,N-di(2-methylpropyl)amino, N[C(CH$_3$)$_3$]$_2$, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl) amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl) amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino, preferably by N,N-dimethylamino or N,N-diethylamino, i.e., for example, OCH$_2$—N(CH$_3$)$_2$, OCH$_2$—N(C$_2$H$_5$)$_2$, OCH(CH$_3$)—N(CH$_3$)$_2$, 2-(dimethylamino)ethoxy, OCH(CH$_3$)—N(C$_2$H$_5$)$_2$, 3-(dimethylamino)propoxy, 4-(dimethylamino)butoxy, 5-(dimethylamino)pentoxy or 6-(dimethylamino)hexoxy, in particular OCH$_2$—N(CH$_3$)$_2$ or OCH(CH$_3$)—N(CH$_3$)$_2$;

$C_3$–$C_6$-alkenyl: for example prop-2-en-1-yl, n-buten-4-yl, 1-methylprop-2-en-1-yl, 2-methylprop-2-en-1-yl, 2-buten-1-yl, n-penten-3-yl, n-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, n-hex-3-en-1-yl, n-hex-4-en-1-yl, n-hex-5-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl or 1-ethyl-2-methylprop-2-en-1-yl, in particular prop-2-en-1-yl or n-buten-4-yl;

$C_2$–$C_6$-alkenyl: ethenyl or one of the radicals mentioned under $C_3$–$C_6$-alkenyl, in particular ethenyl or prop-2-en-1-yl;

$C_3$–$C_6$-alkenyloxy: prop-1-en-1-yloxy, prop-2-en-1-yloxy, 1-methylethenyloxy, n-buten-1-yloxy, n-buten-2-yloxy, n-buten-3-yloxy, 1-methylprop-1-en-1-yloxy, 2-methylprop-1-en-1-yloxy, 1-methylprop-2-en-1-yloxy, 2-methylprop-2-en-1-yloxy, n-penten-1-yloxy, n-penten-2-yloxy, n-penten-3-yloxy, n-penten-4-yloxy, 1-methylbut-1-en-1-yloxy, 2-methylbut-1-en-1-yloxy, 3-methylbut-1-en-1-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-1-en-1-yloxy, 1,2-dimethylprop-2-en-1-yloxy, 1-ethylprop-1-en-2-yloxy, 1-ethylprop-2-en-1-yloxy, n-hex-1-en-1-yloxy, n-hex-2-en-1-yloxy, n-hex-3-en-1-yloxy, n-hex-4-en-1-yloxy, n-hex-5-en-1-yloxy, 1-methylpent-1-en-1-yloxy, 2-methylpent-1-en-1-yloxy, 3-methylpent-1-en-1-yloxy, 4-methylpent-1-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1-dimethylbut-3-en-1-yloxy, 1,2-dimethylbut-1-en-1-yloxy, 1,2-dimethylbut-2-en-1-yloxy, 1,2-dimethylbut-3-en-1-yloxy, 1,3-dimethylbut-1-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-1-en-1-yloxy, 2,3-dimethylbut-2-en-1-yloxy, 2,3-dimethylbut-3-en-1-yloxy, 3,3-dimethylbut-1-en-1-yloxy, 3,3-dimethylbut-2-en-1-yloxy, 1-ethylbut-1-en-1-yloxy, 1-ethylbut-2-en-1-yloxy, 1-ethylbut-3-en-1-yloxy, 2-ethylbut-1-en-1-yloxy, 2-ethylbut-2-en-1-yloxy, 2-ethylbut-3-en-1-yloxy, 1,1,2-trimethylprop-2-en-1-yloxy, 1-ethyl-1-methylprop-2-en-1-yloxy, 1-ethyl-2-methylprop-1-en-1-yloxy or 1-ethyl-2-methylprop-2-en-1-yloxy, in particular prop-2-en-1-yloxy;

$C_2$–$C_6$-alkenyloxy: ethenyloxy or one of the radicals mentioned under $C_3$–$C_6$-alkenyloxy, in particular ethenyloxy or prop-2-ene-1-yloxy;

$C_3$–$C_6$-haloalkenyloxy: $C_3$–$C_6$-alkenyloxy as mentioned above which is partially or fully substituted by fluorine, chlorine and/or bromine, i.e., for example, 2-chloroallyloxy, 3-chloroallyloxy, 2,3-dichloroallyloxy, 3,3-dichloroallyloxy, 2,3,3-trichloroallyloxy, 2,3-dichlorobut-2-enyloxy, 2-bromoallyloxy, 3-bromoallyloxy, 2,3-dibromoallyloxy, 3,3-dibromoallyloxy, 2,3,3-tribromoallyloxy or 2,3-dibromobut-2-enyloxy, in particular 2-chloroallyloxy or 3,3-dichloroallyloxy;

$C_2$–$C_6$-alkenylthio: ethenylthio, prop-1-en-1-ylthio, prop-2-en-1-ylthio, 1-methylethenylthio, n-buten-1-ylthio, n-buten-2-ylthio, n-buten-3-ylthio, 1-methylprop-1-en-1-ylthio, 2-methylprop-1-en-1-ylthio, 1-methylprop-2-en-1-ylthio, 2-methylprbp-2-en-1-ylthio, n-penten-1-ylthio, n-penten-2-ylthio, n-penten-3-ylthio, n-penten-4-ylthio, 1-methylbut-1-en-1-ylthio, 2-methylbut-1-en-1-ylthio, 3-methylbut-1-en-1-ylthio, 1-methylbut-2-en-1-ylthio, 2-methylbut-2-en-1-ylthio, 3-methylbut-2-en-1-ylthio, 1-methylbut-3-en-1-ylthio, 2-methylbut-3-en-1-ylthio, 3-methylbut-3-en-1-ylthio, 1,1-dimethylprop-2-en-1-ylthio, 1,2-dimethylprop-1-en-1-ylthio, 1,2-dimethylprop-2-en-1-ylthio, 1-ethylprop-1-en-2-ylthio, 1-ethylprop-2-en-1-ylthio, n-hex-1-en-1-ylthio, n-hex-2-en-1-ylthio, n-hex-3-en-1-ylthio, n-hex-4-en-1-ylthio, n-hex-5-en-1-ylthio, 1-methylpent-1-en-1-ylthio, 2-methylpent-1-en-1-ylthio, 3-methylpent-1-en-1-ylthio, 4-methylpent-1-en-1-ylthio, 1-methylpent-2-en-1-ylthio, 2-methylpent-2-en-1-ylthio, 3-methylpent-2-en-1-ylthio, 4-methylpent-2-en-1-ylthio, 1-methylpent-3-en-1-ylthio, 2-methylpent-3-en-1-ylthio, 3-methylpent-3-en-1-ylthio, 4-methylpent-3-en-1-ylthio, 1-methylpent-4-en-1-ylthio, 2-methylpent-4-en-1-ylthio, 3-methylpent-4-en-1-ylthio, 4-methylpent-4-en-1-ylthio, 1,1-dimethylbut-2-en-1-ylthio, 1,1-dimethylbut-3-en-1-ylthio, 1,2-dimethylbut-1-en-1-ylthio, 1,2-dimethylbut-2-en-1-ylthio, 1,2-dimethylbut-3-en-1-ylthio, 1,3-dimethylbut-1-en-1-ylthio, 1,3-dimethylbut-2-en-1-ylthio, 1,3-dimethylbut-3-en-1-ylthio, 2,2-dimethylbut-3-en-1-ylthio, 2,3-dimethylbut-1-en-1-ylthio, 2,3-dimethylbut-2-en-1-ylthio, 2,3-dimethylbut-3-en-1-ylthio, 3,3-dimethylbut-1-en-1-ylthio, 3,3-dimethylbut-2-en-1-ylthio, 1-ethylbut-1-en-1-ylthio, 1-ethylbut-2-en-1-ylthio, 1-ethylbut-3-en-1-ylthio, 2-ethylbut-1-en-1-ylthio, 2-ethylbut-2-en-1-ylthio, 2-ethylbut-3-en-1-ylthio, 1,1,2-trimethylprop-2-en-1-ylthio, 1-ethyl-1-methylprop-2-en-1-ylthio, 1-ethyl-2-methylprop-1-en-1-ylthio or 1-ethyl-2-methylprop-2-en-1-ylthio, in particular ethenylthio or prop-2-en-1-ylthio;

$C_3$–$C_6$-alkynyl: prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl, in particular prop-2-yn-1-yl;

$C_2$–$C_6$-alkynyl: ethynyl or one of the radicals mentioned under $C_3$–$C_6$-alkynyl, in particular ethynyl or prop-2-yn-1-yl;

$C_3$–$C_6$-alkynyloxy: prop-1-yn-1-yloxy, prop-2-yn-1-yloxy, n-but-1-yn-1-yloxy, n-but-1-yn-3-yloxy, n-but-1-yn-4-yloxy, n-but-2-yn-1-yloxy, n-pent-1-yn-1-yloxy, n-pent-1-yn-3-yloxy, n-pent-1-yn-4-yloxy, n-pent-1-yn-5-yloxy, n-pent-2-yn-1-yloxy, n-pent-2-yn-4-yloxy, n-pent-2-yn-5-yloxy, 3-methylbut-1-yn-3-yloxy, 3-methylbut-1-yn-4-yloxy, n-hex-1-yn-1-yloxy, n-hex-1-yn-3-yloxy, n-hex-1-yn-4-yloxy, n-hex-1-yn-5-yloxy, n-hex-1-yn-6-yloxy, n-hex-2-yn-1-yloxy, n-hex-2-yn-4-yloxy, n-hex-2-yn-5-yloxy, n-hex-2-yn-6-yloxy, n-hex-3-yn-1-yloxy, n-hex-3-yn-2-yloxy, 3-methylpent-1-yn-1-yloxy, 3-methylpent-1-yn-3-yloxy, 3-methylpent-1-yn-4-yloxy, 3-methylpent-1-yn-5-yloxy, 4-methylpent-1-yn-1-yloxy, 4-methylpent-2-yn-4-yloxy or 4-methylpent-2-yn-5-yloxy, in particular prop-2-yn-1-yloxy;

$C_2$–$C_6$-alkynyloxy: ethynyloxy or one of the radicals mentioned under $C_3$–$C_6$-alkynyloxy, in particular ethynyloxy or prop-2-yn-1-yloxy;

$C_3$–$C_6$-alkynylthio: prop-1-yn-1-ylthio, prop-2-yn-1-ylthio, n-but-1-yn-1-ylthio, n-but-1-yn-3-ylthio, n-but-1-yn-4-ylthio, n-but-2-yn-1-ylthio, n-pent-1-yn-1-ylthio, n-pent-1-yn-3-ylthio, n-pent-1-yn-4-ylthio, n-pent-1-yn-5-ylthio, n-pent-2-yn-1-ylthio, n-pent-2-yn-4-ylthio, n-pent-2-yn-5-ylthio, 3-methylbut-1-yn-3-ylthio, 3-methylbut-1-yn-4-ylthio, n-hex-1-yn-1-ylthio, n-hex-1-yn-3-ylthio, n-hex-1-yn-4-ylthio, n-hex-1-yn-5-ylthio, n-hex-1-yn-6-ylthio, n-hex-2-yn-1-ylthio, n-hex-2-yn-4-ylthio, n-hex-2-yn-5-ylthio, n-hex-2-yn-6-ylthio, n-hex-3-yn-1-ylthio, n-hex-3-yn-2-ylthio, 3-methylpent-1-yn-1-ylthio, 3-methylpent-1-yn-3-ylthio, 3-methylpent-1-yn-4-ylthio, 3-methylpent-1-yn-5-ylthio, 4-methylpent-1-yn-1-ylthio, 4-methylpent-2-yn-4-ylthio or 4-methylpent-2-yn-5-ylthio, in particular prop-2-yn-1-ylthio;

$C_2$–$C_6$-alkynylthio: ethynylthio or one of the radicals mentioned under $C_3$–$C_6$-alkynylthio, in particular ethynylthio or prop-2-yn-1-ylthio;

($C_3$–$C_6$-alkenyloxy)carbonyl: prop-1-en-1-yloxycarbonyl, prop-2-en-1-yloxycarbonyl, 1-methylethenyloxycarbonyl, n-buten-1-yloxycarbonyl, n-buten-2-yloxycarbonyl, n-buten-3-yloxycarbonyl, 1-methylprop-1-en-1-yloxycarbonyl, 2-methylprop-1-en-1-yloxycarbonyl, 1-methylprop-2-en-1-yloxycarbonyl, 2-methylprop-2-en-1-yloxycarbonyl, n-penten-1-yloxycarbonyl, n-penten-2-yloxycarbonyl, n-penten-3-yloxycarbonyl, n-penten-4-yloxycarbonyl, 1-methylbut-1-en-1-yloxycarbonyl, 2-methylbut-1-en-1-yloxycarbonyl, 3-methylbut-1-en-1-yloxycarbonyl, 1-methylbut-2-en-1-yloxycarbonyl, 2-methylbut-2-en-1-yloxycarbonyl, 3-methylbut-2-en-1-yloxycarbonyl, 1-methylbut-3-en-1-yloxycarbonyl, 2-methylbut-3-en-1-yloxycarbonyl, 3-methylbut-3-en-1-yloxycarbonyl, 1,1-dimethylprop-2-en-1-yloxycarbonyl, 1,2-dimethylprop-1-en-1-yloxycarbonyl, 1,2-dimethylprop-2-en-1-yloxycarbonyl, 1-ethylprop-1-en-2-yloxycarbonyl, 1-ethylprop-2-en-1-yloxycarbonyl, n-hex-1-en-1-yloxycarbonyl, n-hex-2-en-1-yloxycarbonyl, n-hex-3-en-1-yloxycarbonyl, n-hex-4-en-1-yloxycarbonyl, n-hex-5-en-1-yloxycarbonyl, 1-methylpent-1-en-1-yloxycarbonyl, 2-methylpent-1-en-1-yloxycarbonyl, 3-methylpent-1-en-1-yloxycarbonyl, 4-methylpent-1-en-1-yloxycarbonyl, 1-methylpent-2-en-1-yloxycarbonyl, 2-methylpent-2-en-1-yloxycarbonyl, 3-methylpent-2-en-1-yloxycarbonyl, 4-methylpent-2-en-1-yloxycarbonyl, 1-methylpent-3-en-1-yloxycarbonyl, 2-methylpent-3-en-1-yloxycarbonyl, 3-methylpent-3-en-1-yloxycarbonyl, 4-methylpent-3-en-1-yloxycarbonyl, 1-methylpent-4-en-1-yloxycarbonyl, 2-methylpent-4-en-1-yloxycarbonyl, 3-methylpent-4-en-1-yloxycarbonyl, 4-methylpent-4-en-1-yloxycarbonyl, 1,1-dimethylbut-2-en-1-yloxycarbonyl, 1,1-dimethylbut-3-en-1-yloxycarbonyl, 1,2-dimethylbut-1-en-1-yloxycarbonyl, 1,2-dimethylbut-2-en-1-yloxycarbonyl, 1,2-dimethylbut-3-en-1-yloxycarbonyl, 1,3-dimethylbut-1-en-1-yloxycarbonyl, 1,3-dimethylbut-2-en-1-yloxycarbonyl, 1,3-dimethylbut-3-en-1-yloxycarbonyl, 2,3- dimethylbut-3-en-1-yloxycarbonyl, 2,3-dimethylbut-1-en-1-yloxycarbonyl, 2,3-dimethylbut-2-en-1-yloxycarbonyl, 2,3-dimethylbut-3-en-1-yloxycarbonyl, 3, 3-dimethylbut-1-en-1-yloxycarbonyl, 3,3-dimethylbut-2-en-1-yloxycarbonyl, 1-ethylbut-2-en-1-yloxycarbonyl, 1-ethylbut-2-en-1-yloxycarbonyl, 1-ethylbut-3-en-1-yloxycarbonyl, 2-ethylbut-1-en-1-yloxycarbonyl, 2-ethylbut-2-en-1-yloxycarbonyl, 2-ethylbut-3-en-1-yloxycarbonyl, 1,1,2-trimethylprop-2-en-1-yloxycarbonyl, 1-ethyl-methylprop-2-en-1-yloxycarbonyl, 1-ethyl-2-methylprop-1-en-1-yloxycarbonyl or 1-ethyl-2-methylprop-2-en-1-yloxycarbonyl, in particular prop-2-en-1-yloxycarbonyl;

($C_3$–$C_6$-alkenyloxy)carbonyl-$C_1$–$C_6$-alkyl: $C_1$–$C_6$-alkyl which is substituted by ($C_3$–$C_6$-alkenyloxy)carbonyl as mentioned above, preferably by prop-2-en-1-yl-oxycarbonyl, i.e., for example, prop-2-en-1-yl-oxycarbonyl-methyl; ($C_2$–$C_6$-alkenyl)carbonyloxy: ethenylcarbonyloxy, prop-1-en-1-ylcarbonyloxy, prop-2-en-1-ylcarbonyloxy, 1-methylethenylcarbonyloxy, n-buten-1-ylcarbonyloxy, n-buten-2-ylcarbonyloxy, n-buten-3-ylcarbonyloxy, 1-methylprop-1-en-1-ylcarbonyloxy, 2-methylprop-1-en-1-ylcarbonyloxy, 1-methylprop-2-en-1-ylcarbonyloxy, 2-methylprop-2-en-1-ylcarbonyloxy, n-penten-1-ylcarbonyloxy, n-penten-2-ylcarbonyloxy, n-penten-3-ylcarbonyloxy, n-penten-4-ylcarbonyloxy, 1-methylbut-1-en-1-ylcarbonyloxy, 2-methylbut-1-en-1-ylcarbonyloxy, 3-methylbut-1-en-1-ylcarbonyloxy, 1-methylbut-2-en-1-ylcarbonyloxy, 2-methylbut-2-en-1-ylcarbonyloxy, 3-methylbut-2-en-1-ylcarbonyloxy, 1-methylbut-3-en-1-ylcarbonyloxy, 2-methylbut-3-en-1-ylcarbonyloxy, 3-methylbut-3-en-1-ylcarbonyloxy, 1,1-dimethylprop-2-en-1-ylcarbonyloxy, 1,2-dimethylprop-1-en-1-ylcarbonyloxy, 1,2-dimethylprop-2-en-1-ylcarbonyloxy, 1-ethylprop-1-en-2-ylcarbonyloxy, 1-ethylprop-2-en-1-ylcarbonyloxy, n-hex-1-en-1-ylcarbonyloxy, n-hex-2-en-1-ylcarbonyloxy, n-hex-3-en-1-ylcarbonyloxy, n-hex-4-en-1-ylcarbonyloxy, n-hex-5-en-1-ylcarbonyloxy, 1-methylpent-1-en-1-ylcarbonyloxy, 2-methylpent-1-en-1-ylcarbonyloxy, 3-methylpent-1-en-1-ylcarbonyloxy, 4-methylpent-1-en-1-ylcarbonyloxy, 1-methylpent-2-en-1-ylcarbonyloxy, 2-methylpent-2-en-1-ylcarbonyloxy, 3-methylpent-2-en-1-ylcarbonyloxy, 4-methylpent-2-en-1-ylcarbonyloxy, 1-methylpent-3-en-1-ylcarbonyloxy, 2-methylpent-3-en-1-ylcarbonyloxy, 3-methylpent-3-en-1-ylcarbonyloxy, 4-methylpent-3-en-1-ylcarbonyloxy, 1-methylpent-4-en-1-ylcarbonyloxy, 2-methylpent-4-en-1-ylcarbonyloxy, 3-methylpent-4-en-1-ylcarbonyloxy, 4-methylpent-4-en-1-ylcarbonyloxy, 1,1-dimethylbut-2-en-1-ylcarbonyloxy, 1,1-dimethylbut-3-en-1-ylcarbonyloxy, 1,2-dimethylbut-1-en-1-ylcarbonyloxy, 1,2-dimethylbut-2-en-1-ylcarbonyloxy, 1,2-dimethylbut-3-en-1-ylcarbonyloxy, 1,3-dimethylbut-1-en-1-ylcarbonyloxy, 1,3-dimethylbut-2-en-1-ylcarbonyloxy, 1,3-dimethylbut-3-en-1-ylcarbonyloxy, 2,2-dimethylbut-3-en-1-ylcarbonyloxy, 2,3-dimethylbut-1-en-1-ylcarbonyloxy, 2,3-dimethylbut-2-en-1-ylcarbonyloxy, 2,3-dimethylbut-3-en-1-ylcarbonyloxy, 3,3-dimethylbut-1-en-1-ylcarbonyloxy, 3,3-dimethylbut-2-en-1-ylcarbonyloxy, 1-ethylbut-1-en-1-ylcarbonyloxy, 1-ethylbut-2-en-1-ylcarbonyloxy, 1-ethylbut-3-en-1-ylcarbonyloxy, 2-ethylbut-1-en-1-ylcarbonyloxy, 2-ethylbut-2-en-1-ylcarbonyloxy, 2-ethylbut-3-en-1-ylcarbonyloxy, 1,1,2-trimethylprop-2-en-1-ylcarbonyloxy, 1-ethyl-1-methylprop-2-en-1-ylcarbonyloxy, 1-ethyl-2-methylprop-1-en-1-ylcarbonyloxy or 1-ethyl-2-methylprop-2-en-1-ylcarbonyloxy, in particular ethenylcarbonyloxy or prop-2-en-1-ylcarbonyloxy;

($C_1$–$C_6$-alkoxy)carbonyl-$C_2$–$C_6$-alkenyl: $C_2$–$C_6$-alkenyl which is substituted by ($C_1$–$C_6$-alkoxy)carbonyl as mentioned above, i.e., for example, methoxycarbonylprop-2-en-1-yl;

$C_1$–$C_6$-alkoxy-$C_3$–$C_6$-alkenyloxy: $C_3$–$C_6$-alkenyloxy which is substituted by $C_1$–$C_6$-alkoxy as mentioned above, i.e., for example, methylprop-2-en-1-yloxy;

$C_3$–$C_6$-alkenyloxy-$C_1$–$C_6$-alkyl: $C_1$–$C_6$-alkyl which is substituted by $C_3$–$C_6$-alkenyloxy as mentioned above, preferably by allyloxy, 2-methylprop-2-en-1-yloxy, but-1-en-3-yloxy, but-1-en-4-yloxy or but-2-en-1-yloxy, i.e., for example, allyloxymethyl, 2-allyloxyethyl or but-1-en-4-yloxymethyl;

$C_3$–$C_6$-alkynyloxy-$C_1$–$C_6$-alkyl: $C_1$–$C_6$-alkyl which is substituted by $C_3$–$C_6$-alkynyloxy as mentioned above, preferably by propargyloxy, but-1-yn-3-yloxy, but-1-yn-4-yloxy or but-2-yn-1-yloxy, i.e., for example, propargyloxymethyl or 2-propargyloxyethyl;

$C_3$–$C_6$-haloalkenyl: $C_3$–$C_6$-alkenyl as mentioned above, which is partially or fully substituted by fluorine, chlorine and/or bromine, i.e., for example, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl, in particular 2-chloroallyl or 3,3-dichloroallyl;

$C_3$–$C_6$-haloalkynyl: $C_3$–$C_6$-alkynyl as mentioned above which is partially or fully substituted by fluorine, chlorine and/or bromine, i.e., for example, 3-chloropropargyl, 3-bromopropargyl, 3-fluoropropargyl, 3,3,3-trifluoropropargyl, 4-chlorobut-2-ynyl, 4-bromobut-2-ynyl, 4,4,4-trifluorobut-2-ynyl, 1,4-dichlorobut-2-ynyl, 5-chloropent-3-ynyl, 5-fluoropent-3-ynyl, 5,5,5-trifluoropent-3-ynyl, 6-chlorohex-2-ynyl, preferably 3-chloropropargyl, 3,3,3-trifluoropropargyl, 4,4,4-trifluorobut-2-ynyl;

$C_3$–$C_6$-cycloalkyl-$C_1$–$C_6$-alkyl: cyclopropylmethyl, cyclobutylmethyl, cyclopentylmethyl, cyclohexylmethyl, cycloheptylmethyl, cyclooctylmethyl, 1-(cyclopropyl)ethyl, 1-(cyclobutyl)ethyl, 1-(cyclopentyl)ethyl, 1-(cyclohexyl)ethyl, 2-(cyclopropyl)ethyl, 2-(cyclobutyl)ethyl, 2-(cyclopentyl)ethyl, 2-(cyclohexyl)ethyl, 2-(cyclopropyl)propyl, 3-(cyclopropyl)propyl, 3-(cyclobutyl)propyl, 3-(cyclopentyl)propyl, 3-(cyclohexyl)propyl, 2-(cyclopropyl)butyl, 3-(cyclopropyl)butyl, 4-(cyclopropyl)butyl, 4-(cyclobutyl)butyl, 4-(cyclopentyl)butyl, 4-(cyclohexyl)butyl, 2-(cyclopropyl)pentyl, 3-(cyclopropyl)pentyl, 4-(cyclopropyl)pentyl, 5-(cyclopropyl)pentyl, 2-(cyclobutyl)pentyl, 3-(cyclobutyl)pentyl, 5-(cyclobutyl)pentyl, 2-(cyclopropyl)hexyl, 3-(cyclopropyl)hexyl, 6-(cyclopropyl)hexyl, in particular cyclopentylmethyl or cyclohexylmethyl;

$C_3$–$C_6$-halocycloalkyl-$C_1$–$C_6$-alkyl: $C_3$–$C_6$-cycloalkyl-$C_1$–$C_6$-alkyl, as mentioned above which is partially or fully halogenated at the cycloalkylring, and preferably carries 1, 2, 3, 4 or 5 halogenatoms, especially fluorine or chlorine, i.e., for example perchlrocyclopropyl, perfluorocyclopropyl, 1-fluoro- or 1-chlorocyclopropyl, hexachlorocyclohexyl, etc.;

$C_3$–$C_6$-cycloalkoxy: cyclopropoxy, cyclobutoxy, cyclopentoxy, or cyclohexoxy;

$C_3$–$C_6$-cycloalkoxy-$C_1$–$C_4$-alkyl: cyclopropyloxymethyl, cyclobutyloxymethyl, cyclopentyloxymethyl, cyclohexyloxymethyl, 1-(cyclopropyloxy)ethyl, 1-(cyclobutyloxy)ethyl, 1-(cyclopentyloxy)ethyl, 1-(cyclohexyloxy)ethyl, 2-(cyclopropyloxy)ethyl, 2-(cyclobutyloxy)ethyl, 2-(cyclopentyloxy)ethyl, 2-(cyclohexyloxy)ethyl, 3-(cyclopropyloxy)propyl, 3-(cyclobutyloxy)propyl, 3-(cyclopentyloxy)propyl, 3-(cyclohexyloxy)propyl, 4-(cyclopropyloxy)butyl, 4-(cyclobutyloxy)butyl, 4-(cyclopentyloxy)butyl or 4-(cyclohexyloxy)butyl, in particular cyclopentyloxymethyl, cyclohexyloxymethyl or 2-(cyclopentyloxy)ethyl;

$C_6$–$C_{14}$-aromatic radicals: phenyl, naphthyl or anthracenyl or heteroaromatic radicals (aromatic heterocycyl) having 6 to 14 carbon ring atoms some of which, i.e. at least one, two, three, four or five, are replaced by heteroatoms selected from the group consisting of N, O and S. In addition, $C_6$–$C_{14}$-aromatic radicals can be attached via two adjacent carbon atoms to a 4- to 7-membered carbo- or heterocycle which can be saturated or partially unsaturated and which can, in addition to the carbon ring members, have one, two or three of the following hetero ring members: —O—, —S—, —S(O)$_2$—, —N=, —NH— or —N($C_1$–$C_6$-alkyl)—. Furthermore, the $C_6$–$C_{14}$-aromatic radicals can be mono-, di-, tri-, tetra- or pentasubstituted by the atom groups defined above.

The N'-substituted N-amino urea derivatives of the formula II used as starting materials in the process according to the invention and processes for their preparation are known per se and described in the literature, for example in WO 94/10173, and reference is here made to the corresponding literature for more details.

With a view to their use for the preparation of compounds having herbicidal action, R is preferably a group of the formula:

CHO, CN, C(O)OR$^3$, C(S)SR$^3$, C(S)OR$^3$, C(O)SR$^3$, C(O)R$^2$, P(O)R$^1$OR$^1$, P(O)(OR$^1$)$_2$, S(O)$_2$R$^2$ or SO$_2$NHR$^1$.

In particular

C(O)OR$^3$, C(S)SR$^3$, C(S)OR$^3$, C(O)SR$^3$, and specifically C(O)OR$^3$.

Independently of one another, the variables R$^1$ to R$^7$ are preferably as defined below:

R$^1$ is hydrogen, $C_1$–$C_6$-alkyl, $C_1$–$C_6$-haloalkyl, $C_1$–$C_3$-alkoxy-$C_1$–$C_3$-alkyl, $C_3$–$C_6$-alkenyl or $C_3$–$C_6$-alkynyl;

R$^2$ is $C_1$–$C_6$-alkyl, $C_3$–$C_6$-cycloalkyl, $C_3$–$C_6$-alkenyl, $C_3$–$C_6$-alkynyl, $C_1$–$C_6$-haloalkyl, $C_1$–$C_6$-alkoxy-$C_2$–$C_6$-alkyl, $C_1$–$C_6$-alkoxycarbonyl-$C_1$–$C_6$-alkyl, $C_1$–$C_6$-alkylthio-$C_1$–$C_6$-alkyl, $C_3$–$C_6$-alkenyloxycarbonyl-$C_1$–$C_6$-alkyl, $C_3$–$C_6$-alkynyloxycarbonyl-$C_1$–$C_6$-alkyl, $C_3$–$C_6$-alkenyloxy-$C_1$–$C_6$-alkyl, $C_3$–$C_6$-alkynyloxy-$C_1$–$C_6$-alkyl, $C_1$–$C_6$-haloalkoxy-$C_1$–$C_6$-alkyl, cyano-$C_1$–$C_6$-alkyl, halo-$C_2$–$C_6$-alkenyl, halo-$C_3$–$C_6$-alkynyl, $C_1$–$C_6$-alkylcarbonyl, CHR$^1$COR$^7$, P(O)(OR$^7$)$_2$, CHR$^1$P(S)(OR$^7$)$_2$, CHR$^1$C(O)NR$^4$R$^5$, CHR$^1$C(O)NH$_2$, is benzyl, phenyl, phenoxy-$C_1$–$C_6$-alkyl or benzyloxy-$C_1$–$C_6$-alkyl, where the four last-mentioned substituents may be substituted by halogen, $C_1$–$C_4$-alkyl or $C_1$–$C_4$-haloalkyl;

R$^3$ is $C_1$–$C_{15}$-alkyl, $C_3$–$C_8$-cycloalkyl, $C_2$–$C_{10}$-alkenyl, $C_3$–$C_{10}$-alkynyl, $C_1$–$C_6$-haloalkyl, $C_1$–$C_6$-alkoxy-$C_1$–$C_6$-alkyl, $C_1$–$C_6$-alkylthioalkyl, $C_1$–$C_6$-alkoxycarbonyl-$C_1$–$C_6$-alkyl, $C_3$–$C_6$-alkenyloxycarbonyl-$C_1$–$C_6$-alkyl, $C_3$–$C_6$-alkynyloxycarbonyl-$C_1$–$C_6$-alkyl, $C_3$–$C_6$-alkenyloxy-$C_1$–$C_6$-alkyl, $C_1$–$C_6$-haloalkoxy-$C_1$–$C_6$-alkyl, cyano-$C_1$–$C_6$-alkyl, halo-$C_3$–$C_6$-alkenyl, $C_1$–$C_6$-alkoxy-$C_3$–$C_6$-alkenyl, $C_1$–$C_6$-alkoxy-$C_3$–$C_6$-alkynyl, CHR$^1$COR$^7$, P(O)(OR$^7$)$_2$, CHR$^1$P(S)(OR$^7$)$_2$, CHR$^1$C(O)NR$^4$R$^5$, CHR$^1$C(O)NH$_2$, is benzyl, phenyl, phenoxy-$C_1$–$C_6$-alkyl or benzyloxy-$C_1$–$C_6$-alkyl, where the four last-mentioned substituents may be substituted by halogen, $C_1$–$C_4$-alkyl or $C_1$–$C_4$-haloalkyl;

R$^4$ is hydrogen, $C_1$–$C_6$-alkyl or $C_1$–$C_6$-alkoxy;

R$^5$, R$^6$ independently of one another are hydrogen, $C_1$–$C_6$-alkyl, $C_2$–$C_6$-alkenyl, $C_2$–$C_6$-alkynyl, $C_3$–$C_6$-cycloalkyl, $C_1$–$C_6$-haloalkyl, $C_1$–$C_6$-alkoxy-$C_1$–$C_6$-alkyl, $C_1$–$C_6$-alkoxycarbonyl-$C_1$–$C_6$-alkyl, $C_1$–$C_6$-alkoxycarbonyl-$C_2$–$C_6$-alkenyl, are benzyl which may be mono- to pentasubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkoxycarbonyl, $C_1$–$C_4$-alkoxycarbonyl-$C_1$–$C_4$-alkyl, nitro or cyano, or R$^4$ and R$^5$ together with the common nitrogen atom are a saturated or unsaturated 4- to 7-membered azaheterocycle which, in addition to the carbon ring members may, if desired, contain one of the following members: —O—, —S—, —N=, —NH— or —N($C_1$–$C_6$-alkyl)—;

R$^7$ is hydrogen, $C_1$–$C_6$-alkyl, $C_1$–$C_6$-haloalkyl, $C_1$–$C_3$-alkoxy-$C_1$–$C_3$-alkyl, $C_2$–$C_6$-cyanoalkyl, $C_3$–$C_6$-alkenyl or $C_3$–$C_6$-alkynyl.

R$^1$ is, in particular: $C_1$–$C_3$-alkyl, $C_1$–$C_3$-haloalkyl, $C_1$–$C_3$-alkoxy-$C_1$–$C_3$-alkyl.

R$^2$ is, in particular: $C_1$–$C_6$-alkyl, $C_3$–$C_6$-cycloalkyl, $C_3$–$C_4$-alkenyl, $C_3$–$C_4$-alkynyl, $C_1$–$C_3$-haloalkyl, $C_1$–$C_3$-alkoxy-$C_1$–$C_3$-alkyl, $C_1$–$C_3$-alkoxycarbonyl-$C_1$–$C_3$-alkyl, cyano-$C_1$–$C_3$-alkyl, halo-$C_2$–$C_4$-alkenyl, halo-$C_3$–$C_4$-alkynyl, $C_1$–$C_3$-alkylcarbonyl, CHR$^1$COR$^7$, P(O)(OR$^7$)$_2$, CHR$^1$P(S)(OR$^7$)$_2$, CHR$^1$C(O)NR$^4$R$^5$, CHR$^1$C(O)NH$_2$, $C_1$–$C_3$-alkyl, which is substituted by phenoxy or benzyloxy, benzyl or phenyl, which can be substituted by halogen, methyl or CF$_3$.

R$^3$ is, in particular: $C_1$–$C_{15}$-alkyl, $C_3$–$C_8$-cycloalkyl, $C_2$–$C_6$-alkenyl, $C_3$–$C_6$-alkynyl, $C_1$–$C_6$-haloalkyl, $C_1$–$C_3$-alkoxy-$C_1$–$C_3$-alkyl, $C_1$–$C_3$-alkoxycarbonyl-$C_1$–$C_3$-alkyl, $C_3$–$C_4$-alkenyloxycarbonyl-$C_1$–$C_3$-alkyl, $C_3$–$C_4$-alkynyloxycarbonyl-$C_1$–$C_3$-alkyl, cyano-$C_1$–$C_6$-alkyl, halo-$C_3$–$C_4$-alkenyl, CHR$^1$COR$^7$, P(O)(OR$^7$)$_2$, CHR$^1$C(O)NR$^4$R$^5$, CHR$^1$C(O)NH$_2$, $C_1$–$C_3$-alkyl which is substituted by phenoxy or benzyloxy, benzyl or phenyl which can be substituted by halogen, methyl or CF$_3$.

The variable m has, in particular, the value 0; Z is preferably oxygen or sulfur, in particular oxygen.

Examples of preferred perhydrodiazines of the formula I are the compounds of the formula Ia in which R has the meanings given in Table 1.

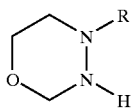

Ia

TABLE 1

| No. | R |
|---|---|
| 1 | CO$_2$H |
| 2 | CHO |
| 3 | CN |
| 4 | C(O)NHCH$_3$ |
| 5 | C(O)NHC$_2$H$_5$ |
| 6 | C(O)NH-N-C$_3$H$_7$ |
| 7 | C(O)NH-i-C$_3$H$_7$ |
| 8 | C(O)NH-c-C$_3$H$_5$ |
| 9 | C(O)NHCH$_2$CH=CH$_2$ |
| 10 | C(O)NHCH$_2$—C≡CH |
| 11 | C(O)NHCH$_2$CH$_2$OCH$_3$ |
| 12 | C(O)NHCH$_2$CO$_2$CH$_3$ |
| 13 | C(O)NHCH(CH$_3$)CO$_2$CH$_3$ |
| 14 | C(O)N(CH$_3$)$_2$ |
| 15 | C(O)N(CH$_3$)C$_2$H$_5$ |
| 16 | C(O)NHCH$_2$C$_6$H$_5$ |
| 17 | C(O)N(CH$_3$)CH$_2$C$_6$H$_5$ |
| 18 | C(O)NH-2-Cl-benzyl |
| 19 | C(O)NH-3-Cl-benzyl |
| 20 | C(O)NH-4-Cl-benzyl |
| 21 | C(O)NH-2-CH$_3$-benzyl |
| 22 | C(O)NH-3-CH$_3$-benzyl |
| 23 | C(O)NH-4-CH$_3$-benzyl |
| 24 | C(O)NH-2,3-Cl$_2$-benzyl |
| 25 | C(O)NH-3,4-Cl$_2$-benzyl |
| 26 | C(O)NH-2,4-Cl$_2$-benzyl |
| 27 | C(O)NH-3-CF$_3$-benzyl |
| 28 | C(O)NH-4-CF$_3$-benzyl |
| 29 | C(O)NH-3-NO$_2$-benzyl |
| 30 | C(O)NH-4-NO$_2$-benzyl |
| 31 | C(O)N(CH$_2$)$_5$ |
| 32 | C(O)N(CH$_2$CH$_2$OCH$_2$CH$_2$) |
| 33 | C(O)N(CH$_2$CH$_2$N(CH$_3$)CH$_2$CH$_2$) |
| 34 | C(O)NHSO$_2$CH$_3$ |
| 35 | C(O)NHSO$_2$C$_2$H$_5$ |
| 36 | C(O)NHSO$_2$-n-C$_3$H$_7$ |
| 37 | C(O)NHSO$_2$-i-C$_3$H$_7$ |
| 38 | C(O)NHCO$_2$CH$_3$ |
| 39 | C(O)NHCO$_2$C$_2$H$_5$ |
| 40 | C(O)NHCO$_2$-n-C$_3$H$_7$ |
| 41 | C(O)NHCO$_2$-i-C$_3$H$_7$ |
| 42 | C(O)NHCO$_2$-c-C$_3$H$_5$ |
| 43 | C(O)NHSO$_3$CH$_3$ |
| 44 | C(O)NHSO$_3$C$_2$H$_5$ |
| 45 | C(O)NHSO$_3$-n-C$_3$H$_7$ |
| 46 | C(O)NHSO$_3$-i-C$_3$H$_7$ |
| 47 | C(O)NHSO$_3$-c-C$_3$H$_5$ |
| 48 | C(O)CH$_3$ |
| 49 | C(O)C$_2$H$_5$ |
| 50 | C(O)-n-C$_3$H$_7$ |
| 51 | C(O)-i-C$_3$H$_7$ |
| 52 | C(O)-c-C$_3$H$_5$ |
| 53 | C(O)-n-C$_4$H$_9$ |
| 54 | C(O)-sec-C$_4$H$_9$ |
| 55 | C(O)-i-C$_4$H$_9$ |
| 56 | C(O)-t-C$_4$H$_9$ |
| 57 | C(O)CH$_2$CH=CH$_2$ |
| 58 | C(O)CH$_2$C≡CH |
| 59 | C(O)-c-C$_3$H$_5$ |
| 60 | C(O)-c-C$_5$H$_9$ |
| 61 | C(O)CH$_2$Cl |
| 62 | C(O)CF$_3$ |
| 63 | C(O)CH$_2$CF$_3$ |
| 64 | C(O)CH$_2$OCH$_3$ |
| 65 | C(O)CH$_2$OC$_2$H$_5$ |
| 66 | C(O)CH$_2$CO$_2$CH$_3$ |
| 67 | C(O)CH$_2$CH$_2$CO$_2$CH$_3$ |

TABLE 1-continued

| No. | R |
|---|---|
| 68 | C(O)CH$_2$CH$_2$CO$_2$CH$_2$CH=CH$_2$ |
| 69 | C(O)CH$_2$CH$_2$CO$_2$CH$_2$C≡CH |
| 70 | C(O)CH$_2$CN |
| 71 | C(O)CH$_2$CH$_2$CN |
| 72 | C(O)CH$_2$—C(Cl)=CH$_2$ |
| 73 | C(O)CH=CH$_2$ |
| 74 | C(O)CH$_2$C(O)CH$_3$ |
| 75 | C(O)CH$_2$P(O)(OCH$_3$)$_2$ |
| 76 | C(O)CH(CH$_3$)P(O)(OCH$_3$)$_2$ |
| 77 | C(O)CH$_2$C(O)N(CH$_3$)$_2$ |
| 78 | C(O)-benzyl |
| 79 | C(O)-3-CH$_3$-benzyl |
| 80 | C(O)-4-CH$_3$-benzyl |
| 81 | C(O)-3-Cl-benzyl |
| 82 | C(O)-4-Cl-benzyl |
| 83 | C(O)-3-CF$_3$-benzyl |
| 84 | C(O)-4-CF$_3$-benzyl |
| 85 | C(O)-phenyl |
| 86 | C(O)-3-CH$_3$-phenyl |
| 87 | C(O)-4-CH$_3$-phenyl |
| 88 | C(O)-3-Cl-phenyl |
| 89 | C(O)-4-Cl-phenyl |
| 90 | C(O)-3-CF$_3$-phenyl |
| 91 | C(O)-4-CF$_3$-phenyl |
| 92 | C(O)-2-pyridyl |
| 93 | C(O)-3-pyridyl |
| 94 | C(O)-4-pyridyl |
| 95 | P(O)(CH$_3$)OCH$_3$ |
| 96 | P(O)(C$_2$H$_5$)OCH$_3$ |
| 97 | P(O)(CH$_3$)OC$_2$H$_5$ |
| 98 | P(O)(CH$_3$)O-n-C$_3$H$_7$ |
| 99 | P(O)(OCH$_3$)$_2$ |
| 100 | P(O)(OC$_2$H$_5$)$_2$ |
| 101 | P(O)(OCH$_3$)OC$_2$H$_5$ |
| 102 | SOCH$_3$ |
| 103 | SOC$_2$H$_5$ |
| 104 | SO$_2$CH$_3$ |
| 105 | SO$_2$C$_2$H$_5$ |
| 106 | SO$_2$-n-C$_3$H$_7$ |
| 107 | SO$_2$-i-C$_3$H$_7$ |
| 108 | SO$_2$-c-C$_3$H$_5$ |
| 109 | SO$_2$-sec-C$_4$H$_9$ |
| 110 | SO$_2$—CH$_2$CH=CH$_2$ |
| 111 | SO$_2$CH$_2$Cl |
| 112 | SO$_2$CF$_3$ |
| 113 | SO$_2$CH$_2$CF$_3$ |
| 114 | SO$_2$CH$_2$OCH$_3$ |
| 115 | SO$_2$CH$_2$OC$_2$H$_5$ |
| 116 | SO$_2$CH$_2$CO$_2$CH$_3$ |
| 117 | SO$_2$CH$_2$CN |
| 118 | SO$_2$CH$_2$CH$_2$CN |
| 119 | SO$_2$CH=CH$_2$ |
| 120 | SO$_2$-benzyl |
| 121 | SO$_2$-3-CH$_3$-benzyl |
| 122 | SO$_2$-4-CH$_3$-benzyl |
| 123 | SO$_2$-3-Cl-benzyl |
| 124 | SO$_2$-4-Cl-benzyl |
| 125 | SO$_2$-3-CF$_3$-benzyl |
| 126 | SO$_2$-4-CF$_3$-benzyl |
| 127 | S(O)-phenyl |
| 128 | S(O)-3-Cl-phenyl |
| 129 | S(O)-4-Cl-phenyl |
| 130 | SO$_2$-3-Cl-phenyl |
| 131 | SO$_2$-4-Cl-phenyl |
| 132 | SO$_2$-3-CF$_3$-phenyl |
| 133 | SO$_2$-4-CF$_3$-phenyl |
| 134 | SO$_2$-3-CH$_3$-phenyl |
| 135 | SO$_2$-4-CH$_3$-phenyl |
| 136 | SO$_2$-3-pyridyl |
| 137 | SO$_2$-4-pyridyl |
| 138 | SO$_2$NH$_2$ |
| 139 | SO$_2$NHCH$_3$ |
| 140 | SO$_2$NHC$_2$H$_5$ |
| 141 | SO$_2$NH-i-C$_3$H$_7$ |
| 142 | SO$_2$NH-n-C$_3$H$_7$ |

TABLE 1-continued

| No. | R |
|---|---|
| 143 | SO$_2$NHCH$_2$CH$_2$Cl |
| 144 | SO$_2$NH-t-C$_4$H$_9$ |
| 145 | SO$_2$NH-n-C$_4$H$_9$ |

In Table 1, i denotes "iso", t denotes "tertiary" and c denotes "cyclo".

Examples of preferred perhydrodiazines of the formula I are furthermore the compounds of the formula Ib in which R is as defined in Table 1.

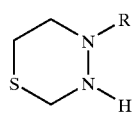

(Compounds Ib No. 1–Ib No. 145)

Very particularly preferred compounds of the formula I are compounds of the formula Ib.1 in which R is COOR$^3$, in particular those in which R$^3$ has the meanings given in Table 2.

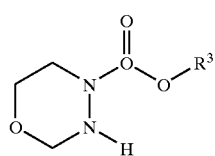

TABLE 2

| No. | R$^3$ |
|---|---|
| 1 | CH$_3$ |
| 2 | C$_2$H$_5$ |
| 3 | n-C$_3$H$_7$ |
| 4 | i-C$_3$H$_7$ |
| 5 | c-C$_3$H$_5$ |
| 6 | n-C$_4$H$_9$ |
| 7 | i-C$_4$H$_9$ |
| 8 | sec-C$_4$H$_9$ |
| 9 | c-C$_4$H$_7$ |
| 10 | t-C$_4$H$_9$ |
| 11 | n-C$_5$H$_{11}$ |
| 12 | sec-C$_5$H$_{11}$ |
| 13 | 2,2-dimethylpropyl |
| 14 | 2-methylbutyl |
| 15 | 3-methylbutyl |
| 16 | 1,1-dimethylpropyl |
| 17 | 1,2-dimethylpropyl |
| 18 | c-C$_5$H$_9$ |
| 19 | n-C$_6$H$_{13}$ |
| 20 | 1,1-dimethylbutyl |
| 21 | 1,2-dimethylbutyl |
| 22 | 1,3-dimethylbutyl |
| 23 | 2,2-dimethylbutyl |
| 24 | 2,3-dimethylbutyl |
| 25 | 3,3-dimethylbutyl |
| 26 | 1-ethylpropyl |
| 27 | 1-ethylbutyl |
| 28 | 2-ethylbutyl |
| 29 | 1,1,2-trimethylpropyl |
| 30 | 1,2,2-trimethylpropyl |
| 31 | 1-methylpentyl |
| 32 | 1-ethyl-1-methylpropyl |
| 33 | 1-ethyl-2-methylpropyl |

TABLE 2-continued

| No. | R$^3$ |
|---|---|
| 34 | c-C$_6$H$_{11}$ |
| 35 | n-C$_7$H$_{15}$ |
| 36 | 1-methylhexyl |
| 37 | 2-methylhexyl |
| 38 | 3-methylhexyl |
| 39 | 4-methylhexyl |
| 40 | 5-methylhexyl |
| 41 | 1-ethylpentyl |
| 42 | 2-ethylpentyl |
| 43 | 3-ethylpentyl |
| 44 | 4-ethylpentyl |
| 45 | 1,1-dimethylpentyl |
| 46 | 1,2-dimethylpentyl |
| 47 | 1,3-dimethylpentyl |
| 48 | 1,4-dimethylpentyl |
| 49 | c-C$_7$H$_{13}$ |
| 50 | n-C$_8$H$_{17}$ |
| 51 | 1-methylheptyl |
| 52 | 2-methylheptyl |
| 53 | 3-methylheptyl |
| 54 | 4-methylheptyl |
| 55 | 5-methylheptyl |
| 56 | 6-methylheptyl |
| 57 | 1-ethylhexyl |
| 58 | 2-ethylhexyl |
| 59 | 3-ethylhexyl |
| 60 | 4-ethylhexyl |
| 61 | 1,1-dimethylhexyl |
| 62 | 1,2-dimethylhexyl |
| 63 | 1,3-dimethylhexyl |
| 64 | 1,4-dimethylhexyl |
| 65 | 1,5-dimethylhexyl |
| 66 | c-C$_8$H15 |
| 67 | n-C$_9$H$_{19}$ |
| 68 | 1-methyloctyl |
| 69 | 2-methyloctyl |
| 70 | 3-methyloctyl |
| 71 | 4-methyloctyl |
| 72 | 5-methyloctyl |
| 73 | 6-methyloctyl |
| 74 | 7-methyloctyl |
| 75 | 1-ethylheptyl |
| 76 | 2-ethylheptyl |
| 77 | 3-ethylheptyl |
| 78 | 4-ethylheptyl |
| 79 | 5-ethylheptyl |
| 80 | 6-ethylheptyl |
| 81 | 1,1-dimethylheptyl |
| 82 | 1,2-dimethylheptyl |
| 83 | 1,3-dimethylheptyl |
| 84 | 1,4-dimethylheptyl |
| 85 | 1,5-dimethylheptyl |
| 86 | 1,6-dimethylheptyl |
| 87 | c-C$_9$H$_{17}$ |
| 88 | n-C$_{10}$H$_{21}$ |
| 89 | 1-methylnonyl |
| 90 | 2-methylnonyl |
| 91 | 3-methylnonyl |
| 92 | 4-methylnonyl |
| 93 | 5-methylnonyl |
| 94 | 1-ethyloctyl |
| 95 | 2-ethyloctyl |
| 96 | 3-ethyloctyl |
| 97 | 4-ethyloctyl |
| 98 | 5-ethyloctyl |
| 99 | 6-ethyloctyl |
| 100 | 7-ethyloctyl |
| 101 | 8-ethyloctyl |
| 102 | 1,1-dimethyloctyl |
| 103 | 1,2-dimethyloctyl |
| 104 | 1,3-dimethyloctyl |
| 105 | 1,4-dimethyloctyl |
| 106 | 1,5-dimethyloctyl |
| 107 | 1,6-dimethyloctyl |
| 108 | 1,7-dimethyloctyl |
| 109 | c-C$_{10}$H$_{19}$ |
| 110 | n-C$_{11}$H$_{23}$ |

TABLE 2-continued

| No. | R³ |
|---|---|
| 111 | 1-methyldecyl |
| 112 | 1-ethylnonyl |
| 113 | 1,1-dimethylnonyl |
| 114 | n-dodecyl |
| 115 | 1-methylundecyl |
| 116 | 1-ethyldecyl |
| 117 | 1,1-dimethyldecyl |
| 118 | 1-propylnonyl |
| 119 | n-tridecyl |
| 120 | 1-methyldodecyl |
| 121 | 1-ethylundecyl |
| 122 | 1,1-dimethylundecyl |
| 123 | n-tetradecyl |
| 124 | 1-methyltridecyl |
| 125 | 1-ethyldodecyl |
| 126 | 1,1-dimethyldodecyl |
| 127 | n-pentadecyl |
| 128 | $CH_2CH=CH_2$ |
| 129 | $CH_2C\equiv CH$ |
| 130 | $CH_2C(CH_3)=CH_2$ |
| 131 | $CH(CH_3)CH=CH_2$ |
| 132 | $CH(CH_3)C\equiv CH$ |
| 133 | $C(CH_3)_2CH=CH_2$ |
| 134 | $C(CH_3)_2C\equiv CH$ |
| 135 | $CH_2CH=CH—CH_3$ |
| 136 | $CH_2—C\equiv C—CH_3$ |
| 137 | $(CH_2)_2CH=CH—CH_3$ |
| 138 | $(CH_2)_2C\equiv C—CH_3$ |
| 139 | $(CH_2)_3CH=CH_2$ |
| 140 | $(CH_2)_3C\equiv CH$ |
| 141 | $(CH_2)_3CH=CHCH_3$ |
| 142 | $(CH_2)_3C\equiv C—CH_3$ |
| 143 | $CH_2CH_2Cl$ |
| 144 | $CH_2CH_2Br$ |
| 145 | $(CH_2)_3Cl$ |
| 146 | $CH(CH_3)CH_2Cl$ |
| 147 | $(CH_2)_2F$ |
| 148 | $(CH_2)_3F$ |
| 149 | $(CH_2)_4Cl$ |
| 150 | $(CH_2)_5Cl$ |
| 151 | $C(CH_3)_2CH_2Cl$ |
| 152 | $CH_2CH_2OCH_3$ |
| 153 | $CH(CH_3)CH_2OCH_3$ |
| 154 | $C(CH_3)_2CH_2OCH_3$ |
| 155 | $(CH_2)_3OCH_3$ |
| 156 | $(CH_2)_2OC_2H_5$ |
| 157 | $CH(CH_3)CH_2OC_2H_5$ |
| 158 | $CH_2CH_2SCH_3$ |
| 159 | $CH(CH_3)CH_2SCH_3$ |
| 160 | $C(CH_3)_2CH_2SCH_3$ |
| 161 | $(CH_2)_2SC_2H_5$ |
| 162 | $CH(CH_3)CH_2SC_2H_5$ |
| 163 | $CH_2CH_2S(O)CH_3$ |
| 164 | $CH_2CH_2SO_2CH_3$ |
| 165 | $CH_2CH_2S(O)C_2H_5$ |
| 166 | $CH_2CH_2SO_2C_2H_5$ |
| 167 | $CH_2CH_2OCH_2CH_2OCH_3$ |
| 168 | $CH_2CH_2OCH_2CH_2OC_2H_5$ |
| 169 | $CH(CH_3)CH_2OCH_2CH_2OCH_3$ |
| 170 | $CH_2$-c-$C_3H_5$ |
| 171 | $CH_2$-c-$C_4H_7$ |
| 172 | $CH_2$-c-$C_5H_9$ |
| 173 | $CH_2$-c-$C_6H_{11}$ |
| 174 | $CH_2CO_2H$ |
| 175 | $CH(CH_3)CO_2H$ |
| 176 | $(CH_2)_2CO_2H$ |
| 177 | $CH_2CO_2CH_3$ |
| 178 | $CH(CH_3)CO_2CH_3$ |
| 179 | $CH_2CH_2—O—CH_2CH=CH_2$ |
| 180 | $CH_2CH_2O—CH_2C\equiv CH$ |
| 181 | $CH_2CH_2O—CH_2CH_2Cl$ |
| 182 | $C(CH_3)_2CO_2CH_2CH=CH_2$ |
| 183 | $C(CH_3)_2CO_2CH_2C\equiv CH$ |
| 184 | $(CH_2)_2O$-c-$C_3H_5$ |
| 185 | $(CH_2)_2O$-c-$C_5H_7$ |
| 186 | $(CH_2)_2O—CH_2-CH=CHCl$ |
| 187 | $(CH_2)_2S—CH_2CH=CHCl$ |
| 188 | $(CH_2)_2S—CH_2CH=CH_2$ |
| 189 | $(CH_2)_2S—CH_2C\equiv CH$ |
| 190 | $(CH_2)_2CN$ |
| 191 | $(CH_2)_3CN$ |
| 192 | $CH(CH_3)CN$ |
| 193 | $(CH_2)_4CN$ |
| 194 | $(CH_2)_5CN$ |
| 195 | $(CH_2)_6CN$ |
| 196 | $CH_2C(O)H$ |
| 197 | $CH_2C(O)CH_3$ |
| 198 | $CH_2C(O)C_2H_5$ |
| 199 | $CH_2C(O)CH_2OCH_3$ |
| 200 | $CH_2C(O)(CH_2)_2OCH_3$ |
| 201 | $CH_2C(O)CH_2CN$ |
| 202 | $CH_2C(O)CH=CH_2$ |
| 203 | $CH_2P(O)(OCH_3)_2$ |
| 204 | $(CH_2)_2P(O)(OCH_3)_2$ |
| 205 | $CH_2P(S)(OCH_3)_2$ |
| 206 | $CH_2C(O)NHCH_3$ |
| 207 | $CH_2C(O)N(CH_3)_2$ |
| 208 | $(CH_2)_2C(O)N(CH_3)_2$ |
| 209 | $CH_2OC_6H_5$ |
| 210 | $CH_2O$-p-Cl-phenyl |
| 211 | $CH_2O$-p-tolyl |
| 212 | $(CH_2)_2O—C_6H_5$ |
| 213 | $(CH_2)_2O$-p-Cl-phenyl |
| 214 | $(CH_2)_2O$-p-tolyl |
| 215 | $C_6H_5$ |
| 216 | p-Cl-phenyl |
| 217 | m-Cl-phenyl |
| 218 | o-Cl-phenyl |
| 219 | o-tolyl |
| 220 | m-tolyl |
| 221 | p-tolyl |
| 222 | p-$CH_3O$-phenyl |
| 223 | m-$CH_3O$-phenyl |
| 224 | o-$CH_3O$-phenyl |
| 225 | 2,3-dichlorophenyl |
| 226 | 2,4-dichlorophenyl |
| 227 | 3-$CH_3$-4-chlorophenyl |
| 228 | 3-$CH_3O$-4-chlorophenyl |
| 229 | 2-$CF_3$-phenyl |
| 230 | 3-$CF_3$-phenyl |
| 231 | 4-$CF_3$-phenyl |
| 232 | 2-Cl-4-$CF_3$-phenyl |
| 233 | 3-Cl-4-$CH_3O$-phenyl |
| 234 | 3-$F_2CH$-o-phenyl |
| 235 | 4-$F_2CH$-o-phenyl |
| 236 | 2-$NO_2$-phenyl |
| 237 | 3-$NO_2$-phenyl |
| 238 | 4-$NO_2$-phenyl |
| 239 | 2-CN-phenyl |
| 240 | 3-CN-phenyl |
| 241 | 4-CN-phenyl |
| 242 | 2-$CH_3OC(O)$-phenyl |
| 243 | 3-$CH_3OC(O)$-phenyl |
| 244 | 4-$CH_3OC(O)$-phenyl |
| 245 | 3-$CH_3O—C(O)CH_2O$-phenyl |
| 246 | 3-$CH_3O—C(O)CH(CH_3)O$-phenyl |
| 247 | 4-$CH_3O—C(O)CH_2O$-phenyl |
| 248 | 4-$CH_3O—C(O)C(CH_3)_2O$-phenyl |
| 249 | 2-pyridyl |
| 250 | 3-pyridyl |
| 251 | 4-pyridyl |
| 252 | 1-naphthyl |
| 253 | 2-naphthyl |
| 254 | 2-chloro-1-naphthyl |
| 255 | 3-chloro-1-naphthyl |
| 256 | 4-chloro-1-naphthyl |
| 257 | 5-chloro-1-naphthyl |
| 258 | 2-chloro-4-nitro-1-naphthyl |
| 259 | 2-methyl-4-nitro-1-naphthyl |
| 260 | 5-chloro-8-methyl-1-naphthyl |
| 261 | 2-quinolyl |
| 262 | 3-quinolyl |
| 263 | 4-quinolyl |
| 264 | 5-quinolyl |

TABLE 2-continued

| No. | R³ |
|---|---|
| 265 | 8-quinolyl |
| 266 | 2-quinazolyl |
| 267 | 4-quinazolyl |
| 268 | 1-quinoxalyl |
| 269 | 1-methylindolyl-2 |
| 270 | 1-methylindolyl-3 |
| 271 | 1-methylbenzimidazolyl-2 |
| 272 | benzofuran-2-yl |
| 273 | benzofuran-3-yl |
| 274 | benzofuran-4-yl |
| 275 | benzofuran-5-yl |
| 276 | benzofuran-6-yl |
| 277 | 3-methylbenzofuran-5-yl |
| 278 | benzothienyl-2 |
| 279 | benzothienyl-3 |
| 280 | benzoxazolyl-3 |
| 281 | benzoxazolyl-4 |
| 282 | benzoxazolyl-5 |
| 283 | benzothiazolyl-3 |
| 284 | benzothiazolyl-4 |
| 285 | benzothiazolyl-5 |
| 286 | benzyl |
| 287 | 2-CH₃-benzyl |
| 288 | 3-CH₃-benzyl |
| 289 | 4-CH₃-benzyl |
| 290 | 2-Cl-benzyl |
| 291 | 3-Cl-benzyl |
| 292 | 4-Cl-benzyl |
| 293 | 2,3-dichlorobenzyl |
| 294 | 2,4-dichlorobenzyl |
| 295 | 2-CH₃-4-Cl-benzyl |
| 296 | 2-Cl-4-CH₃-benzyl |
| 297 | 2,6-Cl₂-4-CH₃-benzyl |
| 298 | 2-CH₃O-benzyl |
| 299 | 3-CH₃O-benzyl |
| 300 | 4-CH₃O-benzyl |
| 301 | 2-NO₂-benzyl |
| 302 | 3-NO₂-benzyl |
| 303 | 4-NO₂-benzyl |
| 304 | 2-CN-benzyl |
| 305 | 3-CN-benzyl |
| 306 | 4-CN-benzyl |

In Table 2 "o" denotes ortho, "m" denotes meta, "p" denotes para, indicating the position at the phenyl ring of the substituent listed next.

Very particular preference is also given to the compounds of the formula Ib.2,

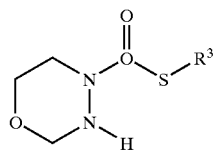

(Ib.2)

in which $R^3$ has the meanings listed in rows 1 to 306 of Table 2.

Very particular preference is furthermore given to the compounds of the formula Ib.3

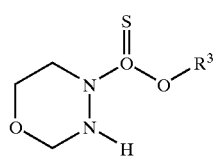

(Ib.3)

in which $R^3$ has the meanings given in rows 1 to 306 of Table 2.

Very particular preference is furthermore given to the compounds of the formula Ib.4

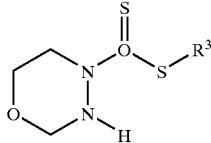

(Ib.4)

in which $R^3$ has the meanings given in rows 1 to 306 of Table 2.

Very particular preference is furthermore given to the compounds of the formula Ib.5

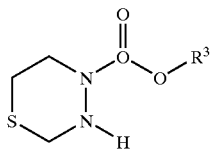

(Ib.5)

in which $R^3$ has the meanings given in rows 1 to 306 of Table 2.

Very particular preference is furthermore given to the compounds of the formula Ib.6

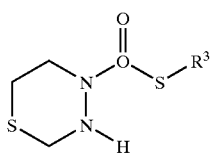

(Ib.6)

in which $R^3$ has the meanings given in rows 1 to 306 of Table 2.

Very particular preference is furthermore given to the compounds of the formula Ib.7

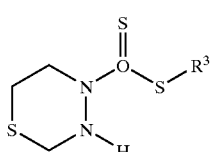

(Ib.7)

in which $R^3$ has the meanings given in rows 1 to 306 of Table 2.

Very particular preference is furthermore given to the compounds of the formula Ib.8

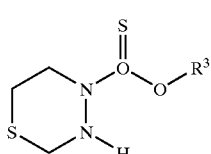

(Ib.8)

in which $R^3$ has the meanings given in rows 1 to 306 of Table 2.

According to the invention, the perhydrodiazine derivatives of the formula I are prepared by initially reacting a substituted hydrazine of the formula II

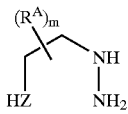
(II)

in which Z is O or S and $R^A$ and m are as defined above with an acid derivative of the formula III

R—G  (III)

in which R is as defined above and G is a nucleophilically displaceable leaving group, or R—G is an isocyanate of the formula $R^5$—N=C=X or a ketene of the formula $R^{2a}(R^{2b})$C=C=X in which X is O or S and $R^{2a}(R^{2b})$C—H is the radical $R^2$, $R^2$ and $R^5$ being as defined above—, and the resulting hydrazine derivative of the formula IV

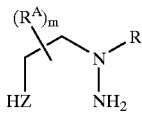
(IV)

is, in a second step, cyclized with formaldehyde in the presence of an acid to give the substituted perhydrodiazines of the formula I where Z=O or S. If appropriate, the radical R in the compounds of the formula I can be subsequently derivatized or converted into other radicals R by standard means; and/or in the case that Z=S, the compounds I can be oxidized in a further reaction step to give the sulfoxide Z=SO or the sulfones Z=$SO_2$.

Examples of suitable nucleophilically displaceable leaving groups are halogen, preferably chlorine or bromine, $C_1$–$C_6$-alkoxy such as methoxy, ethoxy, n-propoxy, n-butoxy, $C_1$–$C_4$-haloalkoxy such as trichloromethoxy, trifluoromethoxy, pentafluoroethoxy, N-bonded heterocyclyl such as imidazolyl, $C_1$–$C_6$-alkylcarbonyloxy (or $C_1$–$C_6$-alkanoate) such as acetate, propionate, n-butyrate, isobutyrate, pivalate and caproate, $C_1$–$C_6$-haloalkylcarbonyloxy such as mono-, di- and trichloroacetate, $C_1$–$C_6$-alkylsulfonyloxy such as methylsulfonyloxy, $C_1$–$C_6$-haloalkylsulfonyloxy such as trifluoromethylsulfonyloxy, phenylsulfonyloxy, where the phenyl radical may, if appropriate, be mono- or disubstituted by halogen or $C_1$–$C_6$-alkyl, such as phenylsulfonyloxy, p-toluenesulfonyloxy and p-Cl-phenylsulfonyloxy, N-bonded nitrogen-$C_5$–$C_6$-heterocyclyl, such as N-imidazolyl.

Preferred leaving groups are halogen, in particular chlorine or bromine, and furthermore acetate or trifluoroacetate, in particular if R is a group $C(O)OR^3$, $C(S)OR^3$, $C(S)SR^3$, $C(O)SR^3$, $P(O)R^1(OR^1)$, $P(O)(OR^1)_2$, $S(O)_2R^2$ or $SO_2HNR^1$.

According to the invention, it is also possible to prepare the compounds of the formula I by reacting, in the first reaction step, a substituted hydrazine with an isocyanate or an isothiocyanate of the formula R'—N=C=X, in which R' is $R^5$, or R' is a group $R^6$—W where W=$CO_2$, $S(O)_2$ or $S(O)_2O$. $R^5$ and $R^6$ are here as defined above. In the resulting hydrazines of the formula IV, R has then the meanings $C(O)NR^4R^5$ where $R^4$=H, $C(S)NR^4R^5$ where $R^4$=H, $C(O)NHCO_2R^6$, $C(O)NHS(O)_2R^6$ or $C(O)NHS(O)_2OR^6$.

According to the invention, it is also possible to prepare the compounds of the formula I in which R is $C(O)R^2$ by reacting the substituted hydrazines with a ketene of the formula $(R^{2a})(R^{2b})$C=C=O. In this case, R is a radical $C(O)R^2$ where $R^2$=HC$(R^{2a})(R^{2b})$ In a second reaction step, the hydrazides of the formula (IV) are then reacted with formaldehyde to give the 1-oxa-3,4-diazines or 1-thia-3,4-diazines of the formula I according to the invention here Z=O or S. The reaction can be carried out both using formaldehyde or a compound which releases formaldehyde under acidic conditions, such as paraformaldehyde or 1,3,5-trioxane, in the presence of an acid.

However, it is also possible to react the hydrazides IV with formaldehyde to give the compounds of the formula IVa which are then cyclized to give the 1-oxa- or 1-thiadiazines according to the invention.

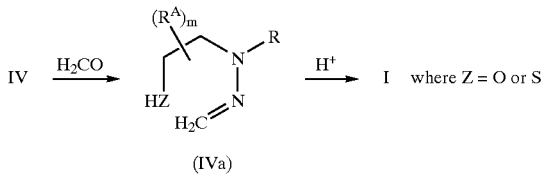
(IVa)

The cyclization is usually carried out under acidic conditions.

The reaction described in the scheme below is an example for the preparation of the compound I where, starting from 2-hydrazinoethanol and methyl chloroformate as acid derivative, firstly N-amino-N-methoxycarbonyl-2-hydrazinoethanol is prepared, which is cyclized in a subsequent reaction with formaldehyde to give tetrahydro-4-methoxycarbonyl-4H-1-oxa-3,4-diazine.

Preferred embodiments of the process are mentioned below:

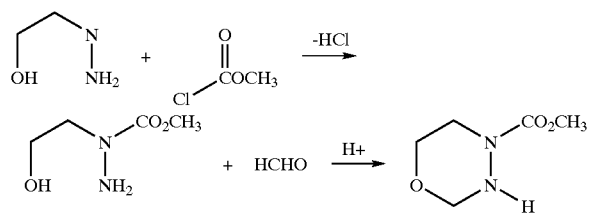

The first reaction step is explained in more detail below: the reaction of the hydrazinoethanol/thiols II with the compounds of the formula III is advantageously carried out in the presence of a solvent at from −30 to 100° C., preferably from −10 to 80° C., particularly preferably from 0 to 60° C.

The solvents used for these reactions are—depending on the temperature range—hydrocarbons, such as pentane, hexane, cyclopentane, cyclohexane, toluene, xylene, chlorinated hydrocarbons, such as methylene chloride, chloroform, 1,2-dichloroethane, 1,1,2,2-tetrachloroethane, chlorobenzene, 1,2-, 1,3- or 1,4-dichlorobenzene, ethers, such as 1,4-dioxane, anisol, glycol ethers such as dimethyl glycol ether, diethyl glycol ether, diethylene glycol dimethyl ether, esters such as ethyl acetate, propyl acetate, methylisobutyrate, isobutylacetate, carboxamides, such as DMF, N-methylpyrrolidone, nitrated hydrocarbons, such as nitrobenzene, ureas, such as tetraethyl urea, tetrabutyl urea, dimethylethylene urea, dimethylpropylene urea, sulfoxides such as dimethyl sulfoxide, sulfones such as dimethyl sulfone, diethyl sulfone, tetramethylene sulfone, nitriles, such as acetonitrile, propionitrile, butyronitrile or isobutyronitrile; water or else mixtures of individual solvents.

The molar ratios in which the starting materials II and III are reacted with one another are generally from 0.9 to 1.2, preferably 0.95 to 1.1, particularly preferably 0.98 to 1.04, for the ratio of acid derivative of the formula III to hydrazinoethanol/thiol II.

The first reaction step is advantageously carried out under neutral conditions. If an acidic reaction product is formed in the reaction, for example hydrogen halide if G in the formula III is halogen, this is removed by addition of basic compounds, for example alkali metal or alkaline earth metal hydroxides or bicarbonates or carbonates. However, the reaction can also be carried out in the presence of an organic base, for example triethylamine, tri-n-propylamine, N-ethyldiisopropylamine, pyridine, $\alpha$-, $\beta$-, $\gamma$-picoline, 2,4-, 2,6-lutidine, N-methylpyrrolidine, dimethylaniline, N,N-dimethylcyclohexylamine, quinoline or acridine.

Finally, the reaction can also be carried out in an aqueous two-phase system, preferably in the presence of phase-transfer catalysts, such as quaternary ammonium or phosphonium salts. The reaction conditions described in EP-A 556737 are suitable for the two-phase reaction.

The phase-transfer catalysts used can be quaternary ammonium or phosphonium salts. Suitable compounds which may be mentioned are: tetraalkyl($C_1$–$C_{18}$)ammonium chlorides, bromides or fluorides, N-benzyltrialkyl($C_1$–$C_{18}$) ammonium chlorides, bromides or fluorides, tetraalkyl ($C_1$–$C_{18}$)phosphonium chlorides or bromides, tetraphenylphosphonium chloride or -bromide, (phenyl)$_o$(alkyl ($C_1$–$C_{18}$)$_p$-phosphonium chlorides or bromides, where o=1 to 3, p=3 to 1 and o+p=4. Particular preference is given to tetraethylammonium chloride and N-benzyltriethylammonium chloride. The amount of phase-transfer catalyst is generally up to 20% by weight, preferably between 1 and 15% by weight. and particularly preferably between 2 and 8% by weight, based on the hydrazinoethanol/thiol II.

Advantageously, the acid derivative III is added, at 0 to 60° C. and over a period of 0.25 to 2 hours, to a mixture of the hydrazinoethanol/thiol II and the base in one of the abovementioned solvents, and stirring at 0 to 60° C. is continued for 0.5 to 16 hours, preferably 2 to 8 hours, for the reaction to go to completion.

If an aqueous two-phase system is used, the starting materials II and III can be added with stirring, in any order, to a mixture of the phase-transfer catalyst in the two phases, and the reaction can then be completed in the temperature range mentioned by adding base.

If the compound of the formula III is an isocyanate isothiocyanate or a ketene, addition of a base can be dispensed with. The reaction is in this case preferably carried out under anhydrous conditions.

The reaction can be carried out under atmospheric pressure or superatmospheric pressure, continuously or batchwise.

For work-up, any precipitated salts are separated off, or their removal is completed by addition of nonpolar solvents, and the hydrazides IV are thus enriched in the filtrate.

The second reaction step is explained below: the hydrazides IV are subsequently reacted, advantageously under acidic conditions, with a formaldehyde solution or paraformaldehyde in one of the abovementioned solvents.

For the subsequent step, advantageously 0.9 to 1.2, preferably 0.95 to 1.1, particularly preferably 0.98 to 1.04, molar equivalents of formaldehyde or paraformaldehyde are employed per mole of hydrazide derivative IV. The concentration of the starting materials in the solvent is 0.1 to 5 mol/l, preferably 0.2 to 2 mol/l.

The acid used can be an aromatic sulfonic acid, for example benzenesulfonic acid, p-chloro- or p-toluenesulfonic acid, an aliphatic sulfonic acid, such as methane sulfonic acid, trifluoromethane sulfonic acid, ethanesulfonic acid and n-propylsulfonic acid, a sulfaminic acid, such as methylsulfaminic acid, ethylsulfaminic acid or isopropylsulfaminic acid, an aliphatic carboxylic acid, such as acetic acid, trifluoroacetic acid, propionic acid, butyric acid or isobutyric acid, or an inorganic acid, such as hydrochloric acid, sulfuric acid, nitric acid or boric acid. Advantageously, it is also possible to use an acid such as acetic acid or propionic acid directly as reaction medium. The acid catalyst is advantageously employed in the amount from 1 to 20 mol %, preferably 3 to 15 mol %, particularly preferably 5 to 10 mol %, of acid per mole of hydrazide IV.

Preferably, a formaldehyde solution or paraformaldehyde is added over a period of 2 to 60 min to a mixture of hydrazide IV and the acid catalyst in one of the abovementioned solvents a 0 to 100° C., advantageously 10 to 80° C., particularly preferably 20 to 50° C., and stirring is continued at 40 to 50° C. for 10 to 50 hours, preferably 15 to 30 hours, to bring the reaction to completion.

If an aqueous formaldehyde solution is used, the water is advantageously removed, for example using a water separator.

However, it is also possible to add the acidic catalyst to a mixture of hydrazide IV and paraformaldehyde in one of the abovementioned solvents, and then to complete the reaction as described.

The reaction can be carried out under atmospheric pressure or under superatmospheric pressure, continuously or batchwise.

The oxidation of the perhydrodiazines I where Z=S to the sulfoxides, which follows, if appropriate, is preferably carried out using hydrogen peroxide, the sulfoxides being obtained with approximately equivalent amounts of oxidant, and the sulfones being obtained with about double the molar quantities.

The oxidation with hydrogen peroxide can be catalyzed by suitable metal compounds, for example transition metal oxides, such as vanadium pentoxide, sodium tungstate, potassium dichromate, iron oxide tungstate, sodium tungstate/molybdic acid, osmic acid, titanium trichloride, selenium dioxide, phenylselenic acid, vanadyl 2,4-pentane dionate. The catalysts are generally employed in an amount of from 0.5 to 10%, but it is also possible to employ stoichiometric amounts because the inorganic catalysts can easily be filtered off and recovered.

Solvents which are suitable for the oxidation with hydrogen peroxide are, for example, water, acetonitrile, alcohols, such as methanol, ethanol, isopropanol, tert-butanol, chlorinated hydrocarbons, such as methylene chloride, 1,1,2,2-tetrachloroethane, or ketones, such as acetone or methyl ethyl ketone.

In addition to hydrogen peroxide, it is also possible to use, as oxidizing agents, peracids, such as perbenzoic acid, monoperphthalic acid or 3-chloroperbenzoic acid. The reaction with peracids is expediently carried out in chlorinated hydrocarbons, such as methylene chloride or 1,2-dichloroethane.

Also very suitable for oxidizing the thiols to sulfoxides or sulfones are chorine and bromine. This oxidation is expediently carried out in polar solvents, such as water, acetonitrile, dioxane, or in two-phase systems, such as aqueous potassium bicarbonate solution/dichloromethane, and also acetic acid. It is furthermore possible to employ as source of active halogen tert-butyl hypochlorite, hypochlorous and hypobromous acids, their salts, and also N-halo compounds, such as N-bromo- and N-chlorosuccinimide or else sulfuryl chloride.

Also suitable for the oxidation is photosensitized oxygen transfer, in which case the photosensitizers used are usually organic dyes, for example porphyrines, such as tetraphenylphorphyrine, chlorophyll, protoporphyrine, xanthene dyes, such as rose Bengal, or phenothiazine dyes, such as methylene blue.

Suitable inert solvents are hydrocarbons, such as pentane, hexane, heptane, cyclohexane, chlorinated hydrocarbons, such as methylenechloride, 1,2-dichloroethane, 1,1,2,2-tetrachloroethane, alcohols, such as methanol, ethanol, n-propanol or isopropanol, ketones, such as acetone, methyl ethyl ketone, polar aprotic solvents such as acetonitrile, propionitrile, or aromatic hydrocarbons, such as benzene, toluene, chlorobenzene or xylene. In place of oxygen, it is also possible to use ozone in the abovementioned solvents, plus ether, 1,4-dioxane or THF.

Besides photosensitization, catalysts are also advisable for oxidation with oxygen, for example oxides and sulfides of nickel, copper, aluminum, tungsten, chromium, vanadium, ruthenium, titanium, manganese, molybdenum, magnesium and iron.

Either the sulfoxides I B or their sulfones I C are obtained, depending on the stoichiometry of the oxidizing agents used. The molar ratios in which the starting compounds are reacted with one another are generally 0.9 to 1.8, preferably 1.05 to 1.3, for the ratio of thiadiazine I A to oxidizing agent in the case of the oxidation to the sulfoxide and generally 1.9 to 3.5, preferably 2.05 to 2.9, in the case of oxidation to the sulfone.

The concentration of the starting materials in the solvent is generally 0.1 to 5 mol/l, preferably 0.2 to 2 mol/l.

It is advantageous to initially charge the 1-thiadiazine of the formula I where Z=S or the sulfoxide, if appropriate together with one of the abovementioned catalysts, in one of the abovementioned solvents, and then to add the oxidizing agent over the course of 0.25 to 20 hours with stirring. The addition and the reaction temperature depends on the optimum efficiency of the oxidizing agent in question and on avoiding side-reactions. If photosensitized oxygen is used, the reaction is generally carried out at from −20 to 80° C.; however, if metal catalysis is employed, the reaction is generally carried out at from 50 to 140° C., and if ozone is used, the reaction is generally carried out at from −78 to 60° C. Owing to the limited solubility of the oxygen derivatives, they are preferably introduced continuously into the reaction mixture over a relatively long period of time (up to 20 h) until the oxidation on the sulfoxide or sulfone stage has been completed. Liquid or easily soluble oxidizing agents, such as hydrogen peroxide, hypochlorous or hypobromous acid, tert-butyl hypochlorite, chlorite or bromine, furthermore N-chloro or N-bromosuccinimide, can be added to the reaction mixture of the thiadiazine or thiadiazine sulfoxide over shorter periods of time, such as 0.25 to 6 h, depending on the exothermic character of the reaction, and the reaction is ended after a further 1 to 60 h. Preference is furthermore given to adding the liquid or dissolved oxidizing agent gradually. In the case of hydrogen peroxide, the reaction is generally carried out at from 0 to 90° C., with tert-butyl hypochlorite, the reaction is generally carried out at from −78 to 30° C. and with N-halo compounds generally from 0 to 30° C. In the case of chlorine or bromine, a reaction temperature of from 0 to 40° C. is recommended.

The oxidations can be carried out under atmospheric or superatmospheric pressure, continuously or batchwise.

The multi-step reaction can advantageously also be carried out as a one-part process, where the thiadiazines I (Z=S) are converted directly, without isolation and purification, into the sulfoxides I (Z=SO) or the sulfones I (Z=SO$_2$). Accordingly, the reaction product Ia is, if appropriate, allowed to cool to from 90 to 20° C., a solvent, for example methylene chloride and/or water, is added, if appropriate, and the oxidizing agent is then added at the rate of its consumption. Particularly preferred oxidizing agents are hydrogen peroxide and sodium hypochlorite.

For work-up of the oxidation mixture, the end products I are generally taken up in a water-immiscible solvent, acidic impurities and/or oxidizing agents are extracted using dilute alkali or water, the mixture is dried and the solvent is removed under reduced pressure.

In principle, the substituted perhydrodiazines I can be prepared by the synthesis process according to the invention mentioned above. For economical or technical reasons, however, it may be more expedient to prepare some of the compounds I from similar substituted perhydrodiazines which differ in the meaning of one radical.

The work-up of the reaction mixtures is generally carried out by methods known per se, for example by dilution of the reaction solution with water and subsequent isolation of the product by filtration, crystallization or solvent extraction, or by removing the solvent, partitioning the residue in a mixture of water and suitable organic solvent and work-up of the organic phase to afford the product.

The compounds of the formula I according to the invention are obtainable in good yields. They can also be prepared on a relatively large scale. Accordingly, they are particularly suitable for use as starting materials for the preparation of compounds having a 1-hetero-3,4-diazine structure of the formula

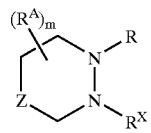

in which R, Z, R$^A$ and m are as defined above and R$^x$ is any organic radical.

It has now been found that compounds of the formula V

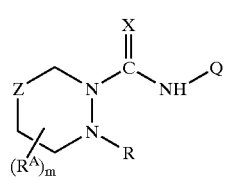

(V)

in which R, R$^A$, Z and m are as defined in claims 1 to 4,
X is O or S, and
Q is a C$_6$–C$_{14}$-aromatic radical which is at least mono-substituted and/or attached via two adjacent carbon atoms to a saturated or unsaturated 4- to 7-membered cycle which, in addition to the carbon ring members, may contain, if desired, one, two or three of the following members: —O—, —S—, —S(O)$_2$— —N=, —NH— or —N(C$_1$-C$_6$-alkyl)—;
have particularly good herbicidal activity. Such compounds are novel, and they form part of the subject matter of a further patent application.

It has been found that the compounds of the formula V can be prepared starting with the compounds of the formula I by reaction with isocyanates or isothiocyanates of the formula VI

Q—N=C=X in which Q and X are as defined above.

Accordingly, the present invention also relates to a process for preparing compounds of the formula V (substituted ureas) which comprises reacting the compounds of the formula I defined above with an isocyanate or isocyothianate of the formula VI.

With a view to the herbicidal activity of the substituted ureas of the formula V, Q is, for example, a radical Q1 to Q6:

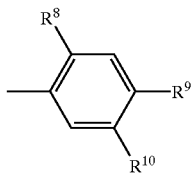

Q-1

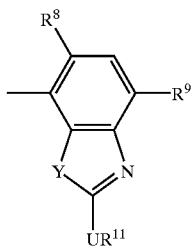

Q-2

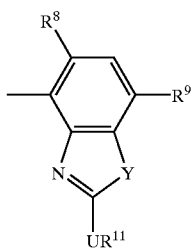

Q-3

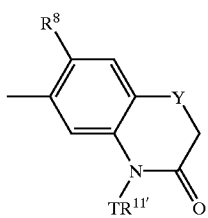

Q-4

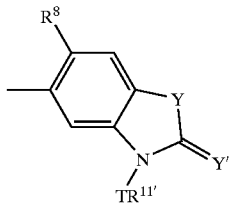

Q-5

-continued

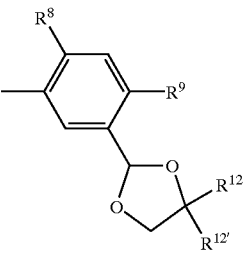

Q-6 in which

Y and Y' independently of one another are O or S;

T is a chemical bond or O;

U is a chemical bond, $C_1$–$C_4$-alkylene, O, S, SO or $SO_2$;

and the radicals $R^8$ to $R^{12'}$ are as defined below:

$R^8$ is hydrogen or halogen;

$R^9$ $C_1$–$C_6$-alkyl, $C_1$–$C_6$-haloalkyl, $OCH_3$, $SCH_3$, $OCHF_2$, halogen, cyano or $NO_2$;

$R^{10}$ is hydrogen, hydroxyl, mercapto, cyano, nitro, halogen, $C_1$–$C_6$-alkyl, $C_2$–$C_6$-alkenyl, $C_2$–$C_6$-alkynyl, $C_1$–$C_6$-haloalkyl, $C_1$–$C_6$-haloalkoxy, $C_1$–$C_6$-haloalkylthio, $C_1$–$C_6$-alkoxy-($C_1$–$C_6$-alkyl)carbonyl, $C_1$–$C_6$-alkylthio-($C_1$–$C_6$-alkyl)carbonyl, ($C_1$–$C_6$-alkyl)iminooxycarbonyl, $C_1$–$C_6$-alkoxy-$C_1$–$C_6$-alkyl, $C_1$–$C_6$-alkoxyamino-$C_1$–$C_6$-alkyl, $C_1$–$C_6$-alkoxy-$C_1$–$C_6$-alkylamino-$C_1$–$C_6$-alkyl, is $C_1$–$C_6$-alkoxy, $C_1$–$C_6$-alkylthio, $C_3$–$C_6$-cycloalkoxy, $C_3$–$C_6$-cycloalkylthio, $C_2$–$C_6$-alkenyloxy, $C_2$–$C_6$-alkenylthio, $C_2$–$C_6$-alkynyloxy, $C_2$–$C_6$-alkynylthio, ($C_1$–$C_6$-alkyl)carbonyloxy, ($C_1$–$C_6$-alkyl)carbonylthio, ($C_1$–$C_6$-alkoxy)carbonyloxy, ($C_2$–$C_6$-alkenyl)carbonyloxy, ($C_2$–$C_6$-alkenyl)carbonylthio, ($C_2$–$C_6$-alkynyl)carbonyloxy, ($C_2$–$C_6$-alkynyl)carbonylthio, $C_1$–$C_6$-alkylsulfonyloxy or $C_1$–$C_6$-alkylsulfonyl, where each of the 17 last-mentioned radicals may, if desired, carry one, two or three substituents, selected from the group consisting of: halogen, nitro, cyano, hydroxyl, $C_3$–$C_6$-cycloalkyl, $C_1$–$C_6$-alkoxy, $C_3$–$C_6$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminoxy, oxo, =N—$OR^{13}$;

phenyl, phenoxy or phenylsulfonyl, where the three last-mentioned groups may carry one, two or three substituents, selected from the group consisting of halogen, nitro cyano, $C_1$–$C_6$-alkyl, $C_1$–$C_6$-haloalkyl, $C_1$–$C_6$-alkoxy and ($C_1$–$C_6$-alkoxy)carbonyl;

CO—$R^{14}$, —CO—$OR^{14}$, —CO—$SR^{14}$, —CO—N($R^{14}$)—$R^{15}$, —OCO—$R^{14}$, —OCO—$OR^{14'}$, —OCO—$SR^{14'}$, —OCO—N($R^{14}$)—$R^{15}$, —N($R^{14}$)—$R^{15}$, and C($R^{16}$)=N—$OR^{13}$;

is C($Z^1$)—$R^{17}$, —C(=$NR^{18}$)$R^{17}$, C($R^{17}$)($Z^2R^{19}$)($Z^3R^{20}$) C($R^{17}$)=C($R^{21}$)—CN, C($R^{17}$)=C($R^{21}$)—CO—$R^{22}$, —CH($R^{17}$)—CH($R^{21}$)—COR$^{22}$, —C($R^{17}$)=C($R^{21}$)—$CH_2$—CO—$R^{22}$, —C($R^{17}$)=C($R^{21}$)—C($R^{23}$)=C($R^{24}$)—CO—$R^{22}$, —C($R^{17}$)=C($R^{21}$)—$CH_2$—CH($R^{25}$)—CO—$R^{22}$, —CO—$OR^{26}$, —CO—$SR^{26}$, —CON($R^{26}$)—$OR^{13}$, —C≡C—CO—$NHOR^{13}$, —C≡C—CO—N($R^{26}$)—$OR^{13}$, —C≡C—CS—NH—$OR^{13}$, —C=C—CS—N($R^{26}$)—$OR^{13}$, —C($R^{17}$)=C($R^{21}$)—CO—$NHOR^{13}$, —C($R^{17}$)=C($R^{21}$)—CO—

$N(R^{26})$—$OR^{13}$, —$C(R^{17})$=$C(R^{21})$—CS—$NHOR^{13}$, —$C(R^{17})$=$C(R^{21})$—CS—$N(R^{26})$—$OR^{13}$, —$C(R^{17})$=$C(R^{21})$—$C(R^{16})$=N—$OR^{13}$, $C(R^{16})$=N—$OR^{13}$, —C≡C—$C(R^{16})$=$NOR^{13}$, $C(Z^2R^{19})(Z^3R^{20})$—$OR^{26}$, —$C(Z^2R^{19})(Z^2R^{20})SR^{26}$, $C(Z^2R^{19})(Z^3R^{20})$—$N(R^{27})R^{28}$, —$N(R^{27})$—$R^{28}$, —CO—$N(R^{27})$—$R^{28}$ or $C(R^{17})$=$C(R^{21})CO$—$N(R^{27})R^{28}$; where $Z^1$, $Z^2$ and $Z^3$ independently of one another are oxygen or sulfur;

$R^{11}$ is hydrogen, $C_1$–$C_6$-alkyl, $C_1$–$C_6$-haloalkyl, $C_1$–$C_3$-alkoxy-$C_1$–$C_3$-alkyl, $C_3$–$C_6$-alkenyl, $C_1$–$C_3$-alkoxy-$C_3$–$C_6$-alkenyl, $C_3$–$C_6$-haloalkenyl, $C_3$–$C_6$-alkynyl, $C_1$–$C_3$-alkoxy-$C_3$–$C_6$-alkynyl, $C_3$–$C_6$-haloalkynyl, $C_3$–$C_7$-cycloalkyl, 3- to 7-membered saturated heterocyclyl, where each cycloalkyl and each heterocyclyl ring may contain a carbonyl or thiocarbonyl ring member and where each cycloalkyl and heterocyclyl ring may be unsubstituted or may carry one, two, three or four substituents, selected from the group consisting of cyano, nitro, amino, hydroxyl, halogen, $C_1$–$C_4$-alkyl, $C_1$–$C_4$-haloalkyl, $C_1$–$C_4$-cyanoalkyl, $C_1$–$C_4$-hydroxyalkyl, $C_1$–$C_4$-aminoalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfinyl, $C_1$–$C_4$-alkylsulfonyl, $C_1$–$C_4$-haloalkylsulfonyl, ($C_1$–$C_4$-alkoxy)carbonyl, ($C_1$–$C_4$-alkyl)carbonyl, ($C_1$–$C_4$-haloalkyl)carbonyl, ($C_1$–$C_4$-alkyl)carbonyloxy, ($C_1$–$C_4$-haloalkyl)carbonyloxy, di($C_1$–$C_4$-alkyl)amino, $C_3$–$C_6$-alkenyl, $C_3$–$C_6$-alkynyl, $C_3$–$C_4$-alkenyloxy, $C_3$–$C_4$-alkenylthio, $C_3$–$C_4$-alkynyloxy and $C_3$–$C_4$-alkynylthio;

$R^{11'}$ is hydrogen, $C_1$–$C_6$-alkyl, $C_1$–$C_6$-haloalkyl, $C_1$–$C_3$-alkoxy-$C_1$–$C_3$-alkyl, $C_2$–$C_6$-cyanoalkyl, $C_3$–$C_6$-alkenyl, $C_3$–$C_6$-alkynyl;

$R^{12}$ is hydrogen, $C_1$–$C_3$-alkyl, $C_1$–$C_3$-haloalkyl or halogen;

$R^{12'}$ is hydrogen, $C_1$–$C_3$-alkyl, $C_1$–$C_3$-haloalkyl; or $R^{12}$ and $R^{12'}$ together are C=O.

The variables $R^{13}$ to $R^{30}$ listed under $R^{10}$ have, for example, the following meanings:

$R^{13}$ is hydrogen, $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl, hydroxy-$C_1$–$C_6$-alkyl, $C_1$–$C_6$-alkoxy-$C_1$–$C_6$-alkyl, $C_1$–$C_6$-alkylthio-$C_1$–$C_6$-alkyl, cyano-$C_1$–$C_6$-alkyl, ($C_1$–$C_6$-alkyl)carbonyl-$C_1$–$C_6$-alkyl, ($C_1$–$C_6$-alkoxy)carbonyl-$C_1$–$C_6$-alkyl, ($C_1$–$C_6$-alkoxy)carbonyl-$C_2$–$C_6$-alkenyl, ($C_1$–$C_6$-alkyl)carbonyloxy-$C_1$–$C_6$-alkyl or phenyl-$C_1$–$C_6$-alkyl, in which the phenyl ring may, if desired, carry one, two or three substituents, selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl;

$R^{14}$ is hydrogen, $C_1$–$C_6$-alkyl, $C_3$–$C_6$-cycloalkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkoxy)carbonyl-$C_1$–$C_6$-alkyl, ($C_3$–$C_6$-alkenyloxy)carbonyl-$C_1$–$C_6$-alkyl, phenyl or phenyl-$C_1$–$C_6$-alkyl, where the phenyl ring of the two last-mentioned groups may be unsubstituted or may carry one, two or three radicals, selected from the group consisting of halogen, nitro, cyano, $C_1$–$C_6$-alkyl, $C_1$–$C_6$-haloalkyl, $C_1$–$C_6$-alkoxy and ($C_1$–$C_6$-alkyl)carbonyl;

$R^{14'}$ has the meanings of $R^{14}$ with the exception of hydrogen;

$R^{15}$ is hydrogen, hydroxyl, $C_1$–$C_6$-alkyl $C_3$–$C_6$-cycloalkyl, $C_1$–$C_6$-alkoxy, ($C_1$–$C_6$-alkoxy)carbonyl-$C_1$–$C_6$-alkoxy, $C_3$–$C_6$-alkenyl or $C_3$–$C_6$-alkenyloxy;

$R^{16}$ is hydrogen, halogen, $C_1$–$C_6$-alkyl, $C_1$–$C_6$-haloalkyl, $C_1$–$C_6$-alkoxy, $C_1$–$C_6$-haloalkoxy, $C_3$–$C_6$-alkenyloxy, $C_3$–$C_6$-alkynyloxy, $C_1$–$C_6$-alkylthio, $C_1$–$C_6$-haloalkylthio, ($C_1$–$C_6$-alkyl)carbonyloxy, ($C_1$–$C_6$-haloalkyl)carbonyloxy, $C_1$–$C_6$-alkylsulfonyloxy or $C_1$–$C_6$-haloalkylsulfonyloxy, where the 12 last-mentioned radicals may carry one of the following substituents: hydroxyl, cyano, hydroxycarbonyl, $C_1$–$C_6$-alkoxy, $C_1$–$C_6$-alkylthio, ($C_1$–$C_6$-alkyl)carbonyl, ($C_1$–$C_6$-alkoxy)carbonyl, ($C_1$–$C_6$-alkyl)aminocarbonyl, di($C_1$–$C_6$-alkyl)aminocarbonyl, ($C_1$–$C_6$-alkyl)carbonyloxy, $C_1$–$C_6$-alkoxy-($C_1$–$C_6$-alkyl)aminocarbonyl;

is ($C_1$–$C_6$-alkyl)carbonyl, ($C_1$–$C_6$-haloalkyl)carbonyl, ($C_1$–$C_6$-alkoxy)carbonyl, ($C_1$–$C_6$-alkoxy)carbonyloxy, ($C_1$–$C_6$-alkyl)carbonylthio, ($C_1$–$C_6$-haloalkyl)carbonylthio, ($C_1$–$C_6$-alkoxy)carbonylthio, $C_2$–$C_6$-alkenyl, ($C_2$–$C_6$-alkenyl)carbonyloxy, $C_2$–$C_6$-alkenylthio, $C_3$–$C_6$-alkynyl, $C_3$–$C_6$-alkynyloxy, $C_3$–$C_6$-alkynylthio, ($C_2$–$C_6$-alkynyl)carbonyloxy, $C_3$–$C_6$-alkynylsulfonyoxy, $C_3$–$C_6$-cycloalkyl, $C_3$–$C_6$-cycloalkyloxy, $C_3$–$C_6$-cycloalkylthio, ($C_3$–$C_6$-cycloalkyl)carbonyloxy, $C_3$–$C_6$-cycloalkylsulfonyloxy;

is phenyl, phenoxy, phenylthio, benzoyloxy, phenylsulfonyloxy, phenyl-$C_1$–$C_6$-alkyl, phenyl-$C_1$–$C_6$-alkoxy, phenyl-$C_1$–$C_6$-alkylthio, phenyl-($C_1$–$C_6$-alkyl)carbonyloxy or phenyl-($C_1$–$C_6$-alkyl)sulfonyloxy, where the phenyl rings of the 10 last-mentioned radicals may be unsubstituted or may for their part carry one to three substituents, in each case selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl;

$R^{17}$ is hydrogen, cyano, $C_1$–$C_6$-alkyl, $C_1$–$C_6$-haloalkyl, $C_2$–$C_6$-alkenyl, $C_2$–$C_6$-alkynyl, $C_3$–$C_6$-cycloalkyl, $C_1$–$C_6$-alkoxy-$C_1$–$C_6$-alkyl or ($C_1$–$C_6$-alkoxy)carbonyl;

$R^{18}$ is hydrogen, hydroxyl, $C_1$–$C_6$-alkyl, $C_3$–$C_6$-alkenyl, $C_3$–$C_6$-alkynyl, $C_3$–$C_6$-cycloalkyl, $C_1$–$C_6$-haloalkyl, $C_1$–$C_6$-alkoxy-$C_1$–$C_6$-alkyl, $C_1$–$C_6$-alkoxy, $C_3$–$C_6$-alkenyloxy, $C_3$–$C_6$-alkynyloxy, $C_3$–$C_6$-cycloalkoxy, $C_5$–$C_7$-cycloalkenyloxy, $C_1$–$C_6$-haloalkoxy, $C_3$–$C_6$-haloalkenyloxy, hydroxy-$C_1$–$C_6$-alkoxy, cyano-$C_1$–$C_6$-alkoxy, $C_3$–$C_6$-cycloalkyl-$C_1$–$C_6$-alkoxy, $C_1$–$C_6$-alkoxy-$C_1$–$C_6$-alkoxy, $C_1$–$C_6$-alkoxy-$C_3$–$C_6$-alkenyloxy, ($C_1$–$C_6$-alkyl)carbonyloxy, ($C_1$–$C_6$-haloalkyl)carbonyloxy, ($C_1$–$C_6$-alkyl)carbamoyloxy, ($C_1$–$C_6$-haloalkyl)carbamoyloxy, ($C_1$–$C_6$-alkyl)carbonyl-$C_1$–$C_6$-alkyl, ($C_1$–$C_6$-alkyl)carbonyl-$C_1$–$C_6$-alkoxy, ($C_1$–$C_6$-alkoxy)carbonyl-$C_1$–$C_6$-alkyl, ($C_1$–$C_6$-alkoxy)carbonyl-$C_1$–$C_6$-alkoxy, $C_1$–$C_6$-alkylthio-$C_1$–$C_6$-alkoxy, di($C_1$–$C_6$-alkyl)amino-$C_1$–$C_6$-alkoxy, —$N(R^{29})R^{30}$, phenyl, which for its part may carry one, two or three substituents, in each case selected from the group consisting of cyano, nitro, halogen, $C_1$–$C_6$-alkyl, $C_1$–$C_6$-haloalkyl, $C_2$–$C_6$-alkenyl, $C_1$–$C_6$-alkoxy and ($C_1$–$C_6$-alkoxy)carbonyl;

is phenyl-$C_1$–$C_6$-alkoxy, phenyl-$C_1$–$C_6$-alkyl, phenyl-$C_3$–$C_6$-alkenyloxy or phenyl-$C_3$–$C_6$-alkynyloxy, where in each case one or two methylene groups of the carbon chains in the four last-mentioned groups may be replaced by —O—, —S—, or —$N(C_1$–$C_6$-alkyl)—, and where the phenyl rings in the four last-mentioned groups may be unsubstituted or may for their part carry one to three substituents, selected from the group consisting of cyano, nitrogen, halogen, $C_1$–$C_6$-alkyl, $C_1$–$C_6$-haloalkyl, $C_2$–$C_6$-alkenyl, $C_1$–$C_6$-alkoxy and ($C_1$–$C_6$-alkoxy)carbonyl; is $C_3$–$C_7$-heterocyclyl, $C_3$–$C_7$-heterocyclyl-$C_1$–$C_6$-alkyl, $C_3$–$C_7$-heterocyclyl-$C_1$–$C_6$-alkoxy, $C_3$–$C_7$-heterocyclyl-$C_3$–$C_6$-alkenyloxy or $C_3$–$C_7$-heterocyclyl-$C_3$–$C_6$-alkynyloxy, where in each case one or two methylene groups of the carbon chains in the four last-mentioned groups may be replaced by —O—, —S— or —N($C_1$–$C_6$-alkyl)— and where each heterocycle may be saturated, unsaturated or aromatic and is either unsubstituted or for its part carries one to three substituents, selected from the group consisting of cyano, nitro, halogen, $C_1$–$C_6$-alkyl, $C_1$–$C_6$-haloalkyl, $C_2$–$C_6$-alkenyl, $C_1$–$C_6$-alkoxy and ($C_1$–$C_6$-alkoxy)carbonyl;

$R^{19}$, $R^{20}$ independently of one another are $C_1$–$C_6$-alkyl, $C_1$–$C_6$-haloalkyl, $C_3$–$C_6$-alkenyl, $C_3$–$C_6$-alkynyl, $C_1$–$C_6$-alkoxy-$C_1$–$C_6$-alkyl or together are a saturated or unsaturated, 2- to 4-membered carbon chain which may carry one oxo substituent, where one member of this chain which is not adjacent to the variables $Z^2$ and $Z^3$ may be replaced by —O—, —S—, —N=, —NH— or —N($C_1$–$C_6$-alkyl)— and where the carbon chain may carry one to three radicals selected from the group consisting of cyano, nitro, amino, halogen, $C_1$–$C_6$-alkyl, $C_2$–$C_6$-alkenyl, $C_1$–$C_6$-alkoxy, $C_2$–$C_6$-alkenyloxy, $C_2$–$C_6$-alkynyloxy, $C_1$–$C_6$-haloalkyl, cyano-$C_1$–$C_6$-alkyl, hydroxy-$C_1$–$C_6$-alkyl, $C_1$–$C_6$-alkoxy-$C_1$–$C_6$-alkyl, $C_3$–$C_6$-alkenyloxy-$C_1$–$C_6$-alkyl, $C_3$–$C_6$-alkynyloxy-$C_1$–$C_6$-alkyl, $C_3$–$C_6$-cycloalkyl, $C_3$–$C_6$-cycloalkoxy, carboxyl, ($C_1$–$C_6$-alkoxy)carbonyl, ($C_1$–$C_6$-alkyl)carbonyloxy-$C_1$–$C_6$-alkyl and phenyl; unsubstituted or substituted phenyl where the carbon chain may also be substituted by a fused-on or spiro-linked 3- to 7-membered ring which may contain one or two hetero atoms as ring members, selected from the group consisting of oxygen, sulfur, nitrogen and $C_1$–$C_6$-alkyl-substituted nitrogen, and which, for its part, may, if desired, carry one or two of the following substituents: cyano, $C_1$–$C_6$-alkyl, $C_2$–$C_6$-alkenyl, $C_1$–$C_6$-alkoxy, cyano-$C_1$–$C_6$-alkyl, $C_1$–$C_6$-haloalkyl and ($C_1$–$C_6$-alkoxy)carbonyl;

$R^{21}$ is hydrogen, cyano, halogen, $C_1$–$C_6$-alkyl, $C_1$–$C_6$-haloalkyl, $C_1$–$C_6$-alkoxy, ($C_1$–$C_6$-alkyl)carbonyl or ($C_1$–$C_6$-alkoxy)carbonyl;

$R^{22}$ is hydrogen, O—$R^{31}$, S—$R^{31}$, $C_1$–$C_6$-alkyl, which may carry one or two $C_1$–$C_6$-alkoxy substituents, $C_2$–$C_6$-alkenyl, $C_2$–$C_6$-alkynyl, $C_1$–$C_6$-haloalkyl, $C_3$–$C_6$-cycloalkyl, $C_1$–$C_6$-alkylthio-$C_1$–$C_6$-alkyl, $C_1$–$C_6$-alkyliminooxy, —N($R^{27}$)$R^{28}$ or phenyl, which may be unsubstituted or may carry one to three substituents, in each case selected from the group consisting of cyano, nitro, halogen, $C_1$–$C_6$-alkyl, $C_2$–$C_6$-alkenyl, $C_1$–$C_6$-haloalkyl, $C_1$–$C_6$-alkoxy and ($C_1$–$C_6$-alkoxy)carbonyl;

$R^{23}$ is hydrogen, cyano, halogen, $C_1$–$C_6$-alkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkyl)carbonyl, ($C_1$–$C_6$-alkoxy)carbonyl, —N($R^{27}$)$R^{28}$ or phenyl, which for its part may carry one to three substituents, selected from the group consisting of cyano, nitro, halogen, $C_1$–$C_6$-alkyl, $C_1$–$C_6$-haloalkyl, $C_3$–$C_6$-alkenyl, $C_1$–$C_6$-alkoxy and ($C_1$–$C_6$-alkoxy)carbonyl;

$R^{24}$ is hydrogen, cyano, halogen, $C_1$–$C_6$-alkyl, $C_1$–$C_6$-alkoxy, $C_1$–$C_6$-haloalkyl, ($C_1$–$C_6$-alkyl)carbonyl or ($C_1$–$C_6$-alkoxy)carbonyl;

$R^{25}$ is hydrogen, cyano, $C_1$–$C_6$-alkyl or ($C_1$–$C_6$-alkoxy)carbonyl;

$R^{26}$, $R^{31}$ independently of one another are hydrogen, $C_1$–$C_6$-alkyl, $C_1$–$C_6$-haloalkyl, $C_2$–$C_6$-alkenyl or $C_2$–$C_6$-alkynyl, where the 4 last-mentioned groups may in each case carry one or two of the following radicals: cyano, halogen, hydroxyl, hydroxycarbonyl, $C_1$–$C_6$-alkoxy, $C_1$–$C_6$-alkylthio, ($C_1$–$C_6$-alkyl)carbonyl, ($C_1$–$C_6$-alkoxy)carbonyl, ($C_1$–$C_6$-alkyl)carbonyloxy, ($C_3$–$C_6$-alkenyloxy)carbonyl;

are ($C_1$–$C_6$-haloalkyl)carbonyl, ($C_1$–$C_6$-alkoxy)carbonyl, $C_1$–$C_6$-alkylaminocarbonyl, di($C_1$–$C_6$-alkyl)aminocarbonyl, $C_1$–$C_6$-alkyloximino-$C_1$–$C_6$-alkyl, $C_3$–$C_6$-cycloalkyl;

are phenyl or phenyl-$C_1$–$C_6$-alkyl, where the phenyl rings may be unsubstituted or may for their part carry one to three substituents, in each case selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl;

$R^{27}$, $R^{28}$, $R^{29}$, $R^{30}$ independently of one another are hydrogen, $C_1$–$C_6$-alkyl, $C_3$–$C_6$-alkenyl, $C_2$–$C_6$-alkynyl, $C_3$–$C_6$-cycloalkyl, $C_1$–$C_6$-haloalkyl, $C_1$–$C_6$-alkoxy-$C_1$–$C_6$-alkyl, ($C_1$–$C_6$-alkyl)carbonyl, ($C_1$–$C_6$-alkoxy)carbonyl, ($C_1$–$C_6$-alkoxy)carbonyl-$C_1$–$C_6$-alkyl, are ($C_1$–$C_6$-alkoxy)carbonyl-$C_2$–$C_6$-alkenyl, where the alkenyl chain may additionally carry one to three halogen and/or cyano radicals, are $C_1$–$C_6$-alkylsulfonyl, ($C_1$–$C_6$-alkoxy)carbonyl-$C_1$–$C_6$-alkylsulfonyl, phenyl or phenylsulfonyl, where the phenyl rings of the two last-mentioned radicals may be unsubstituted or for their part may carry one to three substituents, in each case selected from the group consisting of cyano, nitro, halogen, $C_1$–$C_6$-alkyl, $C_1$–$C_6$-haloalkyl, $C_3$–$C_6$-alkenyl, $C_1$–$C_6$-alkoxy and ($C_1$–$C_6$-alkoxy)carbonyl; or $R^{27}$ and $R^{28}$ and/or $R^{29}$ and $R^{30}$ in each case together with the common nitrogen atom are a saturated or unsaturated 4- to 7-membered azo heterocycle, which in addition to carbon ring members, may, if desired, contain one of the following members:

—O—, —S—, —N=, —NH— or —N($C_1$–$C_6$-alkyl)—.

With a view to the use of the substituted ureas of the formula V as herbicides, the variables preferably have the following meanings, in each case on their own or in combination.

Z is O or S;

$R^A$ is $CO_2R^1$, halogen, cyano, $OR^2$ or $C_1$–$C_3$-alkyl;

Q is Q-1, Q-2 or Q-4;

X, Y and Y' independently of one another are O or S;

T is a chemical bond or O;

U is a chemical bond, $C_1$–$C_4$-alkylene, O or S;

R is $C(O)OR^3$, $C(O)SR^3$, $C(S)OR^3$, $C(S)SR^3$, CHO, CN, $C(O)R^2$, $C(O)NR^4R^5$, $C(S)NR^4R^5$, $C(O)NHC(O)_2OR^6$, $C(O)NHS(O)_2R^6$, $C(O)NHS(O)_2OR^6$;

$R^1$ is hydrogen or $C_1$–$C_3$-alkyl;

$R^2$ is $C_1$–$C_3$-alkyl, $C_3$–$C_6$-cycloalkyl, $C_3$–$C_6$-alkenyl, $C_3$–$C_6$-alkynyl, $C_1$–$C_3$-haloalkyl, $C_1$–$C_3$-alkoxycarbonyl-$C_1$–$C_3$-alkyl, cyano-$C_1$–$C_3$-alkyl, benzyl, which may be substituted by halogen, $C_1$–$C_4$-alkyl or trifluoromethyl, or is phenyl, which may be substituted by halogen, $C_1$–$C_4$-alkyl, trifluoromethyl or $C_1$–$C_4$-alkoxy;

$R^3$ is $C_1-C_{15}$-alkyl, $C_3-C_8$-cycloalkyl, $C_2-C_{10}$-alkenyl, $C_3-C_{10}$-alkynyl, $C_1-C_6$-haloalkyl, $C_1-C_6$-alkoxy-$C_1-C_6$-alkyl, $C_1-C_6$-alkoxycarbonyl-$C_1-C_6$-alkyl, $C_3-C_6$-alkenyloxy-$C_1-C_6$-alkyl, $C_3-C_6$-alkynyloxy-$C_1-C_6$-alkyl, cyano-$C_1-C_6$-alkyl, is phenyl or benzyl, which may in each case be mono- to pentasubstituted by halogen, $C_1-C_4$-alkyl, $C_1-C_4$-haloalkyl, $C_1-C_4$-alkoxy, $C_1-C_4$-haloalkoxy, amino, $C_2-C_4$-monoalkylamino, $C_1-C_4$-dialkylamino, $C_1-C_4$-alkoxycarbonyl, nitro or cyano;

$R^4$ is hydrogen, $C_1-C_6$-alkyl or $C_1-C_6$-alkoxy;

$R^5$, $R^6$ independently of one another are hydrogen, $C_1-C_6$-alkyl, $C_2-C_6$-alkenyl, $C_2-C_6$-alkynyl, $C_1-C_6$-haloalkyl, $C_1-C_6$-alkoxy-$C_1-C_6$-alkyl, phenyl or benzyl, which may be mono- to pentasubstituted by halogen, $C_1-C_4$-alkyl, $C_1-C_4$-haloalkyl, $C_1-C_4$-alkoxy, $C_1-C_4$-dialkylamino, $C_1-C_4$-alkoxycarbonyl, nitro or cyano; or $R^4$ and $R^5$ together with the common nitrogen atom are a saturated or unsaturated 4- to 7-membered azo heterocycle $R^8$ is hydrogen, fluorine or chlorine;

$R^9$ is chlorine, trifluoromethyl or cyano;

$R^{10}$ is hydrogen, hydroxyl, mercapto, cyano, nitro, halogen, $C_1-C_6$-alkyl, $C_1-C_6$-haloalkyl, $C_1-C_6$-haloalkoxy, $C_1-C_6$-haloalkylthio, $C_1-C_6$-alkoxy-$(C_1-C_6$-alkyl)carbonyl, $C_1-C_6$-alkylthio-$(C_1-C_6$-alkyl)carbonyl, $(C_1-C_6$-alkyl)iminooxycarbonyl, $C_1-C_6$-alkoxy-$C_1-C_6$-alkyl, $C_1-C_6$-alkoxyamino-$C_1-C_6$-alkyl, $C_1-C_6$-alkoxy-$C_1-C_6$-alkylamino-$C_1-C_6$-alkyl, is $C_1-C_6$-alkoxy, $C_1-C_6$-alkylthio, $C_3-C_6$-cycloalkoxy, $C_3-C_6$-Cycloalkylthio, $C_2-C_6$-alkenyloxy, $C_2-C_6$-alkenylthio, $C_2-C_6$-alkynyloxy, $C_2-C_6$-alkynylthio, $(C_1-C_6$-alkyl)carbonyloxy, $(C_1-C_6$-alkyl)carbonylthio, $(C_1-C_6$-alkoxy)carbonyloxy, $(C_2-C_6$-alkenyl)carbonyloxy, $(C_2-C_6$-alkenyl)carbonylthio, $(C_2-C_6$-alkynyl)carbonyloxy, $(C_2-C_6$-alkynyl)carbonylthio, $C_1-C_6$-alkylsulfonyloxy or $C_1-C_6$-alkylsulfonyl, where each of these 17 radicals may, if desired, carry one, two or three substituents, selected from the group consisting of:

halogen, nitro, cyano, hydroxyl, $C_3-C_6$-cycloalkyl, $C_1-C_6$-alkoxy, $C_3-C_6$-cycloalkoxy, $C_3-C_6$-alkenyloxy, $C_3-C_6$-alkynyloxy, $C_1-C_6$-alkoxy-$C_1-C_6$-alkoxy, $C_1-C_6$-alkylthio, $C_1-C_6$-alkylsulfinyl, $C_1-C_6$-alkylsulfonyl, $C_1-C_6$-alkylideneaminoxy, oxo, $=N-OR^{13}$ phenyl, phenoxy or phenylsulfonyl, where the three last-mentioned substituents for their part may carry one, two or three substituents, in each case selected from the group consisting of halogen, nitro, cyano, $C_1-C_6$-alkyl, $C_1-C_6$-haloalkyl, $C_1-C_6$-alkoxy and $(C_1-C_6$-alkoxy)carbonyl;

$-CO-R^{14}$, $-CO-OR^{14}$, $-CO-SR^{14}$, $-CO-N(R^{14})-R^{15}$, $-OCO-R^{14}$, $-OCO-OR^{14'}$, $-OCO-SR^{14'}$, $-OCO-N(R^{14})-R^{15}$, $-N(R^{14})-R^{15}$ and $-C(R^{16})=N-OR^{13}$;

is $C(Z^{1)-R17}$, $-C(=NR^{18})R^{17}$, $C(R^{17})(Z^2R^{19})(Z^3R^{20})$ $C(R^{17})=C(R^{21})-CN$, $C(R^{17})=C(R^{21})-CO-R^{22}$, $-CH(R^{17})-CH(R^{21})-COR^{22}$, $-C(R^{17})=C(R^{21})-CH_2-CO-R^{22}$, $-C(R^{17})=C(R^{21})-C(R^{23})=C(R^{24})-CO-R^{22}$, $-C(R^{17})=C(R^{21})-CH_2-CH(R^{25})-CO-R^{22}$, $-CO-OR^{26}$, $-CO-SR^{26}$, $-CON(R^{26})-OR^{13}$, $-C\equiv C-CO-NHOR^{13}$, $-C\equiv C-C-CO-N(R^{26})-OR^{13}$, $-C\equiv C-C-NH-OR^{13}$, $-C\equiv C-CS-N(R^{26})-OR^{13}$, $-C(R^{17})=C(R^{21})-CO-NHOR^{13}$, $-C(R^{17})=C(R^{21})-CO-N(R^{26})-OR^{13}$, $-C(R^{17})=C(R^{21})-CS-NHOR^{13}$, $-C(R^{17})=C(R^{21})-CS-N(R^{26})-OR^{13}$, $-C(R^{17})=C(R^{21})-C(R^{16})=N-OR^{13}$, $C(R^{16})=N-OR^{13}$, $-C\equiv C-C(R^{16})=NOR^{13}$, $C(Z^2R^{19})(Z^3R^{20})-OR^{26}$, $-C(Z^2R^{19})(Z^3R^{20})SR^{26}$, $C(Z^2R^{19})(Z^3R^{20})-N(R^{27})R^{28}$, $-N(R^{27})-R^{28}$, $-CO-N(R^{27})-R^{28}$ or $C(R^{17})=C(R^{21})CO-N(R^{27})R^{28}$; where $Z^1$, $Z^2$, $Z^3$ independently of one another are oxygen or sulfur;

$R^{11}$ is hydrogen, $C_1-C_6$-alkyl, $C_1-C_6$-haloalkyl, $C_3-C_6$-alkenyl, $C_3-C_6$-alkynyl, $C_3-C_7$-cycloalkyl, or 3- to 7-membered saturated heterocyclyl containing one or more oxygen and/or sulfur atoms;

$R^{11'}$ is hydrogen or $C_1-C_6$-alkyl;

$R^{12}$ is hydrogen or $C_1-C_3$-alkyl;

$R^{12'}$ is hydrogen, $C_1-C_3$-alkyl;

$R^{12}$ and $R^{12'}$ together are $C=O$;

$R^{13}$ is hydrogen, $C_1-C_6$-alkyl, $C_1-C_6$-haloalkyl, $C_3-C_6$-cycloalkyl, $C_3-C_6$-alkenyl, $C_3-C_6$-alkynyl, $C_1-C_6$-alkoxy-$C_1-C_6$-alkyl, cyano-$C_1-C_6$-alkyl, $(C_1-C_6$-alkoxy)carbonyl-$C_1-C_6$-alkyl or phenylalkyl, where the phenyl ring may be mono- to trisubstituted by halogen, cyano, nitro, $C_1-C_3$-alkyl, $C_1-C_3$-haloalkyl or $C_1-C_3$-alkoxy;

$R^{14}$ is hydrogen, $C_1-C_6$-alkyl, $C_3-C_6$-cycloalkyl, $C_3-C_6$-alkenyl, $C_3-C_6$-alkynyl, $C_1-C_6$-alkoxy-$C_1-C_6$-alkyl, $(C_1-C_6$-alkoxy)carbonyl-$C_1-C_6$-alkyl, $(C_1-C_6$-alkenyloxy)carbonyl-$C_1-C_6$-alkyl, is phenyl or benzyl, which may be unsubstituted at the phenyl ring or mono to trisubstituted by halogen, cyano, nitro, $C_1-C_3$-alkyl, $C_1-C_3$-haloalkyl or $C_1-C_3$-alkoxy;

$R^{14'}$ has the meanings of $R^{14}$ with the exception of hydrogen;

$R^{15}$ is hydrogen, hydroxyl, $C_1-C_6$-alkyl, $C_1-C_6$-alkoxy, $(C_1-C_3$-alkoxy)carbonyl-$C_1-C_3$-alkoxy, $C_3-C_6$-alkenyl or $C_3-C_6$-alkynyl;

$R^{16}$ is hydrogen, halogen, $C_1-C_6$-alkyl, $C_1-C_6$-haloalkyl, $C_1-C_6$-alkoxy, $C_3-C_6$-alkenyloxy, $(C_1-C_6$-alkoxy)carbonylalkoxy, $C_2-C_6$-alkenyl, $(C_2-C_6$-alkenyl)carbonyloxy, $C_3-C_6$-alkynyl, $(C_2-C_6$-alkynyl)carbonyloxy, is phenyl, phenoxy or benzyl, where the phenyl rings of the 3 last-mentioned radicals may be unsubstituted or mono- to trisubstituted by halogen, cyano, nitro, $C_1-C_3$-alkyl, $C_1-C_3$-haloalkyl, $C_1-C_3$-alkoxy or $(C_1-C_3$-alkoxy)carbonyl;

$R^{17}$ is hydrogen, cyano, $C_1-C_6$-alkyl, $C_1-C_6$-haloalkyl, $C_2-C_6$-alkenyl, $C_2-C_6$-alkynyl, $C_1-C_6$-alkoxy-$C_1-C_6$-alkyl or $(C_1-C_6$-alkoxy)carbonyl;

$R^{18}$ is hydrogen, $C_1-C_6$-alkyl, $C_3-C_6$-alkenyl, $C_3-C_6$-alkynyl, $C_3-C_6$-cycloalkyl, $C_1-C_6$-haloalkyl, $C_1-C_6$-alkoxy-$C_1-C_6$-alkyl, $C_1-C_6$-alkoxy, $(C_1-C_6$-alkoxy)carbonyl-$C_1-C_6$-alkyl, is phenyl or phenyl-$(C_1-C_6$-alkyl), where the two last-mentioned phenyl radicals may be substituted by halogen, cyano, nitro, $C_1-C_3$-alkyl, $C_1-C_3$-haloalkyl, $C_1-C_3$-alkoxy or $(C_1-C_3$-alkoxy)carbonyl;

$R^{19}$, $R^{20}$ independently of one another are $C_1-C_6$-alkyl, $C_1-C_6$-haloalkyl, $C_3-C_6$-alkenyl, $C_3-C_6$-alkynyl, $C_1-C_6$-alkoxy-$C_1-C_6$-alkyl, or $R^{19}$ and $R^{20}$ together are a saturated 2- to 4-membered carbon chain which may carry an oxo substituent, where a carbon atom of this chain which is not adjacent to the variables $Z^2$ and $Z^3$ may be replaced by —O—, —S—, —N=, —NH— or —N($C_1$–$C_6$-alkyl)—, and where the carbon chain may be mono- to trisubstituted by halogen or $C_1$–$C_6$-alkyl;

$R^{21}$ is hydrogen, cyano, halogen, $C_1$–$C_6$-alkyl, $C_1$–$C_6$-haloalkyl or $C_1$–$C_6$-alkoxy;

$R^{22}$ is hydrogen, $OR^{31}$, S—$R^{31}$, $C_1$–$C_6$-alkyl, which may carry one or two $C_1$–$C_6$-alkoxy substituents, is $C_2$–$C_6$-alkenyl, $C_2$–$C_6$-alkynyl, $C_1$–$C_6$-haloalkyl or $C_3$–$C_6$-cycloalkyl;

$R^{23}$ is hydrogen, cyano, halogen, $C_1$–$C_6$-alkyl, $C_3$–$C_6$-alkenyl or $C_3$–$C_6$-alkynyl;

$R^{24}$ is hydrogen, cyano, halogen, $C_1$–$C_6$-alkyl, $C_1$–$C_6$-alkoxy or $C_1$–$C_6$-haloalkyl;

$R^{25}$ is hydrogen, cyano or $C_1$–$C_6$-alkyl;

$R^{26}$, $R^{31}$ independently of one another are hydrogen, $C_1$–$C_6$-alkyl, $C_1$–$C_6$-haloalkyl, $C_2$–$C_6$-alkenyl or $C_2$–$C_6$-alkynyl, where the 4 last-mentioned groups may in each case carry one or two of the following radicals: cyano, halogen, $C_1$–$C_6$-alkoxy, $C_1$–$C_6$-alkylcarbonyl, ($C_1$–$C_6$-alkoxy)carbonyl;
  or are ($C_1$–$C_6$-alkyl)carbonyl, ($C_1$–$C_6$-alkoxy)carbonyl, phenyl or phenyl-$C_1$–$C_6$-alkyl;

$R^{27}$, $R^{28}$, $R^{29}$, $R^{30}$ independently of one another are hydrogen, $C_1$–$C_6$-alkyl, $C_3$–$C_6$-alkenyl, $C_2$–$C_6$-alkynyl, $C_3$–$C_6$-cycloalkyl, $C_1$–$C_6$-haloalkyl, $C_1$–$C_6$-alkoxy-$C_1$–$C_6$-alkyl, $C_1$–$C_6$-alkylcarbonyl, ($C_1$–$C_6$-alkoxy)carbonyl, or $R^{27}$ and $R^{28}$ and/or $R^{29}$ and $R^{30}$ in each case together with the common nitrogen atom are a saturated or unsaturated 4- to 7-membered azo heterocycle which, in addition to carbon ring members, may, if desired, contain an oxygen atom or an —NH group;

m is 0, 1, 2 or 3.

$R^9$ is, in particular, halogen, and specifically fluorine or chlorine. $R^A$ is, in particular, hydrogen, i.e., m is 0.

In particular, $R^{10}$ in Q1 is:

$C_1$–$C_6$-alkoxy, $C_2$–$C_6$-alkenyloxy or $C_2$–$C_6$-alkynyloxy, where each of the 3 last-mentioned radicals may, if desired, carry one to three substituents, in each case selected from the group consisting of halogen, $C_1$–$C_6$-alkoxy, $C_3$–$C_6$-alkenyloxy, $C_3$–$C_6$-alkynyloxy, $C_1$–$C_6$-alkylsulfonyl, —CO—$R^{14}$, —CO—$OR^{14}$, —CO—N($R^{14}$)—$R^{15}$, —N($R^{14}$)—$R^{15}$, and —C($R^{16}$)=N—$OR^{13}$;

—CO—$R^{17}$, —C($NR^{18}$)—$R^{17}$, —C($R^{17}$)($OR^{19}$)($OR^{20}$), —C($R^{17}$)=C($R^{21}$)—CO—$R^{22}$, —CH($R^{17}$)—CH($R^{21}$)—CO—$R^{22}$, —CO—$OR^{26}$, —CO—N($R^{26}$)—$OR^{13}$, —C($R^{17}$)=C($R^{21}$)—CO—N($R^{26}$)—$OR^{13}$, —C($R^{16}$)=N—$OR^{13}$, —C($OR^{19}$)($OR^{20}$)—$OR^{26}$, —N($R^{27}$)$R^{28}$, —CON($R^{27}$)$R^{28}$ or —C($R^{17}$)=C($R^{27}$)CO—N($R^{27}$)$R^{28}$;

where $R^{13}$ to $R^{22}$ and $R^{26}$ to $R^{28}$ are as defined above, and is specifically $C_2$–$C_6$-alkenyloxy, $C_2$–$C_6$-alkynyloxy, —C($R^{17}$)($OR^{19}$)($OR^{20}$), —C($R^{17}$)=C($R^{21}$)—C(O)$R^{21}$, —CH($R^{17}$)—CH($R^{21}$)—C(O)$R^{22}$, C(O)$OR^{26}$, —C(O)—N($R^{26}$)—$OR^{13}$, —C($R^{16}$)=N—$OR^{13}$ and C(O)N($R^{27}$)$R^{28}$, in which $R^{13}$, $R^{16}$, $R^{17}$, $R^{19}$, $R^{20}$, $R^{21}$, $R^{22}$, $R^{26}$, $R^{27}$ and $R^{28}$ have the meanings given above and in particular those mentioned below:

$R^{13}$ is $C_1$–$C_6$-alkyl, $C_1$–$C_6$-haloalkyl, $C_3$–$C_6$-alkenyl, $C_3$–$C_6$-haloalkenyl, $C_3$–$C_6$-alkynyl, $C_1$–$C_6$-cyanoalkyl and $C_1$–$C_6$-alkoxycarbonyl-$C_1$–$C_6$-alkyl;

$R^{16}$ is hydrogen, $C_1$–$C_6$-alkyl, $C_1$–$C_6$-alkoxy, $C_1$–$C_6$-alkoxycarbonyl-$C_1$–$C_6$-alkyl, $C_1$–$C_6$-alkoxycarbonyl-$C_1$–$C_6$-alkoxy and phenoxycarbonyl-$C_1$–$C_6$-alkoxy;

$R^{17}$ is hydrogen, $C_1$–$C_6$-alkyl;

$R^{19}$ and $R^{20}$ independently of one another are $C_1$–$C_6$-alkyl;

$R^{21}$ is hydrogen, halogen, $C_1$–$C_6$-alkyl;

$R^{22}$ is hydroxyl, $C_1$–$C_6$-alkoxy, $C_1$–$C_6$-alkylthio, $C_1$–$C_6$-alkoxycarbonyl-$C_1$–$C_6$-alkyl;

$R^{26}$ is $C_1$–$C_6$-alkyl, $C_3$–$C_6$-haloalkyl, $C_3$–$C_6$-alkenyl, $C_3$–$C_6$-alkynyl, $C_1$–$C_6$-alkoxycarbonyl-$C_1$–$C_6$-alkyl, $C_3$–$C_6$-alkenyloxycarbonyl-$C_1$–$C_6$-alkyl, $C_3$–$C_6$-alkynyloxycarbonyl-$C_1$–$C_6$-alkyl, $C_1$–$C_6$-alkoxyalkyl;

$R^{27}$ is hydrogen, $C_1$–$C_6$-alkyl;

$R^{28}$ is hydrogen, $C_1$–$C_6$-alkyl, $C_1$–$C_6$-alkoxy,
  or $R^{27}$ and $R^{28}$ together are a 6-membered saturated azaheterocycle which may have one or two non-adjacent oxygen atoms in the ring.

To prepare the compounds of the formula V from the compounds of the formulae I and VI, it is preferred to add the isocyanate or the isothiocyanate of the formula VI over a period of 5 to 120 min, preferably within 10 to 30 min, to the compound I, which is preferably initially charged as a mixture with one of the solvents mentioned in step 1 of the preparation of I. However, it is also possible to initially charge the compound VI, preferably in one of the above-mentioned solvents, and to add the compound I thereto.

The reaction conditions correspond essentially to the reaction conditions mentioned in step 1 of the preparation of I.

The compound VI is preferably added to the compound I, or the compound I to the compound VI, at temperatures in the range from 0 to 50° C., in particular from 10 to 25° C. For the reaction to go to completion, the components are allowed extra reaction time of approximately 0.5 to 20 h, in particular 1 to 10 h, preferably at temperatures in the range from 20 to 80° C.

The reaction is preferably carried out under inert conditions, i.e. with exclusion of oxygen, for example under inert gases, in a dry, i.e. substantially water- and alcohol-free, solvent.

The reaction can be accelerated by adding a Lewis acid to activate the isocyanate or isothiocyanate of the formula VI. Lewis acids which are customary for this purpose are organotin compounds, for example, di-$C_2$–$C_8$-alkyltin(IV) dicarboxylates, such as di-n-butyltin(IV) diacetate. The Lewis acid is customarily employed in an amount of up to 15% by weight, preferably from 1 to 10% by weight, and in particular from 2 to 5% by weight, based on the isocyanate or the isothiocyanate of the formula VI.

The reaction can also be accelerated by addition of nucleophilic bases, for example pyridine, α-, β- or γ-picoline, quinoline, 4-dimethylaminopyridine or 4-pyrrolidinopyridine. The nucleophilic base is usually employed in an amount of up to 15% by weight, preferably from 0.5 to 10% by weight and in particular from 0.5 to 5% by weight, based on the compound VI.

The substituted ureas of the formula V obtainable in this manner are, on the one hand, effective herbicides. However, they are also suitable starting materials for preparing herbicides having a triazoline-2,5-dione structure (compounds of the formula VIII) if R is a radical which can be cleaved off from the compounds V, for example by hydrolysis.

Examples of hydrolysable radicals R are COOH, CHO, C(O)$OR^3$, C(S)$OR^3$, C(S)$SR^3$ and C(O)$SR^3$.

The hydrolysis of the N-substituted ureas with diazine structure (compounds V) to the compounds VII having an unsubstituted nitrogen in the 3-position succeeds in a simple manner by hydrolysis with water.

The reaction is advantageously carried out in the presence of an auxiliary base. The reaction temperature is usually in the range from 10 to 100° C., preferably in the range from 20 to 80° C.

The reaction is preferably carried out in a solvent, for example a water-miscible solvent, e.g. a $C_1$–$C_4$-alcohol, such as ethanol or methanol, a cyclic ether, such as tetrahydrofuran or dioxane, an amide, such as dimethylformamide, dimethylacetamide, N-methylpyrrolidone; dimethylsulfoxide, acetonitrile, a mixture of the abovementioned solvents with one another or a mixture with water, or in water itself.

Suitable bases are all of the abovementioned bases. Preference is given to alkali metal or alkaline earth metal hydroxide, particularly preferably sodium hydroxide.

The base is advantageously employed in a molar ratio of from 0.9 to 1.4, preferably from 0.95 to 1.2, particularly preferably from 0.98 to 1.15, for the ratio of substituted urea Ib to base.

The resulting compounds VII can be cyclized to the compounds VIII in accordance with the scheme below. Compounds VII and VIII have herbicidal activities.

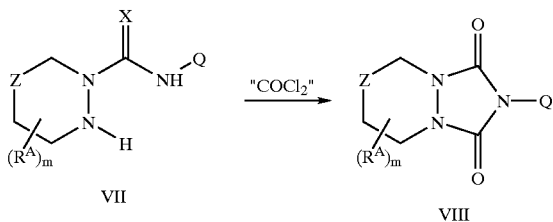

The cyclization of the 3-(arylcarbamoyl)tetrahydro-4H-1,3,4-oxa-(or thia)diazines VII is carried out using phosgene or a phosgene substitute, for example diphosgene (ClC(=O)OCCl$_3$), advantageously in the presence of one of the abovementioned anhydrous solvents, at temperatures in the range from –10 to 120° C., preferably from 0 to 80° C., particularly preferably from 10 to 60° C.

The phosgene is advantageously introduced at from 10 to 60° C. and with stirring into a mixture of VII and an amount of from 0.5 to 5% by weight, based on the starting material, of activated carbon as catalyst, in one of the abovementioned anhydrous solvents, over a period of from 0.5 to 20 hours, preferably from 1 to 12 hours.

The reaction can additionally be accelerated by a basic amide catalyst, for example DMF, which can usually be employed in an amount of from 0.3 to 10% by weight, based on the starting material. Suitable basic catalysts are also organic bases, such as triethylamine, tri-n-propylamine, N,N-dimethylaniline or N,N-dimethylcyclohexylamine. Preference is also given to using pyridine, if appropriate directly as solvent.

In place of phosgene, it is also possible to use diphosgene. The diphosgene is advantageously added with stirring at from 0 to –5° C. and over a period of from 2 to 20 min to the mixture of the starting material and one of the abovementioned solvents, if appropriate with addition of activated carbon, DMF or the organic base, and the mixture is allowed to warm to 10° C. over a period of 1 hour and then stirred at 10–60° C. for another 1 to 12 hours. The molar amount of phosgene or diphosgene is from 0.98 to 5, preferably from 1 to 3, particularly preferably from 1 to 1.3 mol per mole of starting material.

The concentration of the starting materials in the solvent is generally from 0.1 to 5 mol/l, preferably from 0.2 to 2 mol/l.

The reaction can be carried out under atmospheric pressure or superatmospheric pressure, continuously or batchwise.

The examples given below serve to illustrate the invention.

EXAMPLE 1

Methyl Tetrahydro-4H-1,3,4-oxadiazine-4-carboxylate (Compound According to the Invention)

a) Methyl N-Amino-N-2-hydroxyethylcarbamate (Compound IV.1a—See Table 3)

At 0–5° C., 248.4 g (2.628 mol) of methyl chloroformate were added with stirring, over a period of 30 min, to a mixture of 200 g (2.628 mol) of 2-hydrazinoethanol and 266 g (2.628 mol) of triethylamine in 1600 ml of methylene chloride. After 3 h of stirring at from 3 to 22 C, the resulting hydrochloride was removed by filtration and washed with THF. The filtrates were combined. The filter cake was suspended in 800 ml of THF and filtered again. This filtrate, too, was combined with the previous filtrate. The combined filtrates were concentrated under reduced pressure. This gave 366 g of the title compound as colorless oil having an HPLC purity of 95.3%, corresponding to a yield of 98.9% of theory. According to GC, the purity was 85.2%.

$^1$H-NMR (400 MHZ, d$_6$-DMSO) δ (ppm): 4.4–4.8 (broad/3H) NH$_2$/OH; 3.6 (s/3H) CH$_3$O; 3.52 (t/2H) and 3.35 (t/2H) CH$_2$—CH$_2$.

b) Methyl Tetrahydro-4H-1,3,4-oxadiazine-4-carboxylate (Compound Ib.1—See Table 4)

At 22° C., 22.4 g (0.746 mol) of paraformaldehyde were added with stirring, over a period of 2 min to a mixture of 100 g (0.746 mol) of methyl N-amino-N-2-hydroxyethylcarbamate in 1500 ml of methylene chloride. After addition of 8.5 g (0.045 mol) of p-toluenesulfonic acid, the mixture was stirred at 42° C. for 21 h, until the precipitate had dissolved, and was then cooled to 20° C., and magnesium sulfate was added. The mixture was filtered and the filtrate was concentrated under reduced pressure. This gave 111.8 g of the title compound as a colorless resin with a GC purity of 85%, corresponding to a yield of 85.8% of theory.

$^1$H-NMR (500 MHZ, CF$_3$CO$_2$D) δ (ppm): 5.09 (s/2H) CH$_2$; 4.02 (s/3H); CH$_3$O; 3.8–4.25 (m/4H) CH$_2$CH$_2$; IR ν (C=O) 1703 cm$^{-1}$.

The intermediates 2a to 15a listed in Table 3 were obtained analogously to Example 1a. Refractive index (n$^{23}$/$_D$) and/or characteristic IR bands (NH, CO) are stated in Table 3.

TABLE 3

HO(CH$_2$)$_2$—N(R)—NH$_2$

| Compound IV No. | R | n$^{23}$/$_D$ | ν [cm$^{-1}$] | Yield [%] |
|---|---|---|---|---|
| 1a | CO$_2$CH$_3$ | | | 98.9 |
| 2a | CO$_2$C$_2$H$_5$ | | C=O 1695 cm$^{-1}$, NH$_2$ 3336 cm$^{-1}$ | 88 |
| 3a | C(O)SCH$_3$ | 1.5458 | | 85 |
| 4a | C(O)SC$_2$H$_5$ | 1.5345 | | 86 |
| 5a | CO$_2$-i-C$_3$H$_7$ | | C=O 1694 cm$^{-1}$, NH$_2$ 3338 cm$^{-1}$ | 69 |
| 6a | CO$_2$-t-C$_4$H$_9$ | | | |

TABLE 3-continued $$HO(CH_2)_2\text{-}\underset{\underset{NH_2}{|}}{N}\text{-}R$$

| Compound IV No. | R | $n^{23}/_D$ | $\nu$ [cm$^{-1}$] | Yield [%] |
|---|---|---|---|---|
| 7a | CO$_2$-phenyl | | | |
| 8a | CO$_2$-p-Cl-phenyl | | | |
| 9a | CO$_2$-benzyl | | C=O 1706 cm$^{-1}$, NH$_2$ 3336 cm$^{-1}$ | 62 |
| 10a | C(S)OCH$_3$ | | | |
| 11a | CO$_2$-n-C$_8$H$_{17}$ | | | |
| 12a | CO$_2$CH$_2$CH$_2$Cl | 1.4988 | C=O 1706 cm$^{-1}$ | 65 |
| 13a | CO$_2$-Cyclopentyl | 1.4981 | C=O 1695 cm$^{-1}$ | 50 |
| 14a | CO$_2$-n-C$_{14}$H$_{19}$ | | C=O 1700 cm$^{-1}$ | 88 |
| 15a | COCH$_3$ | 1.4938 | | 22 |

$n^{23}/_D$ refractive index
$\nu$ [cm$^{-1}$] IR absorption

The target compounds of the formula Ib (compounds Ib.2b to Ib.15b) listed in Table 4 were obtained analogously to Example 1b. Refractive index, characteristic IR bands (NH, CO) and/or $^1$H-NMR data are given in Table 4.

TABLE 4

(Ia)

Structure: tetrahydro-1,3,4-oxadiazine ring with N-R and N-H substituents

| Ex. No. | R | $n^{23}/_D$ bp [° C./mbar] mp [° C.] | $\nu$ [cm$^{-1}$] | $^1$H-NMR [δ (ppm)] | Yield [%] |
|---|---|---|---|---|---|
| 1b | CO$_2$CH$_3$ | — | — | supra | 85.8 |
| 2b | CO$_2$C$_2$H$_5$ | 100–105/0.5 | C=O: 1701 | 4.05 (q/2H), O—CH$_2$—C; 1.18 (t/3H) CH$_3$ | 78 |
| 3b | C(O)SCH$_3$ | 103–111/0.4 1.5542 | C=O: 1659 | | 75 |
| 4b | C(O)SC$_2$H$_5$ | 1.5428 | C=O: 1657 | | 74 |
| 5b | CO$_2$-i-C$_3$H$_7$ | | C=O: 1702 | | 61 |
| 6b | CO$_2$-t-C$_4$H$_9$ | | | | |
| 7b | CO$_2$-phenyl | | | | |
| 8b | CO$_2$-p-Cl-phenyl | | | | |
| 9b | CO$_2$-benzyl | | | 7.4–7.24 (m, 5H) 5.1 (s, 2H) | 43 |
| 10b | C(S)OCH$_3$ | | | | |
| 11b | CO$_2$-n-C$_8$H$_{17}$ | | | | |
| 12b | CO$_2$CH$_2$CH$_2$Cl | 1.5130 | C=O 1709 | | 53 |
| 13b | CO$_2$-cyclopentyl | 145–150/0.5 | C=O 1700 | | 51 |
| 14b | CO$_2$-n-C$_{14}$H$_{29}$ | 77–81 | | | 59 |
| 15b | COCH$_3$ | | C=O 1683 | | 34 |

$n^{23}/_D$ refractive index
mp melting point
bp boiling point at given pressure

USE EXAMPLE 1

Process According to the Invention 1 a) Methyl 3-[N-(4'-Chloro-2'-fluoro-5'-propargyloxyphenyl)amino-carbonyl]tetrahydro-4H-1,3,4-oxadiazine-4-carboxylate Over a period of 10 min, 5.7 g (25.25 mmol) of 4-chloro-2-fluoro-5-propargyloxyphenylisocyanate in 50 ml THF were added with stirring, at 22° C., to a mixture of 3.7 g (25.25 mmol) of the compound from Example 1b in 150 ml THF, resulting in the reaction solution warming to 25° C. over a period of 1 h.

After 12 h at 22° C., the reaction solution was concentrated and chromatographed over silica gel using methylene chloride/ether 2:1. The concentration gave 7.4 g (79% of theory) of the title compound of m.p. 130° C.

1 b) 3-[N-(4-Chloro-2-fluoro-5-propargyloxyphenyl)aminocarbonyl]tetrahydro-4H-1,3,4-oxadiazine Over a period of 20 min, 0.41 g (10.35 mmol) of sodium hydroxide dissolved in 25 ml of water were added with stirring, at 60–70° C., to a solution of 3.5 g (9.42 mmol) of the compound from Example 1a in 75 ml of ethanol. According to thin-layer chromatography, the reaction went to completion. The mixture was cooled and substantially concentrated under reduced pressure. 50 ml of water were added and the mixture was then acidified using 1 N hydrochloric acid, resulting in evolution of gas with slight foaming and formation of a precipitate. The aqueous phase was extracted three times with methylene chloride and the combined extracts were dried under magnesium sulfate and concentrated to dryness under reduced pressure. This gave 3.0 g of a colorless powder of m.p. 138–142° C. According to GC/MS, the powder contained 1.71 g of the title compound (yield: 58% of theory).

The compound 1b and the comparative product below can be cyclized to herbicidal fused triazoles using, according to the prior art (WO 94/10173), phosgene or a phosgene substitute.

COMPARATIVE EXAMPLE (WO 94/10173)

Tetrahydro-4-[N-(4-chloro-2-fluoro-5-propargyloxyphenyl)amino-carbonyl-4H-1,3,4-oxadiazine 5.0 g (16.57 mmol of N-amino-N-2-hydroxyethyl-N'-(4-chloro-2-fluoro-5-propargyloxy-phenyl)urea, 1.5 g (12.2 mmol) of 37% strength formaldehyde and 0.5 g of p-toluenesulfonic acid were, at 42° C., stirred in methylene chloride for 17 h, using a Dean-Stark separator. After cooling, the reaction mixture was partially concentrated under reduced pressure and then chromatographed over 200 ml of silica gel, using methylene chloride and then ethyl acetate. This gave 3.6 g of a substance mixture which, according to TLC, HPLC and NMR, consisted of 6 to 7 substances. According to HPLC analysis with independently prepared material for comparison, 0.74 g (14.2% of theory) of the title compound was present.

When the column was rinsed with methanol, only p-toluenesulfonic acid could be isolated.

Thus, the process according to the invention gives compounds VII in considerably better yields, and therefore provides better access to the herbicides of the formula VIII.

We claim:
1. An N-substituted perhydro-3,4-diazine of formula

(I)

in which
Z is O;
$R^A$ is hydroxyl, $CO_2R^1$, halogen, cyano, $C(O)NR^1_2$, $OR^2$, $C_1$–$C_6$-alkyl, $C_1$–$C_6$-haloalkyl, $C_3$–$C_6$-alkenyl, $C_3$–$C_6$-alkynyl, $COR^1$, $S(O)_nR^1$ where n=0, 1 or 2, or $C(O)SR^1$;
R is $CO_2H$, CHO, CN, $C(O)OR^3$, $C(S)OR^3$, $C(O)SR^3$, $C(S)SR^3$, $C(O)NR^4R^5$, $C(S)NR^4R^5$, $C(O)NHCO_2R^6$, $C(O)NHSO_2R^6$, $C(O)NHSO_3R^6$, $C(O)R^2$, $P(O)R^1OR^1$, $P(O)(OR^1)_2$, $S(O)_nR^2$ where n=0, 1, or 2 or $SO_2NHR^1$;
m has the value 0, 1, 2 or 3
and in which the variables $R^1$ to $R^7$ are as defined below:
$R^1$ is hydrogen, $C_1$–$C_6$-alkyl, $C_1$–$C_6$-haloalkyl, $C_1$–$C_3$-alkoxy-$C_1$–$C_3$-alkyl, $C_3$–$C_6$-alkenyl or $C_3$–$C_6$-alkynyl;
$R^2$ is $C_1$–$C_6$-alkyl, $C_3$–$C_6$-cycloalkyl, $C_3$–$C_6$-alkenyl, $C_3$–$C_6$-alkynyl, $C_1$–$C_6$-haloalkyl, $C_1$–$C_6$-alkoxy-$C_1$–$C_6$-alkyl, hydroxycarbonyl-$C_1$–$C_6$-alkyl, $C_1$–$C_6$-alkoxycarbonyl-$C_1$–$C_6$-alkyl, $C_1$–$C_6$-alkylthio-$C_1$–$C_6$-alkyl, $C_1$–$C_6$-alkylsulfinyl-$C_1$–$C_6$-alkyl, $C_1$–$C_6$-alkylsulfonyl-$C_1$–$C_6$-alkyl, $C_3$–$C_6$-cycloalkyl-$C_1$–$C_6$-alkyl, $C_3$–$C_6$-alkenyloxycarbonyl-$C_1$–$C_6$-alkyl, $C_3$–$C_6$-alkynyloxycarbonyl-$C_1$–$C_6$-alkyl, $C_3$–$C_6$-cycloalkoxy-$C_1$–$C_6$-alkyl, $C_3$–$C_6$-alkenyloxy-$C_1$–$C_6$-alkyl, $C_3$–$C_6$-alkynyloxy-$C_1$–$C_6$-alkyl, $C_1$–$C_6$-haloalkoxy-$C_1$–$C_6$-alkyl, $C_3$–$C_6$-haloalkenyloxy-$C_1$–$C_6$-alkyl, $C_3$–$C_6$-haloalkynyloxy-$C_1$–$C_6$-alkyl, $C_3$–$C_6$-cycloalkyl-$C_1$–$C_6$-thioalkyl, $C_3$–$C_6$-alkenylthio-$C_1$–$C_6$-alkyl, $C_3$–$C_6$-alkynylthio-$C_1$–$C_6$-alkyl, cyano-$C_1$–$C_6$-alkyl, $C_3$–$C_6$-halocycloalkyl-$C_1$–$C_6$-alkyl, halo-$C_2$–$C_6$-alkenyl, $C_1$–$C_6$-alkoxy-$C_3$–$C_6$-alkenyl, $C_1$–$C_6$-haloalkoxy-$C_3$–$C_6$-alkenyl, $C_1$–$C_6$-alkylthio-$C_3$–$C_6$-alkenyl, $C_3$–$C_6$-haloalkynyl, $C_1$–$C_6$-alkoxy-$C_3$–$C_6$-alkynyl, $C_1$–$C_6$-haloalkoxy-$C_3$–$C_6$-alkynyl, $C_1$–$C_6$-alkylthio-$C_3$–$C_6$-alkynyl, $C_1$–$C_6$-alkylcarbonyl, $CHR^1COR^7$, $CHR^1P(O)(OR^7)_2$, $P(O)(OR^7)_2$, $CHR^1P(S)(OR^7)_2$, $CHR^1C(O)NR^4R^5$, $CHR^1C(O)NH_2$, or $R^2$ is phenyl, pyridyl, benzyl, phenoxy-$C_1$–$C_6$-alkyl, benzyloxy-$C_1$–$C_6$-alkyl, where the phenyl or pyridyl groups of the five last-mentioned substituents may be substituted by halogen, $C_1$–$C_4$-alkyl, $C_1$–$C_4$-alkoxy or $C_1$–$C_4$-haloalkyl, $R^3$ is $C_1$–$C_{15}$-alkyl, $C_3$–$C_8$-cycloalkyl, $C_2$–$C_{10}$-alkenyl, $C_3$–$C_{10}$-alkynyl, $C_1$–$C_6$-haloalkyl, $C_1$–$C_6$-alkoxy-$C_1$–$C_6$-alkyl, $C_1$–$C_6$-alkylthio-$C_1$–$C_6$-alkyl, $C_1$–$C_6$-alkylsulfinyl-$C_1$–$C_6$-alkyl, $C_1$–$C_6$-alkylsulfonyl-$C_1$–$C_6$-alkyl, $C_1$–$C_3$-alkoxy-$C_1$–$C_3$-alkoxy-$C_1$–$C_3$-alkyl, $C_3$–$C_6$-cycloalkyl-$C_1$–$C_6$-alkyl, carboxyl-$C_1$–$C_6$-alkyl, $C_1$–$C_6$-alkoxycarbonyl-$C_1$–$C_6$-alkyl, $C_1$–$C_6$-alkoxycarbonyl-$C_2$–$C_6$-alkenyl, $C_3$–$C_6$-alkenyloxycarbonyl-$C_1$–$C_6$-alkyl, $C_3$–$C_6$-alkynyloxycarbonyl-$C_1$–$C_6$-alkyl, $C_3$–$C_8$-cycloalkoxy-$C_1$–$C_6$-alkyl, $C_3$–$C_6$-alkenyloxy-$C_1$–$C_6$-alkyl, $C_3$–$C_6$-alkynyloxy-$C_1$–$C_6$-alkyl, $C_1$–$C_6$-haloalkoxy-$C_1$–$C_6$-alkyl, $C_3$–$C_6$-haloalkenyloxy-$C_1$–$C_6$-alkyl, $C_3$–$C_6$-haloalkynyloxy-$C_1$–$C_6$-alkyl, $C_3$–$C_6$-cycloalkyl-$C_1$–$C_6$-thioalkyl, $C_3$–$C_6$-alkenylthio-$C_1$–$C_6$-alkyl, $C_3$–$C_6$-alkynylthio-$C_1$–$C_6$-alkyl, cyano-$C_1$–$C_6$-alkyl, $C_3$–$C_6$-halocycloalkyl-$C_1$–$C_6$-alkyl, halo-$C_3$–$C_6$-alkenyl, $C_1$–$C_6$-alkoxy-$C_3$–$C_6$-alkenyl, $C_1$–$C_6$-haloalkoxy-$C_3$–$C_6$-alkenyl, $C_1$–$C_6$-alkylthio-$C_3$–$C_6$-alkenyl, $C_3$–$C_6$-haloalkynyl, $C_1$–$C_6$-alkoxy-$C_3$–$C_6$-alkynyl, $C_1$–$C_6$-haloalkoxy-$C_3$–$C_6$-alkynyl, $C_1$–$C_6$-alkylthio-$C_3$–$C_6$-alkynyl, or $R^3$ is $CHR^1COR^7$, $CHR^1P(O)(OR^7)_2$, $P(O)(OR^7)_2$, $CHR^1P(S)(OR^7)_2$, $CHR^1C(O)NR^4R^5$, $CHR^1C(O)NH_2$, phenoxy-$C_1$–$C_6$-alkyl, benzyloxy-$C_1$–$C_6$-alkyl, where the phenyl groups of the two last-mentioned substituents may be substituted by halogen, $C_1$–$C_4$-alkyl, $C_1$–$C_4$-alkoxy or $C_1$–$C_4$-haloalkyl; or $R^3$ is phenyl, pyridyl, naphthyl, quinolyl, quinazolyl, quinoxalyl, 1-methylindolyl, 1-methylbenzimidazolyl, 2-methylindazolyl, benzofuranyl, benzothienyl, benzoxazolyl, benzothiazolyl, benzyl, where the 14 last-mentioned substituents may carry, in adjacent positions, a divalent substituent selected from the group consisting of methylenedioxy, difluoromethylenedioxy, chlorofluoromethylenedioxy and dichloromethylenedioxy, or may in each case be mono- to pentasubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, $C_1$–$C_4$-monoalkylamino, $C_1$–$C_4$-dialkylamino, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano;

$R^4$ is hydrogen, $C_1$–$C_6$-alkyl or $C_1$–$C_6$-alkoxy;

$R^5$, $R^6$ independently of one another are hydrogen, $C_1$–$C_6$-alkyl, $C_2$–$C_6$-alkenyl, $C_2$–$C_6$-alkynyl, $C_3$–$C_6$-cycloalkyl, $C_1$–$C_6$-haloalkyl, $C_1$–$C_6$-alkoxy-$C_1$–$C_6$-alkyl, $C_1$–$C_6$-alkoxycarbonyl-$C_1$–$C_6$-alkyl, $C_1$–$C_6$-alkoxycarbonyl-$C_2$–$C_6$-alkenyl, where the alkenyl chain may additionally carry one to three halogen and/or cyano radicals, benzyl which, in adjacent positions of the phenyl ring, may carry a divalent substituent selected from the group consisting of methylenedioxy, difluoromethylenedioxy, chlorofluoromethylenedioxy and dichloromethylenedioxy, or which may be mono- to pentasubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano, or $R^4$ and $R^5$ together with the nitrogen atom to which they are attached are a saturated or unsaturated 4- to 7-membered azaheterocycle which, in addition to carbon ring members, optionally has one of the following members: —O—, —S—, —N=, —NH— or —N($C_1$–$C_6$-alkyl)—;

$R^7$ is hydrogen, $C_1$–$C_6$-alkyl, $C_1$–$C_6$-haloalkyl, $C_1$–$C_3$-alkoxy-$C_1$–$C_3$-alkyl, $C_2$–$C_6$-cyanoalkyl, $C_3$–$C_6$-alkenyl or $C_3$–$C_6$-alkynyl.

2. The perhydrodiazine of formula I defined in claim 1 in which $R^1$ is hydrogen, $C_1$–$C_6$-alkyl, $C_1$–$C_6$-haloalkyl, $C_1$–$C_3$-alkoxy-$C_1$–$C_3$-alkyl, $C_3$–$C_6$-alkenyl or $C_3$–$C_6$-alkynyl;

$R^2$ is $C_1$–$C_6$-alkyl, $C_3$–$C_6$-cycloalkyl, $C_3$–$C_6$-alkenyl, $C_3$–$C_6$-alkynyl, $C_1$–$C_6$-haloalkyl, $C_1$–$C_6$-alkoxy-$C_2$–$C_6$-alkyl, $C_1$–$C_6$-alkoxycarbonyl-$C_1$–$C_6$-alkyl, $C_1$–$C_6$-alkylthio-$C_1$–$C_6$-alkyl, $C_3$–$C_6$-alkenyloxycarbonyl-$C_1$–$C_6$-alkyl, $C_3$–$C_6$-alkynyloxycarbonyl-$C_1$–$C_6$-alkyl, $C_3$–$C_6$-alkenyloxy-$C_1$–$C_6$-alkyl, $C_3$–$C_6$-alkynyloxy-$C_1$–$C_6$-alkyl, $C_1$–$C_6$-haloalkoxy-$C_1$–$C_6$-alkyl, cyano-$C_1$–$C_6$-alkyl, halo-$C_2$–$C_6$-alkenyl, halo-$C_3$–$C_6$-alkynyl, $C_1$–$C_6$-alkylcarbonyl, $CHR_1COR^7$, $P(O)(OR^7)_2$, $CHR^1P(S)(OR^7)_2$, $CHR^1C(O)NR^4R^5$, $CHR^1C(O)NH_2$, or $R^2$ is benzyl, phenyl, phenoxy-$C_1$–$C_6$-alkyl or benzyloxy-$C_1$–$C_6$-alkyl, where the four last-mentioned substituents may be substituted by halogen, $C_1$–$C_4$-alkyl or $C_1$–$C_4$-haloalkyl;

$R^3$ is $C_1$–$C_{15}$-alkyl, $C_3$–$C_8$-cycloalkyl, $C_2$–$C_{10}$-alkenyl, $C_3$–$C_{10}$-alkynyl, $C_1$–$C_6$-haloalkyl, $C_1$–$C_6$-alkoxy-$C_1$–$C_6$-alkyl, $C_1$–$C_6$-alkylthioalkyl, $C_1$–$C_6$-alkoxycarbonyl-$C_1$–$C_6$-alkyl, $C_3$–$C_6$-alkenyloxycarbonyl-$C_1$–$C_6$-alkyl, $C_3$–$C_6$-alkynyloxycarbonyl-$C_1$–$C_6$-alkyl, $C_3$–$C_6$-alkenyloxy-$C_1$–$C_6$-alkyl, $C_1$–$C_6$-haloalkoxy-$C_1$–$C_6$-alkyl, cyano-$C_1$–$C_6$-alkyl, halo-$C_3$–$C_6$-alkenyl, $C_1$–$C_6$-alkoxy-$C_3$–$C_6$-alkenyl, $C_1$–$C_6$-alkoxy-$C_3$–$C_6$-alkynyl, $CHR^1COR^7$, $P(O)(OR^7)_2$, $CHR^1P(S)(OR^7)_2$, $CHR^1C(O)NR^4R^5$, $CHR^1C(O)NH_2$, or $R^3$ is benzyl, phenyl, phenoxy-$C_1$–$C_6$-alkyl or benzyloxy-$C_1$–$C_6$-alkyl, where the four last-mentioned substituents may be substituted by halogen, $C_1$–$C_4$-alkyl or $C_1$–$C_4$-haloalkyl;

$R^4$ is hydrogen, $C_1$–$C_6$-alkyl or $C_1$–$C_6$-alkoxy;

$R^5$, $R^6$ independently of one another are hydrogen, $C_1$–$C_6$-alkyl, $C_2$–$C_6$-alkenyl, $C_2$–$C_6$-alkynyl, $C_3$–$C_6$-cycloalkyl, $C_1$–$C_6$-haloalkyl, $C_1$–$C_6$-alkoxy-$C_1$–$C_6$-alkyl, $C_1$–$C_6$-alkoxycarbonyl-$C_1$–$C_6$-alkyl, $C_1$–$C_6$-alkoxycarbonyl-$C_2$–$C_6$-alkenyl, benzyl which may be mono- to pentasubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkoxycarbonyl, $C_1$–$C_4$-alkoxycarbonyl-$C_1$–$C_4$-alkyl, nitro or cyano, or $R^4$ and $R^5$ together with the common nitrogen atom are a saturated or unsaturated 4- to 7-membered azaheterocycle which, in addition to the carbon ring members optionally has one of the following members: —O—, —S—, —N=, —NH— or —N($C_1$–$C_6$-alkyl)—;

$R^7$ is hydrogen, $C_1$–$C_6$-alkyl, $C_1$–$C_6$-haloalkyl, $C_1$–$C_3$-alkoxy-$C_1$–$C_3$-alkyl, $C_2$–$C_6$-cyanoalkyl, $C_3$–$C_6$-alkenyl or $C_3$–$C_6$-alkynyl.

3. The perhydrodiazine of formula I defined in claim 1 in which R is selected from $C(O)OR^3$, $C(S)OR^3$, $C(O)SR^3$, $C(S)SR^3$.

4. The perhydrodiazine of formula I defined in claim 1 in which m has the value 0.

5. A process for preparing the perhydrodiazine of formula I defined in claim 1, which comprises at least two successive reaction steps, where, in a first reaction step, a substituted hydrazine of formula II $$(R^A)_m \quad \text{(II)}$$

(structure with HZ and NH–NH$_2$)

is reacted with an acid compound of formula III $$R—G \quad \text{(III)}$$

in which G is a nucleophilically displaceable leaving group, or R—G is a compound of formula $R^5$—N=C=X or of formula $R^{2a}(R^{2b})C$=C=X in which X is O or S and $R^{2a}(R^{2b})C$—H is the radical $R^2$, and the resulting hydrazide compound of formula IV $$(R^A)_m \quad \text{(IV)}$$

(structure with HZ, N–R, NH$_2$)

is, in a second step, cyclized with formaldehyde in the presence of an acid to give the perhydrodiazines of formula I, and optionally further derivatizing R.

6. A process for preparing an urea of formula V $$(V)$$

(structure showing $(R^A)_m$, Z, ring with N, N–R, and N(H)–C(=X)–Q)

in which

X is O or S;

Q is a $C_6$–$C_{14}$-aromatic radical which is at least monosubstituted and/or attached via two adjacent carbon atoms to a saturated or unsaturated 4- to 7-membered cycle which, in addition to the carbon ring members, optionally has one, two or three members selected from the group consisting of: —O—, —S—, —S(O)$_2$—, —N=, —NH— and —N($C_1$–$C_6$-alkyl)—;

Z is O;

$R^A$ is hydroxyl, $CO_2R^1$, halogen, cyano, $C(O)NR^1{}_2$, $OR^2$, $C_1$–$C_6$-alkyl, $C_1$–$C_6$-haloalkyl, $C_3$–$C_6$-alkenyl, $C_3$–$C_6$-alkynyl, $COR^1$, $S(O)_nR^1$ where n=0, 1 or 2, or $C(O)SR^1$;

R is $CO_2H$, CHO, CN, $C(O)OR^3$, $C(S)OR^3$, $C(O)SR^3$, $C(S)SR^3$, $C(O)NR^4R^5$, $C(S)NR^4R^5$, $C(O)NHCO_2R^6$, $C(O)NHSO_2R^6$, $C(O)NHSO_3R^6$, $C(O)R^2$, $P(O)R^1OR^1$, $P(O)(OR^1)_2$, $S(O)_nR^2$ where n=0, 1, or 2 or $SO_2NHR^1$;

m has the value 0, 1, 2 or 3;

and in which the variables $R^1$ to $R^7$ are as defined below:

$R^1$ is hydrogen, $C_1$–$C_6$-alkyl, $C_1$–$C_6$-haloalkyl, $C_1$–$C_3$-alkoxy-$C_1$–$C_3$-alkyl, $C_3$–$C_6$-alkenyl or $C_3$–$C_6$-alkynyl;

$R^2$ is $C_1$–$C_6$-alkyl, $C_3$–$C_6$-cycloalkyl, $C_3$–$C_6$-alkenyl, $C_3$–$C_6$-alkynyl, $C_1$–$C_6$-haloalkyl, $C_1$–$C_6$-alkoxy-$C_1$–$C_6$-alkyl, hydroxycarbonyl-$C_1$–$C_6$-alkyl, $C_1$–$C_6$-alkoxycarbonyl-$C_1$–$C_6$-alkyl, $C_1$–$C_6$-alkylthio-$C_1$–$C_6$-alkyl, $C_1$–$C_6$-alkylsulfinyl-$C_1$–$C_6$-alkyl, $C_1$–$C_6$-alkylsulfonyl-$C_1$–$C_6$-alkyl, $C_3$–$C_6$-cycloalkyl-$C_1$–$C_6$-alkyl, $C_3$–$C_6$-alkenyloxycarbonyl-$C_1$–$C_6$-alkyl, $C_3$–$C_6$-alkynyloxycarbonyl-$C_1$–$C_6$-alkyl, $C_3$–$C_6$-cycloalkoxy-$C_1$–$C_6$-alkyl, $C_3$–$C_6$-alkenyloxy-$C_1$–$C_6$-alkyl, $C_3$–$C_6$-alkynyloxy-$C_1$–$C_6$-alkyl, $C_1$–$C_6$-haloalkoxy-$C_1$–$C_6$-alkyl, $C_3$–$C_6$-haloalkenyloxy-$C_1$–$C_6$-alkyl, $C_3$–$C_6$-haloalkynyloxy-$C_1$–$C_6$-alkyl, $C_3$–$C_6$-cycloalkyl-$C_1$–$C_6$-thioalkyl, $C_3$–$C_6$-alkenylthio-$C_1$–$C_6$-alkyl, $C_3$–$C_6$-alkynylthio-$C_1$–$C_6$-alkyl, cyano-$C_1$–$C_6$-alkyl, $C_3$–$C_6$-halocycloalkyl-$C_1$–$C_6$-alkyl, halo-$C_2$–$C_6$-alkenyl, $C_1$–$C_6$-alkoxy-$C_3$–$C_6$-alkenyl, $C_1$–$C_6$-haloalkoxy-$C_3$–$C_6$-alkenyl, $C_1$–$C_6$-alkylthio-$C_3$–$C_6$-alkenyl, $C_3$–$C_6$-haloalkynyl, $C_1$–$C_6$-alkoxy-$C_3$–$C_6$-alkynyl, $C_1$–$C_6$-haloalkoxy-$C_3$–$C_6$-alkynyl, $C_1$–$C_6$-alkylthio-$C_3$–$C_6$-alkynyl, $C_1$–$C_6$-alkylcarbonyl, $CHR^1COR^7$, $CHR^1P(O)(OR^7)_2$, $P(O)(OR^7)_2$, $CHR^1P(S)(OR^7)_2$, $CHR^1C(O)NR^4R^5$, $CHR^1C(O)NH_2$, or $R^2$ is phenyl, pyridyl, benzyl, phenoxy-$C_1$–$C_6$-alkyl, benzyloxy-$C_1$–$C_6$-alkyl, where the phenyl or pyridyl groups of the five last-mentioned substituents may be substituted by halogen, $C_1$–$C_4$-alkyl, $C_1$–$C_4$-alkoxy or $C_1$–$C_4$-haloalkyl;

$R^3$ is $C_1$–$C_{15}$-alkyl, $C_3$–$C_8$-cycloalkyl, $C_2$–$C_{10}$-alkenyl, $C_3$–$C_{10}$-alkynyl, $C_1$–$C_6$-haloalkyl, $C_1$–$C_6$-alkoxy-$C_1$–$C_6$-alkyl, $C_1$–$C_6$-alkylthio-$C_1$–$C_6$-alkyl, $C_1$–$C_6$-alkylsulfinyl-$C_1$–$C_6$-alkyl, $C_1$–$C_6$-alkylsulfonyl-$C_1$–$C_6$-alkyl, $C_1$–$C_3$-alkoxy-$C_1$–$C_3$-alkoxy-$C_1$–$C_3$-alkyl, $C_3$–$C_6$-cycloalkyl-$C_1$–$C_6$-alkyl, carboxyl-$C_1$–$C_6$-alkyl, $C_1$–$C_6$-alkoxycarbonyl-$C_1$–$C_6$-alkyl, $C_1$–$C_6$-alkoxycarbonyl-$C_2$–$C_6$-alkenyl, $C_3$–$C_6$-alkenyloxycarbonyl-$C_1$–$C_6$-alkyl, $C_3$–$C_6$-alkynyloxycarbonyl-$C_1$–$C_6$-alkyl, $C_3$–$C_8$-cycloalkoxy-$C_1$–$C_6$-alkyl, $C_3$–$C_6$-alkenyloxy-$C_1$–$C_6$-alkyl, $C_3$–$C_6$-alkynyloxy-$C_1$–$C_6$-alkyl, $C_1$–$C_6$-haloalkoxy-$C_1$–$C_6$-alkyl, $C_3$–$C_6$-haloalkenyloxy-$C_1$–$C_6$-alkyl, $C_3$–$C_6$-haloalkynyloxy-$C_1$–$C_6$-alkyl, $C_3$–$C_6$-cycloalkyl-$C_1$–$C_6$-thioalkyl, $C_3$–$C_6$-alkenylthio-$C_1$–$C_6$-alkyl, $C_3$–$C_6$-alkynylthio-$C_1$–$C_6$-alkyl, cyano-$C_1$–$C_6$-alkyl, $C_3$–$C_6$-halocycloalkyl-$C_1$–$C_6$-alkyl, halo-$C_3$–$C_6$-alkenyl, $C_1$–$C_6$-alkoxy-$C_3$–$C_6$-alkenyl, $C_1$–$C_6$-haloalkoxy-$C_3$–$C_6$-alkenyl, $C_1$–$C_6$-alkylthio-$C_3$–$C_6$-alkenyl, $C_3$–$C_6$-haloalkynyl, $C_1$–$C_6$-alkoxy-$C_3$–$C_6$-alkynyl, $C_1$–$C_6$-haloalkoxy-$C_3$–$C_6$-alkynyl, $C_1$–$C_6$-alkylthio-$C_3$–$C_6$-alkynyl, or $R^3$ is $CHR^1COR^7$, $CHR^1P(O)(OR^7)_2$, $P(O)(OR^7)_2$, $CHR^1P(S)(OR^7)_2$, $CHR^1C(O)NR^4R^5$, $CHR^1C(O)NH_2$, phenoxy-$C_1$–$C_6$-alkyl, benzyloxy-$C_1$–$C_6$-alkyl, where the phenyl groups of the two last-mentioned substituents may be substituted by halogen, $C_1$–$C_4$-alkyl, $C_1$–$C_4$-alkoxy or $C_1$–$C_4$-haloalkyl; or $R^3$ is phenyl, pyridyl, naphthyl, quinolyl, quinazolyl, quinoxalyl, 1-methylindolyl, 1-methylbenzimidazolyl, 2-methylindazolyl, benzofuranyl, benzothienyl, benzoxazolyl, benzothiazolyl, benzyl, where the 14 last-mentioned substituents may carry, in adjacent positions, a divalent substituent selected from the group consisting of methylenedioxy, difluoromethylenedioxy, chlorofluoromethylenedioxy and dichloromethylenedioxy, or may in each case be mono- to pentasubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, $C_1$–$C_4$-monoalkylamino, $C_1$–$C_4$-dialkylamino, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano;

$R^4$ is hydrogen, $C_1$–$C_6$-alkyl or $C_1$–$C_6$-alkoxy;

$R^5$, $R^6$ independently of one another are hydrogen, $C_1$–$C_6$-alkyl, $C_2$–$C_6$-alkenyl, $C_2$–$C_6$-alkynyl, $C_3$–$C_6$-cycloalkyl, $C_1$–$C_6$-haloalkyl, $C_1$–$C_6$-alkoxy-$C_1$–$C_6$-alkyl, $C_1$–$C_6$-alkoxycarbonyl-$C_1$–$C_6$-alkyl, $C_1$–$C_6$-alkoxycarbonyl-$C_2$–$C_6$-alkenyl, where the alkenyl chain may additionally carry one to three halogen and/or cyano radicals, benzyl which, in adjacent positions of the phenyl ring, may carry a divalent substituent selected from the group consisting of methylenedioxy, difluoromethylenedioxy, chlorofluoromethylenedioxy and dichloromethylenedioxy, or which may be mono- to pentasubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano, or $R^4$ and $R^5$ together with the nitrogen atom to which they are attached are a saturated or unsaturated 4- to 7-membered azaheterocycle which, in addition to carbon ring members, optionally has one of the following members: —O—, —S—, —N=, —NH— or —N($C_1$–$C_6$-alkyl)—, and $R^7$ is hydrogen, $C_1$–$C_6$-alkyl, $C_1$–$C_6$-haloalkyl, $C_1$–$C_3$-alkoxy-$C_1$–$C_3$-alkyl, $C_2$–$C_6$-cyanoalkyl, $C_3$–$C_6$-alkenyl or $C_3$–$C_6$-alkynyl;

which comprises reacting the perhydrodiazine of formula I defined in claim 1 with an isocyanate or an isothiocyanate of formula VI $$Q\text{—}N\text{=}C\text{=}X \qquad (VI).$$

* * * * *